United States Patent
Fabrikant et al.

(10) Patent No.: US 11,027,062 B2
(45) Date of Patent: Jun. 8, 2021

(54) LIQUID TRANSFER DEVICE WITH TELESCOPIC VIAL ADAPTER FOR USE WITH INFUSION LIQUID CONTAINER AND DISCRETE INJECTION VIAL

(71) Applicant: West Pharma. Services IL, Ltd., Ra'anana (IL)

(72) Inventors: Elisheva Fabrikant, Herzliya (IL); Igor Denenburg, Gedera (IL); Amir Lev, Kfar Saba (IL); Uri David, Nes Ziona (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/769,222

(22) PCT Filed: Dec. 3, 2018

(86) PCT No.: PCT/IB2018/059577
§ 371 (c)(1),
(2) Date: Jun. 2, 2020

(87) PCT Pub. No.: WO2019/106642
PCT Pub. Date: Jun. 6, 2019

(65) Prior Publication Data
US 2020/0376194 A1    Dec. 3, 2020

(30) Foreign Application Priority Data
Dec. 3, 2017    (IL) .......................................... 256074
Jun. 24, 2018    (IL) .......................................... 260220

(51) Int. Cl.
*A61M 5/168*    (2006.01)
*A61M 5/162*    (2006.01)
(Continued)

(52) U.S. Cl.
CPC ........ *A61M 5/162* (2013.01); *A61M 5/16804* (2013.01); *A61M 39/105* (2013.01);
(Continued)

(58) Field of Classification Search
CPC .............. A61M 5/162; A61M 5/16804; A61M 39/105; A61M 39/223; A61M 2039/0027; A61M 2039/229; A61J 1/2096
See application file for complete search history.

(56) References Cited

U.S. PATENT DOCUMENTS 1,021,681 A    3/1912    Jennings
3,822,700 A    7/1974    Pennington
(Continued)

FOREIGN PATENT DOCUMENTS

CN    201330626512        12/2013
DE           4408498 A1       5/1995
(Continued)

OTHER PUBLICATIONS

Int'l Search Report and Written Opinion dated Mar. 29, 2019 in Int'l Application No. PCT/IB2018/059577.
(Continued)

*Primary Examiner* — Nathan R Price
*Assistant Examiner* — Melissa A Snyder
(74) *Attorney, Agent, or Firm* — Panitch Schwarze Belisario & Nadel LLP

(57) ABSTRACT

A liquid transfer device is described. The liquid transfer device comprising a vial adapter comprising a puncturing cannula for puncturing an injection vial stopper, an IV spike and a substitute IV port holder for receiving a substitute IV port, and a flow control member port. The IV spike, the substitute IV port holder and the puncturing cannula are in flow communication with the flow control member port. The liquid transfer device comprising a flow control member
(Continued)

sealingly inserted in the flow control member port. Rotation of the flow control member between a plurality of positions controls flow communication of the liquid transfer device, the positions comprising a mixing position for enabling flow communication between the IV spike and the puncturing cannula; and an administering position for enabling flow communication between the IV spike and the substitute IV port holder.

15 Claims, 33 Drawing Sheets

(51) Int. Cl.
    *A61M 39/10*     (2006.01)
    *A61M 39/22*     (2006.01)
    *A61M 39/28*     (2006.01)
    *A61M 39/00*     (2006.01)

(52) U.S. Cl.
    CPC ........ *A61M 39/223* (2013.01); *A61M 39/284* (2013.01); *A61M 2039/0027* (2013.01); *A61M 2039/229* (2013.01); *A61M 2205/581* (2013.01)

(56) References Cited

U.S. PATENT DOCUMENTS

| | | |
|---|---|---|
| 3,938,520 A | 2/1976 | Scislowicz et al. |
| 4,121,585 A | 10/1978 | Becker, Jr. |
| 4,262,671 A | 4/1981 | Kersten |
| 4,364,387 A | 12/1982 | Larkin |
| D268,871 S | 5/1983 | Benham et al. |
| 4,573,993 A | 3/1986 | Hoag et al. |
| 4,581,014 A | 4/1986 | Millerd et al. |
| 4,752,292 A | 6/1988 | Lopez et al. |
| 4,834,744 A | 5/1989 | Ritson |
| 4,857,062 A | 8/1989 | Russell |
| 4,931,040 A | 6/1990 | Haber et al. |
| 4,932,944 A | 6/1990 | Jagger et al. |
| 5,006,114 A | 4/1991 | Rogers et al. |
| 5,125,915 A | 6/1992 | Berry et al. |
| D328,788 S | 8/1992 | Sagae et al. |
| D331,281 S | 11/1992 | Levine |
| 5,181,508 A | 1/1993 | Poole, Jr. |
| D337,828 S | 7/1993 | Gordon |
| D341,420 S | 11/1993 | Conn |
| 5,445,630 A | 8/1995 | Richmond |
| D362,718 S | 9/1995 | Deily et al. |
| 5,603,706 A | 2/1997 | Wyatt et al. |
| 5,645,538 A | 7/1997 | Richmond |
| 5,647,845 A | 7/1997 | Haber et al. |
| 5,651,776 A | 7/1997 | Appling et al. |
| 5,676,346 A | 10/1997 | Leinsing |
| 5,766,211 A | 6/1998 | Wood et al. |
| 5,776,116 A | 7/1998 | Lopez et al. |
| 5,782,872 A | 7/1998 | Muller |
| 5,887,633 A | 3/1999 | Yale et al. |
| 5,897,526 A | 4/1999 | Vaillancourt |
| 5,911,710 A | 6/1999 | Barry et al. |
| 5,935,112 A | 8/1999 | Stevens et al. |
| D414,562 S | 9/1999 | Tajima |
| D416,086 S | 11/1999 | Parris et al. |
| D417,733 S | 12/1999 | Howell et al. |
| 6,053,899 A | 4/2000 | Slanda et al. |
| 6,099,511 A | 8/2000 | Devos et al. |
| D431,864 S | 10/2000 | Jansen |
| 6,142,446 A | 11/2000 | Leinsing |
| 6,146,362 A | 11/2000 | Turnbull et al. |
| 6,171,287 B1 | 1/2001 | Lynn et al. |
| 6,179,823 B1 | 1/2001 | Niedospial, Jr. |
| 6,221,041 B1 | 4/2001 | Russo |
| 6,221,065 B1 | 4/2001 | Davis |
| 6,290,688 B1 | 9/2001 | Lopez et al. |
| D453,221 S | 1/2002 | Haytman et al. |
| D457,954 S | 5/2002 | Wallace et al. |
| 6,440,107 B1 | 8/2002 | Trombley, III et al. |
| 6,453,949 B1 | 9/2002 | Chau |
| D468,015 S | 12/2002 | Horppu |
| D482,121 S | 11/2003 | Harding et al. |
| D482,447 S | 11/2003 | Harding et al. |
| D483,487 S | 12/2003 | Harding et al. |
| 6,706,022 B1 | 3/2004 | Leinsing et al. |
| 7,070,589 B2 | 7/2006 | Lolachi et al. |
| 7,192,423 B2 | 3/2007 | Wong |
| 7,241,285 B1 | 7/2007 | Dikeman |
| D560,815 S | 1/2008 | Tajima |
| 7,326,188 B1 | 2/2008 | Russell et al. |
| D573,250 S | 7/2008 | MacRae et al. |
| D575,314 S | 8/2008 | Hind |
| D580,558 S | 11/2008 | Shigesada et al. |
| 7,544,191 B2 | 6/2009 | Peluso et al. |
| D604,837 S | 11/2009 | Crawford et al. |
| D609,804 S | 2/2010 | Uchida et al. |
| D634,007 S | 3/2011 | Zinger et al. |
| D641,080 S | 7/2011 | Zinger et al. |
| 8,122,923 B2 | 2/2012 | Kraus et al. |
| D671,654 S | 11/2012 | Akamatsu et al. |
| 8,317,741 B2 * | 11/2012 | Kraushaar ............ A61J 1/2096 604/82 |
| 8,418,690 B2 | 4/2013 | Power et al. |
| D691,264 S | 10/2013 | Dallemagne et al. |
| D703,812 S | 4/2014 | Cederschiold et al. |
| D720,451 S | 12/2014 | Denenburg et al. |
| D720,850 S | 1/2015 | Hsia et al. |
| D833,599 S | 11/2018 | Nilsson et al. |
| D849,936 S | 5/2019 | Allard |
| 10,413,662 B2 | 9/2019 | Yeh et al. |
| D881,389 S | 4/2020 | Wang et al. |
| D881,390 S | 4/2020 | Wang et al. |
| 2002/0128628 A1 | 9/2002 | Fathallah |
| 2003/0073971 A1 | 4/2003 | Saker |
| 2003/0191445 A1 | 10/2003 | Wallen et al. |
| 2003/0199847 A1 | 10/2003 | Akerlund et al. |
| 2005/0015070 A1 | 1/2005 | Delnevo et al. |
| 2005/0182383 A1 | 8/2005 | Wallen |
| 2006/0058741 A1 | 3/2006 | Gallagher |
| 2006/0095015 A1 | 5/2006 | Hobbs et al. |
| 2006/0106360 A1 | 5/2006 | Wong |
| 2007/0079894 A1 | 4/2007 | Kraus et al. |
| 2007/0249995 A1 | 10/2007 | Van Manen |
| 2009/0257306 A1 | 10/2009 | Coffeen et al. |
| 2010/0168664 A1 | 7/2010 | Zinger et al. |
| 2011/0004184 A1 | 1/2011 | Proksch et al. |
| 2011/0275988 A1 | 11/2011 | Davis et al. |
| 2012/0220978 A1 | 8/2012 | Lev et al. |
| 2013/0046269 A1 | 2/2013 | Lev et al. |
| 2013/0315026 A1 | 11/2013 | Cheio De Oliveira et al. |
| 2014/0276215 A1 | 9/2014 | Nelson et al. |
| 2014/0352845 A1 | 12/2014 | Lev et al. |
| 2015/0082746 A1 | 3/2015 | Ivosevic et al. |
| 2015/0088078 A1 | 3/2015 | Lev et al. |
| 2015/0209230 A1 | 7/2015 | Lev et al. |
| 2015/0250681 A1 | 9/2015 | Lev et al. |
| 2015/0297880 A1 | 10/2015 | Ogawa et al. |
| 2016/0081308 A1 | 3/2016 | Cary et al. |
| 2016/0081878 A1 | 3/2016 | Marks et al. |
| 2018/0161243 A1 | 6/2018 | Ariagno et al. |
| 2019/0083357 A1 | 3/2019 | David et al. |
| 2019/0117514 A1 | 4/2019 | Denenburg et al. |
| 2019/0343725 A1 | 11/2019 | Denenburg |
| 2020/0093692 A1 | 3/2020 | Lev et al. |
| 2020/0276084 A1 | 9/2020 | Denenburg |
| 2020/0330326 A1 | 10/2020 | Merchant et al. |

FOREIGN PATENT DOCUMENTS

| | | |
|---|---|---|
| DE | 102007046951 B3 | 2/2009 |
| EM | 001126270-0001 | 4/2009 |
| EM | 001680703 | 3/2010 |
| EM | 002446062 | 4/2014 |
| EM | 006630893 | 7/2019 |
| EP | 0856331 A2 | 8/1998 |

(56) References Cited

FOREIGN PATENT DOCUMENTS

| | | |
|---|---|---|
| JP | D201915749 | 7/2019 |
| WO | 9507720 A1 | 3/1995 |
| WO | 9513785 A1 | 5/1995 |
| WO | 03079956 A1 | 10/2003 |
| WO | 2007052252 A1 | 5/2007 |
| WO | 2008081424 A2 | 7/2008 |
| WO | 2009140511 A1 | 11/2009 |
| WO | 2010061743 A1 | 6/2010 |
| WO | 2011025719 A1 | 3/2011 |
| WO | 2011150037 A1 | 12/2011 |
| WO | 2015009746 A2 | 1/2015 |
| WO | 2015019343 A1 | 2/2015 |
| WO | 2018104930 A1 | 6/2018 |
| WO | 2018178971 A1 | 10/2018 |

OTHER PUBLICATIONS

Summit International Medical Technologies, Inc., Vial Direct to Bag Spike, 2020.

Merchant "An engineered control device for needle free reconstitution and transfer of compounded sterile intravenous drug solutions for immediate use to assist in complying with United States Pharmacopeia Chapter <797> standard", Adv Care, 2 pages, 2018.

Int'l Search Report and Written Opinion dated May 6, 2008 in Int'l Application No. PCT/IL2006/001228.

Int'l Search Report and Written Opinon dated Oct. 17, 2014 in Int'l Application No. PCT/IL2014/050680.

West Vial2Bag DC system, Oct. 2, 2014, https://web.archive.org/web/2014002065133/http://www.westpharma.com/en/products/Pages/Reconstitutionsystems.aspx.

Youtube.com, Vial2Bag DC, Aug. 21, 2014, https://www.youtube.com/watch?v=FEOkglxNBrs.

Int'l Search Report dated Apr. 24, 2020 in Int'l Application No. PCT/US2020/050020.

Article with picture of West Pharmaceutical Services Vial2Bag Needleless System, [on-line]; IPIPS Newsletter, Oct. 26, 2007], [retrieved from Internet Feb. 16, 2010]; URL: ,http://www.isips.org/reports/ISIPS_Newsletter_October_26_2007.html.> (7 pages, see pp. 5-6).

Int'l Search Report and Written Opinion dated Jul. 21, 2020 in Int'l Application No. PCT/IL2020/050362.

Facebook "West Pharmaceutical Services, Inc.", first available Oct. 21, 2014 (https://www.facebook.com/westpharma/photos/710246859056351)(2014).

YouTube, "vial2Bag DC", first available Feb. 1, 2018, (https://www.youtube.com/Watch?v=abSKPo5e_Hg) (Year:2018).

YouTube, "ADVCARE—Vial Direct to bag Spoke", first available Oct. 31, 2018 (https://www.youtube.com/watch?v=dd8ctggkrfM&feature=emb_title)(2018).

\* cited by examiner

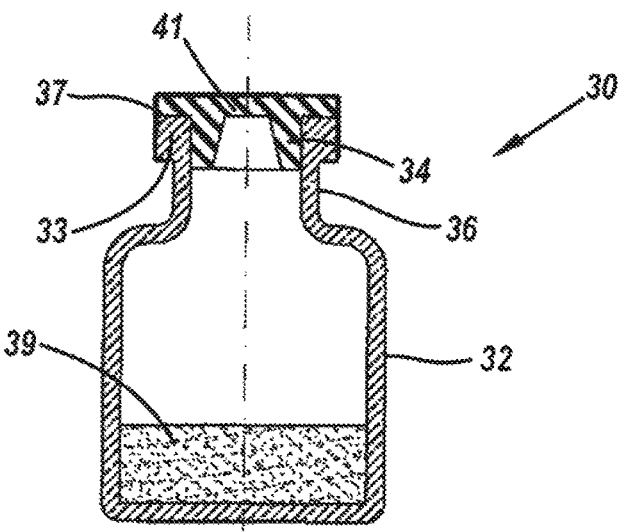
FIG. 1A (prior art)
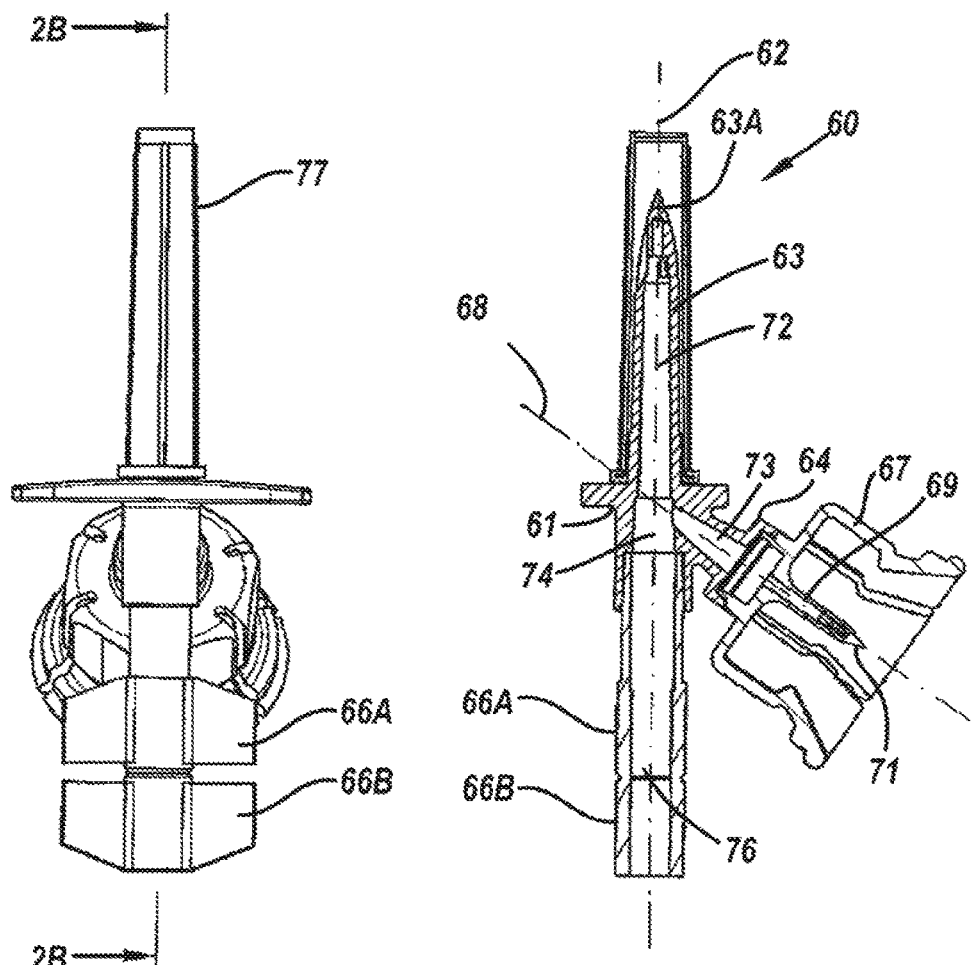
FIG. 2A (prior art)
FIG. 2B (prior art)

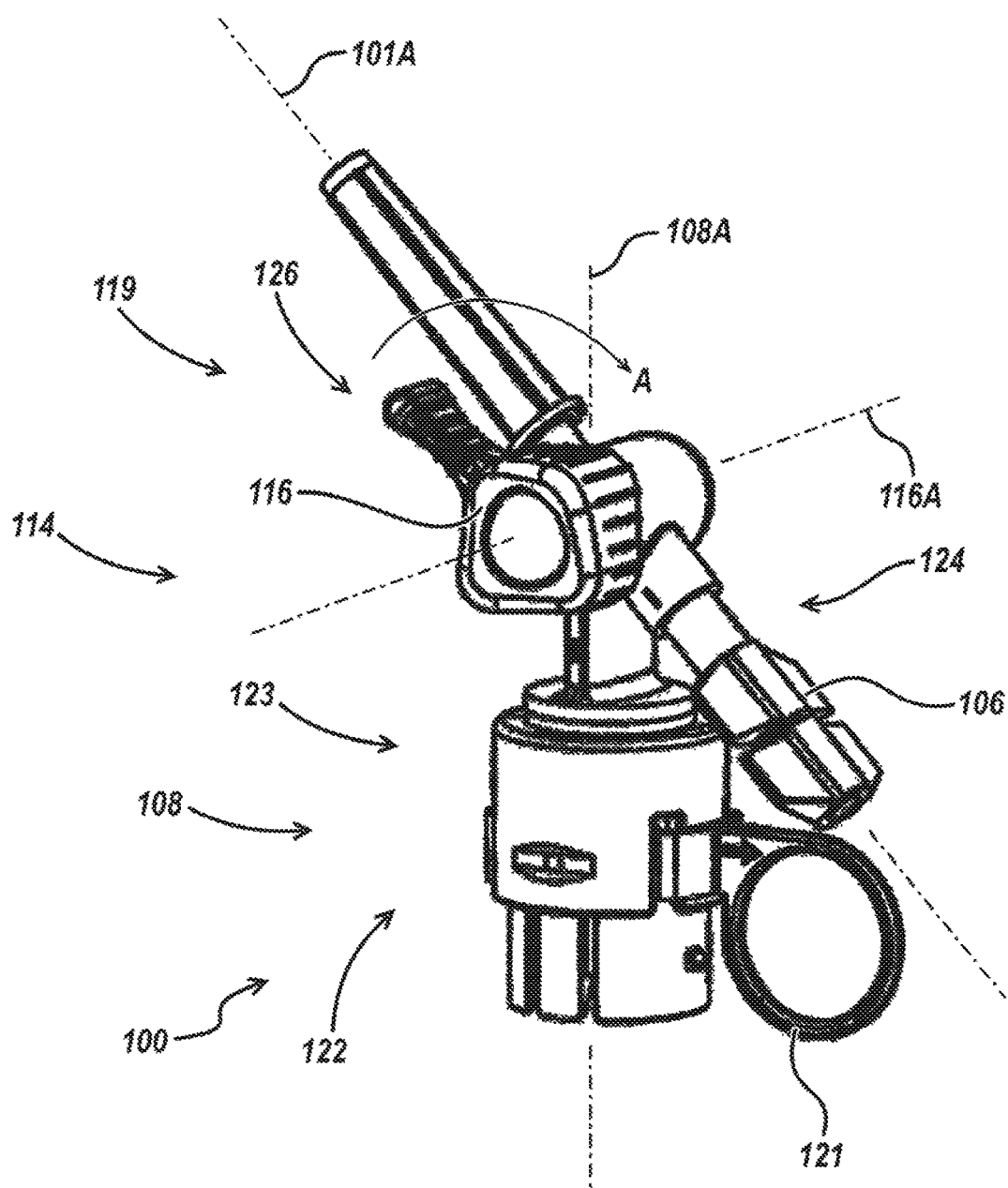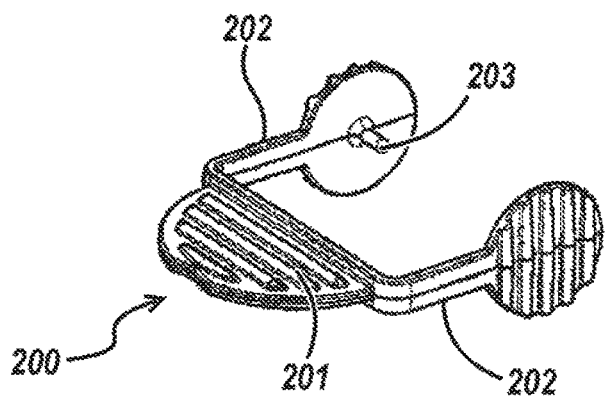
FIG. 3

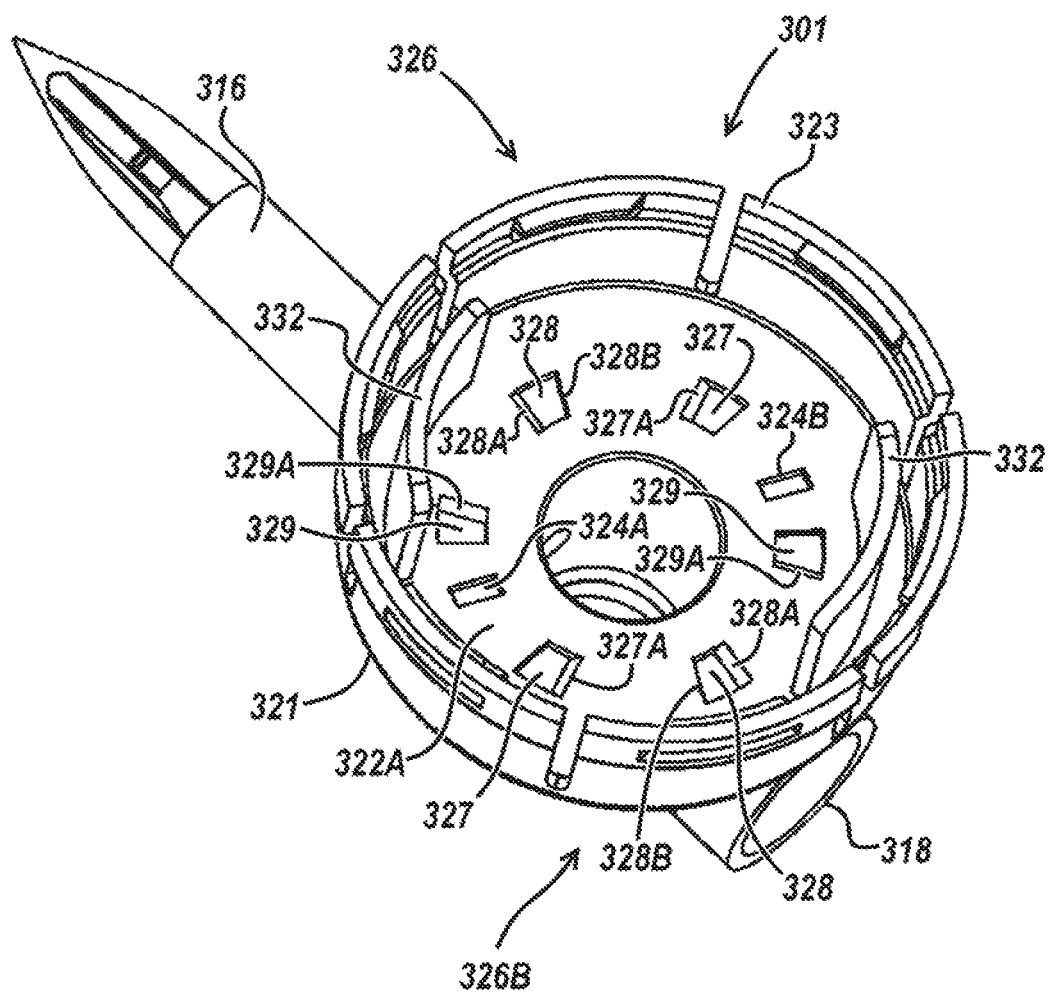

SECTION A-A

FIG. 19A
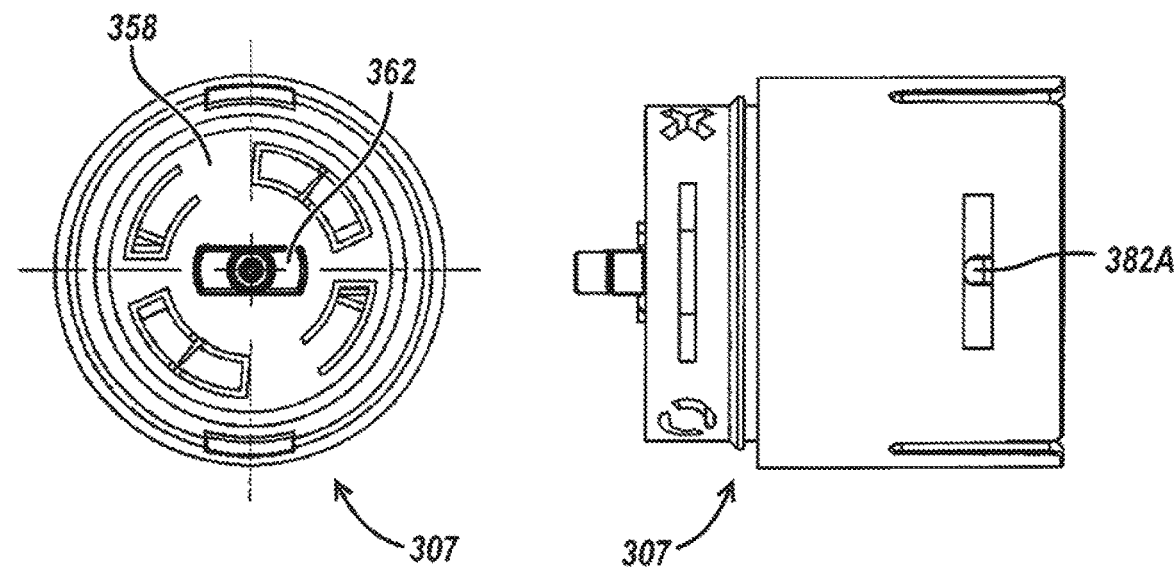
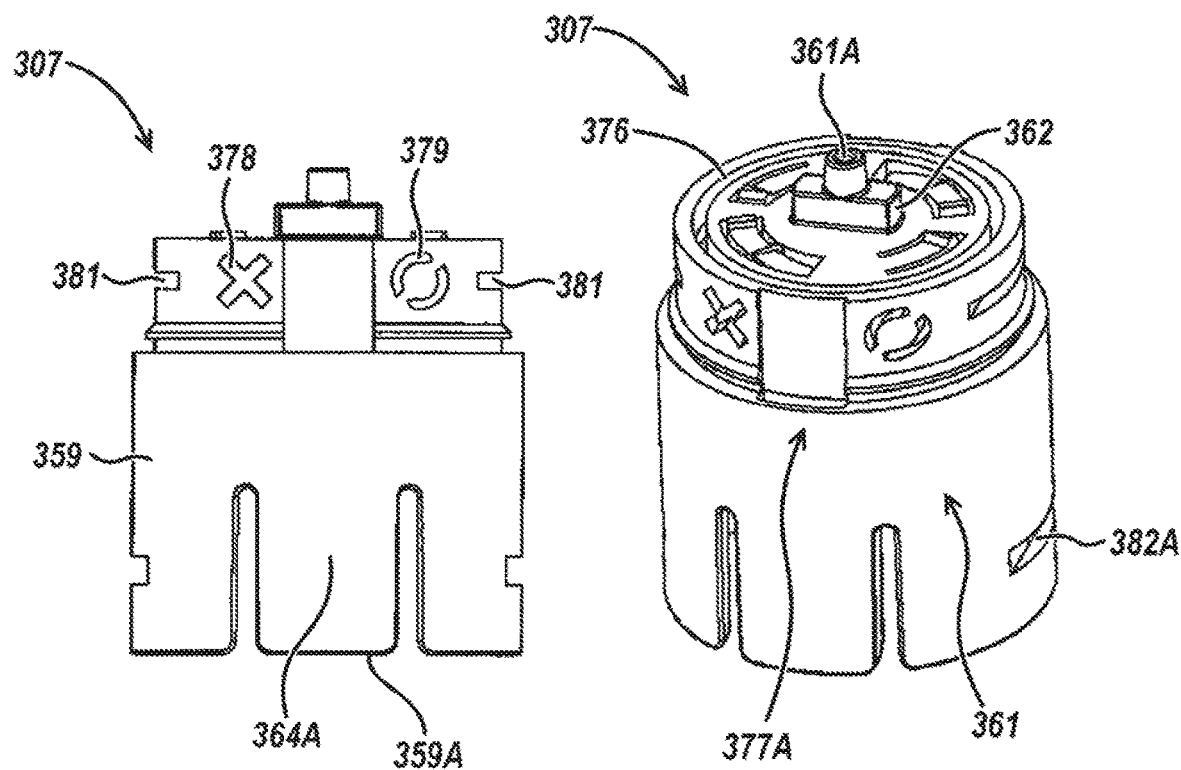

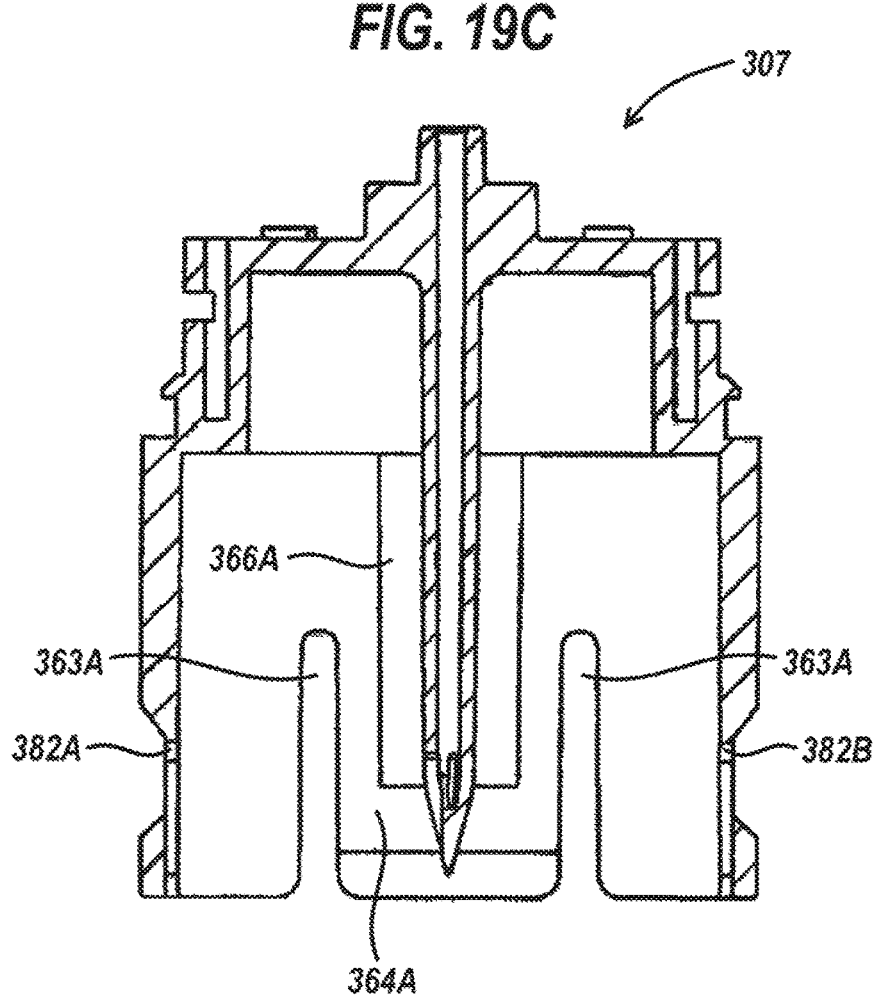
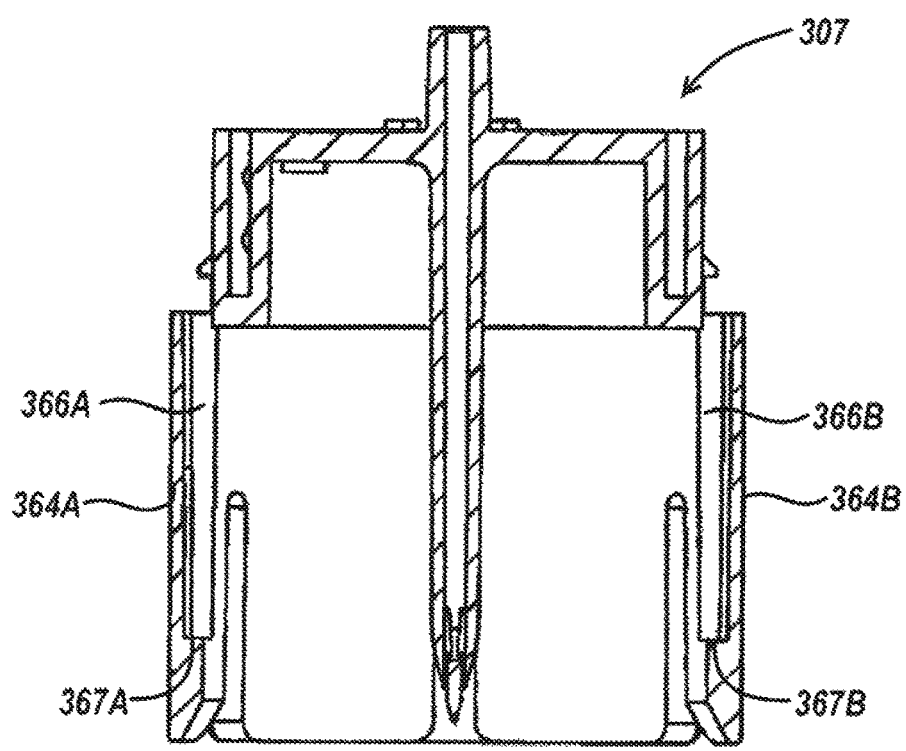
FIG. 19C

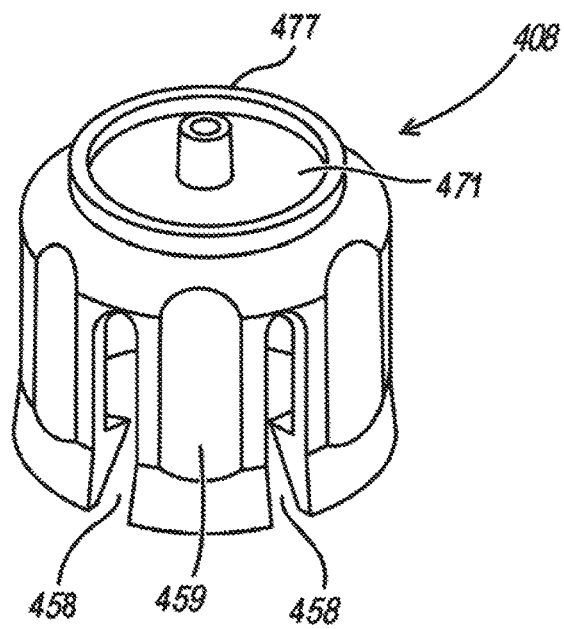
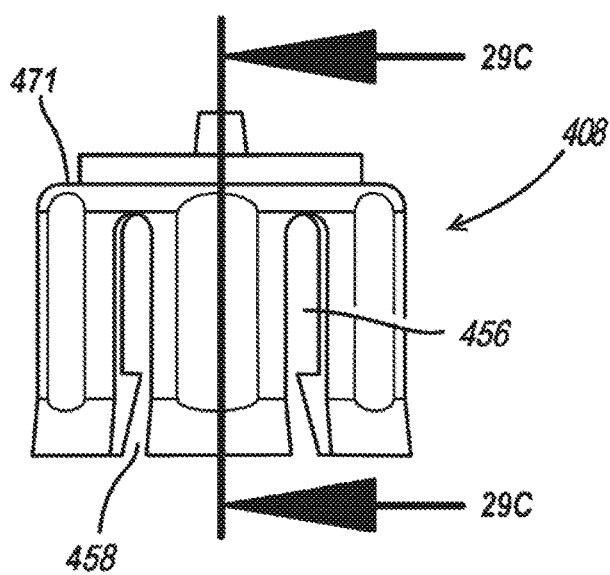
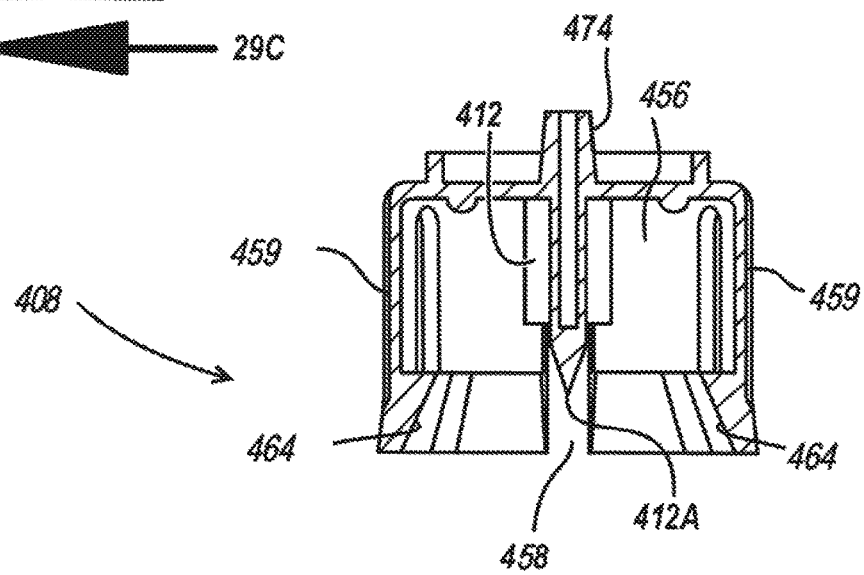

LIQUID TRANSFER DEVICE WITH TELESCOPIC VIAL ADAPTER FOR USE WITH INFUSION LIQUID CONTAINER AND DISCRETE INJECTION VIAL

CROSS-REFERENCE TO RELATED APPLICATIONS

This application is a section 371 of International Application No. PCT/IB18/59577, filed Dec. 3, 2018, which was published on Jun. 6, 2019 under International Publication No. WO 2019/106642 A1, which claims priority from Israeli Application No. 260220, filed on Jun. 24, 2018 and Israeli Application No. 256074, filed on Dec. 3, 2017, the entire contents of these applications are incorporated herein by reference in their entirety.

FIELD OF THE INVENTION

The invention relates to medical devices in general and liquid transfer devices for use with infusion liquid containers and discrete injection vials in particular.

BACKGROUND OF THE INVENTION

Commonly owned WIPO International Application No. PCT/IL2014/050680 entitled Liquid Transfer Devices for Use with Infusion Liquid Containers and published under WIPO International Publication No. WO 2015/019343 (incorporated by reference in its entirety herein) discloses liquid transfer devices for use with an infusion liquid container and a discrete injection vial for assisting preparation of an infusion liquid container with a medicated infusion liquid for administration to a patient. The infusion liquid containers can be in the form of an infusion bag, an infusion bottle, and the like. The infusion liquid containers contain an infusion liquid and have an intravenous (IV) or administration port. WO 2015/019343's FIG. 4 and FIG. 5 show a liquid transfer device hereinafter referred to as the WO 2015/019343 liquid transfer device, WO 2015/019343's FIG. 6 shows another liquid transfer device and WO 2015/019343's FIG. 7 shows yet another liquid transfer device.

The WO 2015/019343 liquid transfer device includes a trifurcated connector body having an IV spike for sealing insertion into an IV port, a vial adapter port with an integral vial adapter for snap fit telescopic mounting on an injection vial for flow communication therewith, and a twist-off substitute IV port. The twist-off substitute IV port includes a septum which is initially sealed prior to being punctured on insertion of an IV spike of an infusion set. The IV spike has a single lumen, the vial adapter port has a single lumen and the twist-off substitute IV port has a single lumen. The three lumens are in 3 way direct and continuous fluid connection such that preparation of an infusion liquid container with a medicated infusion liquid includes the following steps:

Step 1: snap fit telescopic mounting a liquid transfer device's vial adapter onto a discrete injection vial.

Step 2: inserting the liquid transfer device's IV spike into an infusion liquid container's IV port for establishing an immediate flow path between the infusion liquid container and the discrete injection vial.

Step 3: repeated forward and backward transfer of liquid contents from the infusion liquid container to the discrete injection vial to mix or reconstitute the injection vial's medicament to form medicated infusion liquid in the infusion liquid container.

Step 4: opening the liquid transfer device's substitute IV port and inserting an infusion set's IV spike thereinto for establishing immediate flow path between the infusion liquid container and the infusion set ready for gravitational flow of medicated infusion liquid from the infusion liquid container to a patient.

Further facilitating administration of medicated infusion liquids would be additionally advantageous.

SUMMARY OF THE INVENTION

The present invention is directed towards liquid transfer devices similar to the aforementioned WO 2015/019343 liquid transfer device. The liquid transfer devices of the present invention differ from the former as follows: The liquid transfer device includes a rotation position stopcock arrangement (i.e. a flow control member) for controlling flow communication between its IV spike, vial adapter and twist-off substitute IV port in the vial adapter. The liquid transfer device includes an integral telescopic vial adapter, snap fit, telescopically mountable on a discrete injection vial while leaving the injection vial stopper non-punctured until a subsequent compaction is performed. The liquid transfer device may include a latch mechanism for preventing rotation of the three rotation position stopcock arrangement in the integral telescopic vial adapter's pre-compacted state. The integral telescopic vial adapter includes a safety catch mechanism for precluding inadvertent compaction from a pre-compacted state to a compacted state. The safety catch mechanism requires a user release action to release same. The user release action preferably includes removal of a safety catch. Commonly owned Israel Patent Application No. 251458, published as WO 2018/178971 A1 (incorporated by reference in its entirety herein), entitled User Activated Liquid Drug Transfer Devices for use in Ready-To-Use (RTU) Liquid Drug Transfer Assemblages discloses an alternative safety catch mechanism. The integral telescopic vial adapter also includes a clamping arrangement for irreversibly clamping same in its compacted state. The liquid transfer devices of the present invention are not limited to a twist-off substitute IV port but can be equally fitted with, for example, a substitute IV port requiring the breaking of a frangible component for opening the substitute IV port for insertion of an infusion set's IV spike thereinto.

In a two position stopcock arrangement there are provided the following positions: A mixing (or reconstituting) position for enabling flow communication between an IV spike and a vial adapter port for preparing a medicated infusion liquid. An administering position for enabling flow communication between the IV spike and a substitute IV port for administering the medicated infusion liquid. There may be provided an additional position in which the IV spike is sealed (or flow communication between the IV spike, the vial adapter port and the substitute IV port is blocked) which is made available as an initial positon prior to the mixing position.

In a three position stopcock arrangement there are provided the following positions: An initial set-up position for sealing the IV spike. An intermediate preparation position for enabling flow communication between its IV spike and vial adapter port for preparing a medicated infusion liquid. A final administration position for enabling flow communication between its IV spike and its substitute IV port for administering the medicated infusion liquid. The three rotation position stopcock arrangement includes a L-shaped flow control member with a flow control shaft and a flow control lever for rotating the L-shaped flow control member about its axis of rotation. The flow control member follows standard practice that its flow control lever indicates a sealed port. The three rotation position stopcock arrangement enables unidirectional rotation from the initial set-up position to the final administration position via the intermediate preparation position. A healthcare provider may inadvertently omit preparation and rotate the three rotation position stopcock arrangement from its initial set-up position to its final administration position without stopping at the intermediate preparation position. Accordingly, the three rotation position stopcock arrangement enables rotation from the final administration position to the intermediate preparation position.

The liquid transfer devices preferably enable a non-punctured intact discrete injection vial to be readily detached from an integral telescopic vial adapter after snap fit telescopic mounting before the user compaction for puncturing its injection vial stopper as disclosed in commonly owned PCT/IL2017/050299 entitled Liquid Drug Transfer Devices For Use with Intact Discrete Injection Vial Release Tool and published under PCT International Publication No. WO 2018/104930 A1 (incorporated by reference in its entirety herein). Such detachment can prevent wastage of injection vials which might otherwise occur in case of early preparation of a medicated infusion liquid and a subsequent decision that the medicated infusion liquid is no longer required to be administered to a patient. Such detachment is preferably achieved by a pincers-like compression. The pincers-like compression can be effected by an intact discrete injection vial release tool having an opposite pair of inward directed protrusions. The intact discrete injection vial release tool can be configured as a pincers-like hand tool or a user-operated electromechanical apparatus. The use of an intact discrete injection vial release tool to detach non-punctured intact discrete injection vials as opposed to manual detachment enables only authorized healthcare providers to detach same.

The invention is defined in the appended claims.

BRIEF DESCRIPTION OF DRAWINGS

In order to understand the invention and to see how it can be carried out in practice, a preferred embodiment will now be described, by way of a non-limiting example only, with reference to the accompanying drawings in which similar parts are likewise numbered, and in which:

FIG. 1A is a longitudinal cross section of the discrete injection vial along a cross section line 1A-1A in FIG. 1;

FIG. 2A is a top plan view of the WO 2015/019343 liquid transfer device;

FIG. 2B is a longitudinal cross section of the WO 2015/019343 liquid transfer device along a cross section line 2B-2B in FIG. 2A;

FIG. 3 is a front perspective view of a liquid transfer device according to a first embodiment of the invention including a telescopic vial adapter in a pre-compacted state and a pincers-like hand tool for releasing the non-punctured intact discrete injection vial from the telescopic vial adapter;

FIG. 16C is a bottom perspective view of the FIG. 16A IV spike body;

FIG. 19A illustrates different views of an outer vial adapter body of the FIG. 14 liquid transfer device;

FIG. 19C illustrates longitudinal cross sections of the FIG. 19A outer vial adapter body;

FIG. 29A is a top perspective view of a vial adapter body of the FIG. 25 liquid transfer device;

FIG. 29B illustrates a front elevation view and a longitudinal cross section of the vial adapter body;

FIG. 29C illustrates a side elevation view and a longitudinal cross section of the vial adapter body;

DETAILED DESCRIPTION OF DRAWINGS

Figure 1:
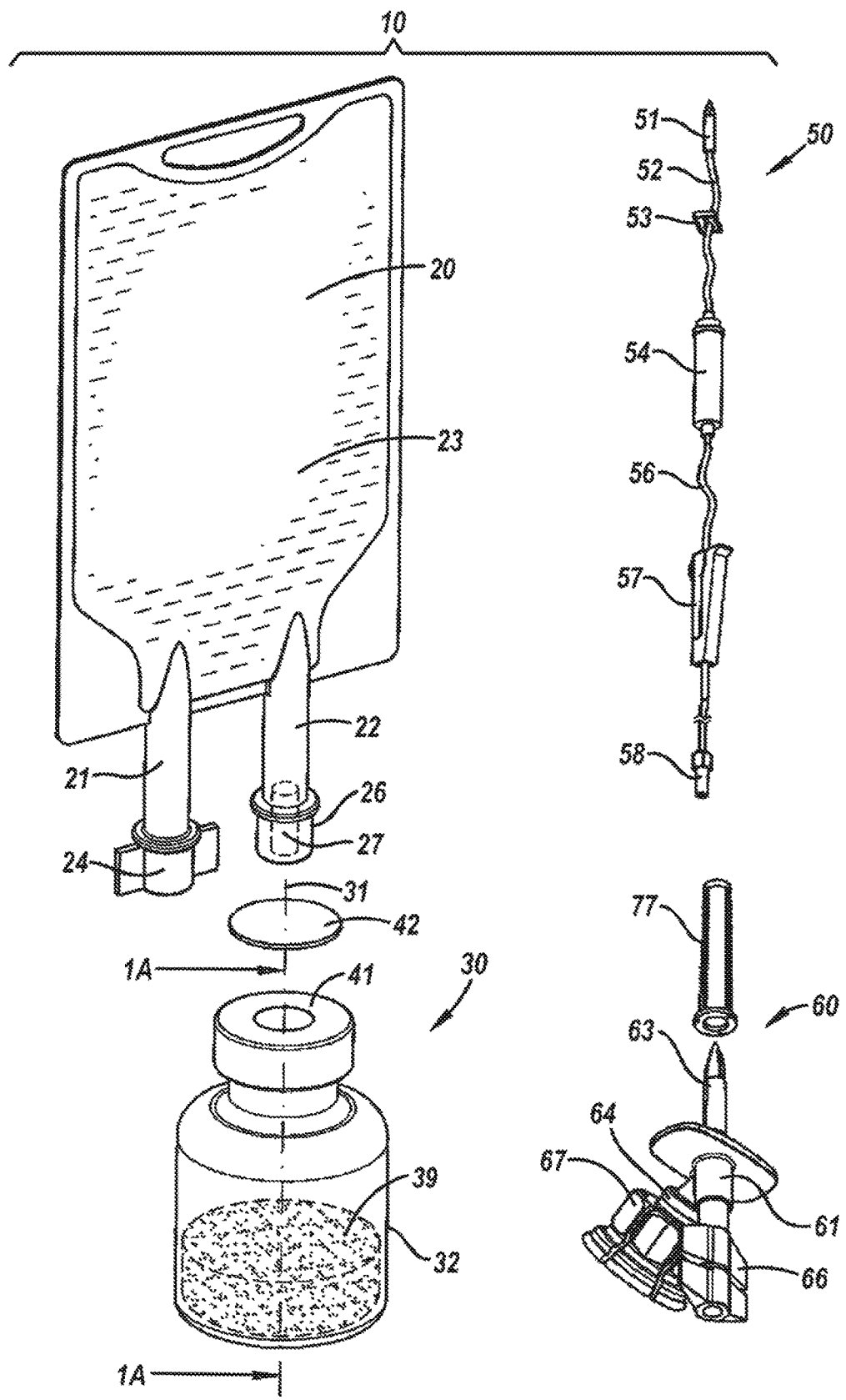
FIG. 1 is a pictorial view of a conventional administration set including an infusion bag, the WO 2015/019343 liquid transfer device, a discrete injection vial, and an infusion set.
Figure 4:
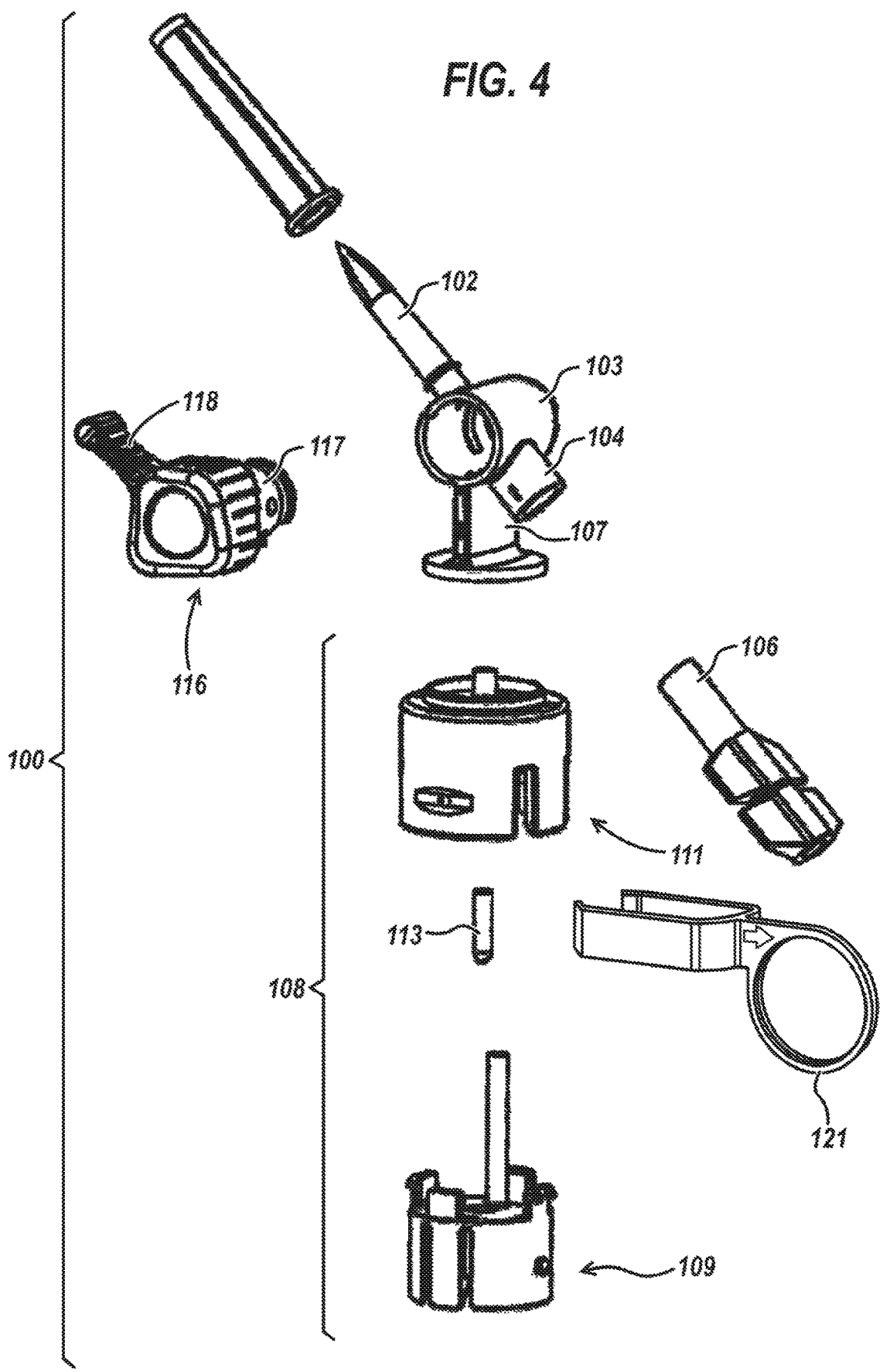
FIG. 4 is an exploded view of the FIG. 3 liquid transfer device.
Figure 5A:
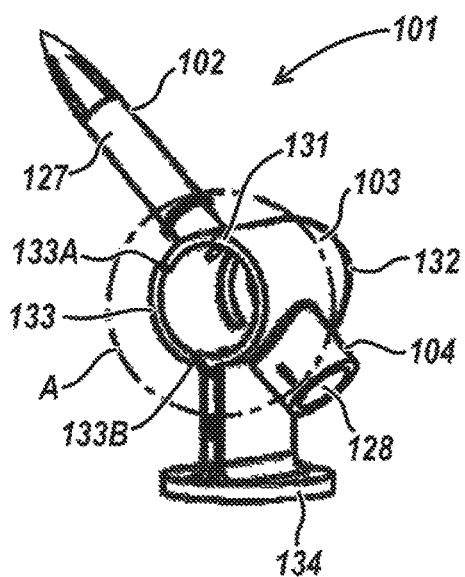
FIG. 5A is a top perspective view of an IV spike body of the FIG. 3 liquid transfer device.
Figure 5B:
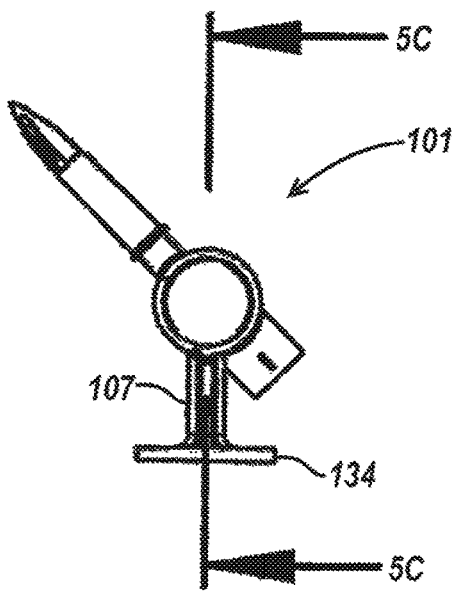
FIG. 5B is a top plan view of the IV spike body.
Figure 5C:
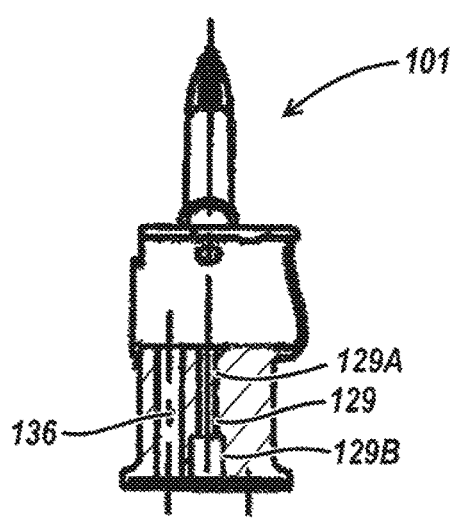
FIG. 5C is a longitudinal cross section of the IV spike body along line 5C-5C in FIG. 5B.
Figure 5D:
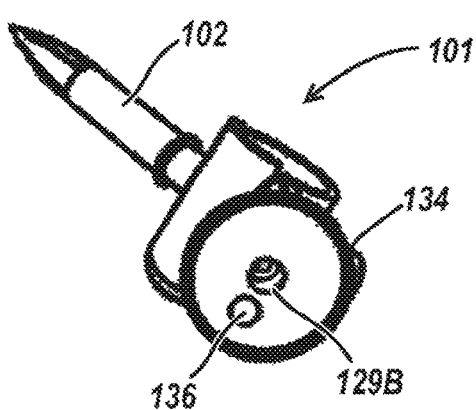
FIG. 5D is a bottom perspective view of the IV spike body.
Figure 5E:
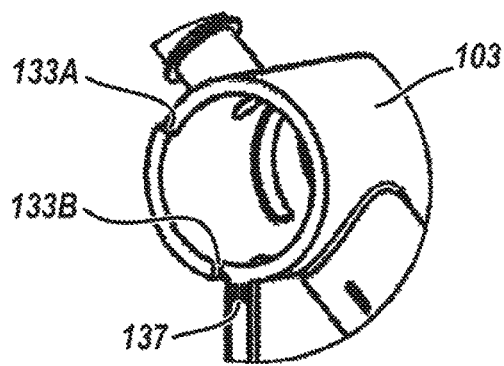
FIG. 5E is a close-up view of a feature of the IV spike body encircled A in FIG. 5A.
Figure 6A:
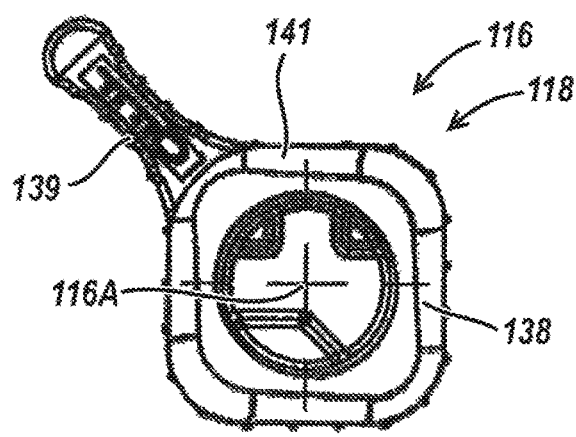
FIG. 6A is a top plan view of a flow control member of the FIG. 3 liquid transfer device.
Figure 6B:
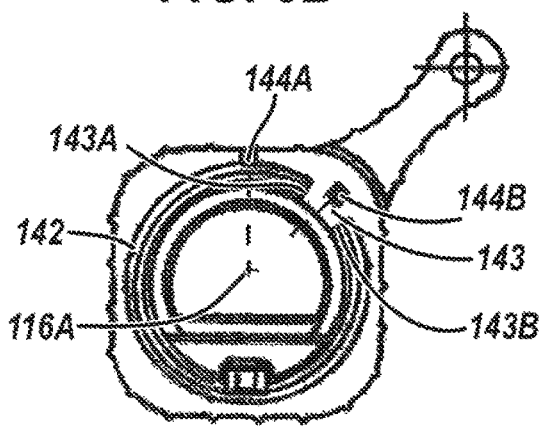
FIG. 6B is a bottom plan view of the flow control member.
Figure 6C:
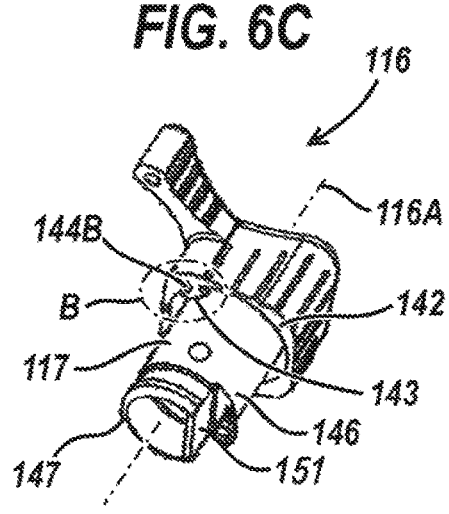
FIG. 6C is a bottom perspective view of the flow control member.
Figure 6D:
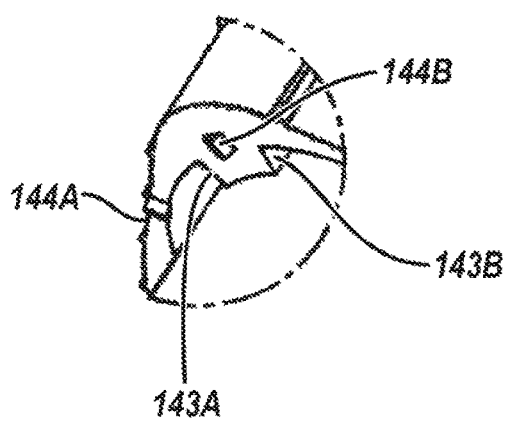
FIG. 6D is a close-up view of a feature of the flow control member encircled B in FIG. 6C.
Figure 6E:
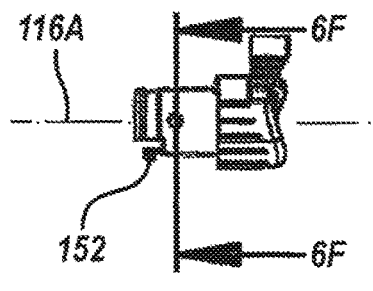
FIG. 6E is a side elevation view of the flow control member.
Figure 6F:
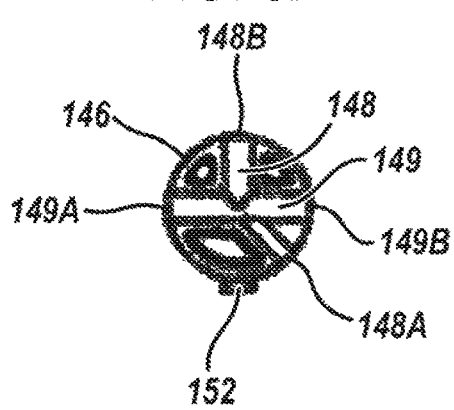
FIG. 6F is a transverse cross section of the flow control member in FIG. 6E.

Certain terminology is used in the following description for convenience only and is not limiting. For example, the words "lower," "bottom," "upper" and "top" designate directions in the drawings to which reference is made. The words "inwardly," "outwardly," "upwardly" and "downwardly" refer to directions toward and away from, respectively, the geometric center of the described device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

FIG. 1 shows an administration set 10 including an infusion liquid container 20, an initially non-punctured intact discrete injection vial 30, an infusion set 50, and a WO 2015/019343 liquid transfer device 60. The infusion liquid container 20 is constituted by an intravenous (IV) bag having an IV or administration port 21 and an injection port 22 and containing an infusion liquid 23. The IV port 21 is sealed by a twist-off cap 24 for insertion of an IV spike for administration purposes. The injection port 22 terminates in an injection port tip 26 with a seal-sealing plug 27 intended for needle insertion of syringe contents into the IV bag 20.

FIG. 1A shows the discrete injection vial 30 has a longitudinal injection vial centerline 31 and includes a closed end vial tube 32, a tubular vial crown 33 having a crown opening 34 and a vial neck 36 intermediate the vial tube 32 and the vial crown 33. The injection vial 30 includes an injection vial stopper 37 for hermetically sealing the crown opening 34. The vial crown 33 is capped by a band 38. The injection vial 30 contains a medicament 39 for introduction into the infusion liquid 23 to form a medicated infusion liquid. The medicament 39 can be in solid form, powder form or liquid form. The injection vial 30 has an uppermost injection vial surface 41 which is sterilized before accessing the injection vial 30 for forming a medicated infusion liquid. The injection vial 30 includes a flip-off tamper evidence cap 42 which is removed immediately before use to expose the uppermost injection vial surface 41. The tamper evidence cap 42 is intended to be single use such that it cannot be replaced after removal. The injection vial 30 is still regarded as being intact notwithstanding that its flip-off tamper evidence cap 42 has been removed and it not replaceable. The injection vial 30 is intact in the sense that its injection vial stopper 37 has not been fully punctured therethrough for establishing flow communication with its interior.

The infusion set 50 includes an IV spike 51 and additionally includes first tubing 52, a clamp 53, a drip chamber 54, second tubing 56, a roller clamp 57, and a male Luer connector 58.

FIG. 1, FIG. 2A and FIG. 2B show the WO 2015/019343 liquid transfer device 60 includes a trifurcated Y-shaped connector body 61 having a longitudinal connector body centerline 62, an IV spike 63 for sealing insertion into the IV port 21, a vial adapter port 64, and a twist-off substitute IV port 66. The IV spike 63 has an IV spike tip 63A. The vial adapter port 64 has an integral vial adapter 67 with a vial adapter centerline 68 intercepting the longitudinal connector body centerline 62. The vial adapter 67 has a puncturing cannula 69 with a puncturing cannula tip 71. The connector body 61 has a lumen 72 terminating at the IV spike 63, a lumen 73 in flow communication with the puncturing cannula 69 and a lumen 74 terminating at the substitute IV port 66. The three lumens 72, 73 and 74 are in three way direct and continuous fluid connection. The substitute IV port 66 is formed from suitable flexible plastic material, for example, PVC, and the like, for sealing receiving the IV spike 51. The substitute IV port 66 includes a septum 76 intended to be punctured on insertion of the IV spike 51. The substitute IV port 66 includes a proximal section 66A and a distal section 66B. In use, the distal section 66B is twisted and broken off from the proximal section 66A thereby exposing the septum 76 for puncturing by the infusion set's IV spike 51. The liquid transfer device 60 can include an IV spike cover 77 to protect the IV spike 63.

FIG. 3 to FIG. 8C show a liquid transfer device 100 in accordance with a first embodiment of the invention, having a different construction and operation from the WO 2015/109343 liquid transfer device 60. FIG. 3 also shows a pincers-like hand tool 200 for releasing a non-punctured intact discrete injection vial 30. The pincers-like hand tool 200 includes a pincers-like body 201 with an opposite pair of jaws 202 each terminating at an inward directed protrusion 203. The opposite pair of jaws 202 can be readily manually urged towards one another for applying a pincers-like compression for releasing a non-punctured intact discrete injection vial 30 as described hereinbelow with reference to FIG. 10A and FIG. 10B.

The liquid transfer device 100 includes a trifurcated Y-shaped IV spike body 101 with a longitudinal IV spike body centerline 101A, a leading IV spike 102, a central flow control member port 103 and a trailing substitute IV port holder 104 for sealingly receiving a substitute IV port 106. The flow control member port 103 has a flow control member port axis 103A transverse to the longitudinal IV spike body centerline 101A. The substitute IV port 106 can be implemented as a twist off component, a break off component, and the like. The IV spike 102 and the substitute IV port holder 104 are co-directional along the longitudinal IV spike body centerline 101A. The IV spike body 101 includes a vial adapter support 107 extending from the central flow control member port 103 and subtending an included approximately 135° angle with the IV spike 102 and a complementary included approximately 45° angle with the substitute IV port 104 in the FIG. 3 top perspective view. The liquid transfer device 100 includes a telescopic vial adapter 108 mounted on the vial adapter support 107. The telescopic vial adapter 108 may be rigidly and permanently mounted on the vial adapter support 107 or removably mounted on the vial adapter support 107. The telescopic vial adapter 108 has a longitudinal vial adapter centerline 108A intercepting the longitudinal IV spike body centerline 101A. The telescopic vial adapter 108 includes an inner vial adapter body 109 and an outer vial adapter body 111 and is intended to undergo compaction from an initial pre-compacted state to a final compacted state in which the outer vial adapter body 111 slidingly receives the inner vial adapter body 109 therein. The telescopic vial adapter 108 includes a puncturing cannula 112 (see FIG. 8A to FIG. 8C) for selectively puncturing the injection vial stopper 37 in its compacted state. The puncturing cannula 112 is protected by a thin sheath 113 for maintaining sterility until use of the liquid transfer device 100 for administering a medicated infusion liquid.

The liquid transfer device 100 includes a hand operated three rotation position stopcock arrangement 114 having a L-shaped flow control member 116 for clockwise rotation relative to the IV spike body 101 as denoted by arrow A in the FIG. 3 top perspective view. The flow control member 116 has an axis of rotation 116A perpendicular to the longitudinal IV spike body centerline 101A and passing therethrough. The flow control member 116 includes a flow control shaft 117 securely and sealingly inserted in the flow control member port 103 and a flow control lever 118 intended to be gripped between a healthcare provider's thumb and forefinger for rotating same. The hand operated three rotation position stopcock arrangement 114 controls flow communication of the liquid transfer device 100 in the telescopic vial adapter 108's compacted state. The hand operated three rotation position stopcock arrangement 114 involves clockwise rotation of the flow control member 116 in the FIG. 3 top perspective view from an initial set-up position to a final administration position for administering medicated infusion liquid to a patient via an intermediate preparation position for preparing medicated infusion liquid. The three rotation position stopcock arrangement 114 seals the IV spike 102 in the initial set-up position, the substitute IV port 106 in the intermediate administration position, and the telescopic vial adapter 108 in the final administration position.

The liquid transfer device 100 includes the following features: A safety catch mechanism 119 for preventing inadvertent user compaction of the telescopic vial adapter 108 from an initial pre-compacted state to a final compacted state. The safety catch mechanism 119 is implemented as a tuning fork-like safety catch 121 transversely extending through the outer vial adapter body 111 in the telescopic vial adapter 108's initial pre-compacted state. A clamping arrangement 122 for irreversibly clamping the telescopic vial adapter 108 in its compacted state. A latch mechanism 123 for preventing operation of the hand operated three rotation position stopcock arrangement 114 in the telescopic vial adapter 108's pre-compacted state. A stopcock rotation limit arrangement 124 for stopping a healthcare provider from further rotation of the flow control member 116 beyond the final administration position. A detent arrangement 126 for issuing audible alerts on rotating the flow control member 116 to its intermediate preparation position from its initial set-up position and to its final administration position from its intermediate preparation position. The audible alerts are preferably in the form of clicks by the snap click engagement of a detent into a detent groove such that a healthcare provider hears two clicks during the operation of the liquid transfer device 100. Accordingly the detent arrangement 126 can include a single detent groove and a pair of detents or alternatively a single detent and a pair of detent grooves.

FIG. 5A to FIG. 5E show the IV spike 102 has an IV spike lumen 127 in flow communication with the flow control member port 103 and its substitute IV port holder 104 has a substitute IV port holder lumen 128 co-linear with the IV spike lumen 127 and in flow communication with the flow control member port 103. The vial adapter support 107 includes a vial adapter support lumen 129 in flow communication with the flow control member port 103. The vial adapter support lumen 129 has a stepped configuration including a narrow diameter major vial adapter support lumen section 129A proximate the flow control member port 103 and a wide diameter minor vial adapter support lumen section 129B remote from the flow control member port 103.

The central flow control member port 103 includes a leading flow control member port rim 131 and an opposite trailing flow control member port rim 132. The leading flow control member port rim 131 has a stepped configuration constituting a component of the stopcock rotation limit arrangement 124. The leading flow control member port rim 131 includes a raised arc section 133 having an approximately 135° arc length thereby limiting rotation of the flow control member 116 about its axis of rotation 116A to approximately 225° from its initial set-up position to its final administration position. The raised arc section 133 has a raised arc section wall 133A and an opposite raised arc section wall 133B.

The vial adapter support 107 terminates in a vial adapter flange 134 for mounting on the telescopic vial adapter 108. The vial adapter support 107 includes a throughgoing latch bore 136 constituting a component of the latch mechanism 123. The throughgoing latch bore 136 extends from the flow control member port 103 to the vial adapter flange 134. The detent arrangement 126 includes a detent groove 137 on the vial adapter support 107 adjacent the leading flow control member rim 131 and before the raised arc section wall 133B.

FIG. 6A to FIG. 6F show the flow control lever 118 has a generally square shaped major flow control lever section 138 and an elongated minor flow control lever section 139 for being gripped between a healthcare provider's thumb and forefinger. The flow control lever 118 has a top flow control lever surface 141 facing away from the flow control member port 103 having insignia for indicating an operative flow path of the liquid transfer device 100, namely, a preparation flow path between the IV spike 102 and the telescopic vial adapter 108 or an administration flow path between the IV spike 102 and the substitute IV port 106. The top flow control lever surface 141 bears the word OFF for indicating a sealed port to a healthcare provider in accordance with standard practice of three position rotation stopcocks.

The generally square shaped major flow control lever section 138 has a flow control lever rim 142 facing the flow control member port 103 and surrounding the flow control shaft 117. The flow control lever rim 142 has an inward directed projection 143 constituting a component of the stopcock rotation limit arrangement 124. The inward directed projection 143 has an inward directed projection wall 143A for abutting against the raised arc section wall 133A for preventing anti-clockwise rotation of the flow control member 116 relative to the IV spike body 101 in the FIG. 3 top perspective view. The inward directed projection 143 has an opposite inward directed projection wall 143B for abutting against the raised arc section wall 133B for stopping the flow control member 116's clockwise rotation in the FIG. 3 top perspective view at the flow control member 116's final administration position.

The flow control lever rim 142 is provided with a detent pair of the detent arrangement 126 as follows: a first detent 144A for snap fitting into the detent groove 137 at the flow control member 116's intermediate preparation position and a second detent 144B for snap fitting into the detent groove 137 at the flow control member 116's final administration position. The second detent engagement is before abutment of the opposite inward directed projection wall 143B against the raised arc section wall 133B. The detent pair 144 subtend an included approximately 45° angle corresponding to the angle of rotation from the flow control member 116's intermediate preparation position to its final administration position.

The flow control shaft 117 has a flow control shaft peripheral surface 146 and a flow control shaft end surface 147 opposite the flow control lever 118. The flow control shaft 117 includes an angled preparation lumen 148 for flow communication between the IV spike lumen 127 and the vial adapter support lumen 129 and a straight administration lumen 149 for flow communication between the IV spike lumen 127 and the substitute IV port holder lumen 128 midway therealong. The preparation lumen 148 and the administration lumen 149 are deployed on the same transverse plane and intercept at the axis of rotation 116A. The preparation lumen 148 includes a preparation lumen inlet aperture 148A and a preparation lumen outlet aperture 148B in the flow control shaft peripheral surface 146. The administration lumen 149 includes an administration lumen inlet aperture 149A and an administration lumen outlet aperture 149B in the flow control shaft peripheral surface 146. The angled preparation lumen 148 has an included approximately 135° angle equal to the included approximately 135° angle between the IV spike 102 and the vial adapter support 107.

The flow control shaft 117 includes a cutaway section 151 co-directional with the axis of rotation 116A towards the flow control shaft end surface 147. The flow control shaft 117 includes a cantilever-like latch stop 152 constituting a component of the latch mechanism 123. The latch stop 152 is deployed in the latch bore 136 in the flow control member's initial set-up position and intended to be flexed out therefrom towards the axis of rotation 116A on compaction of the telescopic vial adapter 108 thereby enabling manual rotation of flow control member 116. The latch stop 152 is diametrically opposite the detent 144A.

Figure 7A:
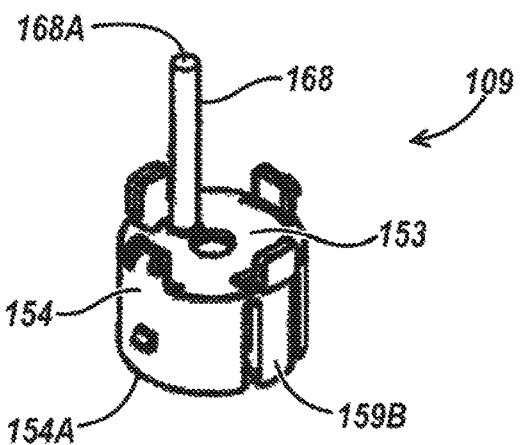
FIG. 7A is a top perspective view of an inner vial adapter body of the FIG. 3 liquid transfer device.
Figure 7B:
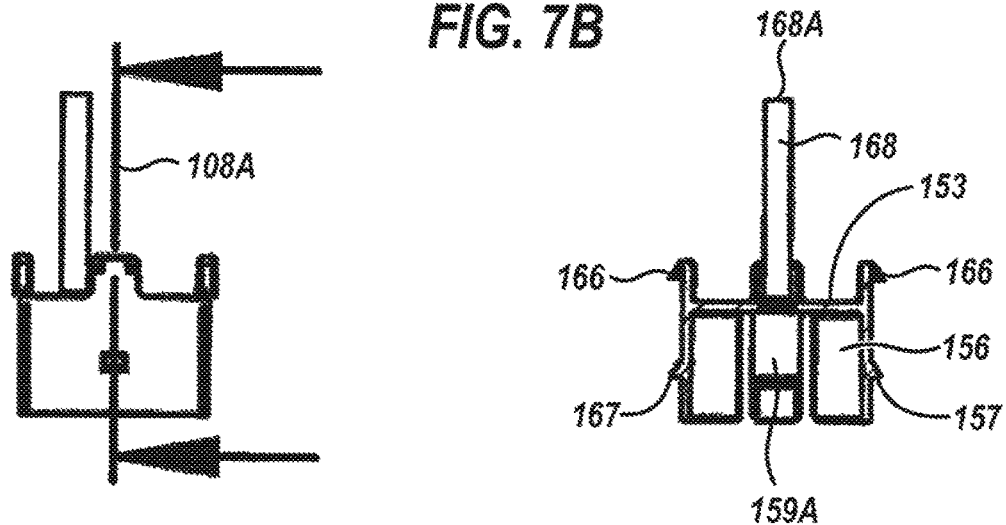
FIG. 7B illustrates a front elevation view and a longitudinal cross section of the inner vial adapter body.
Figure 7C:
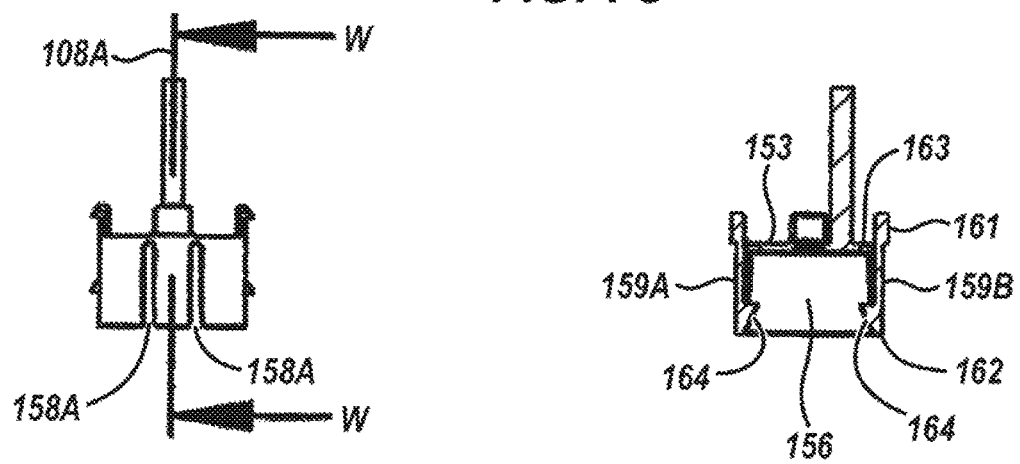
FIG. 7C illustrates a side elevation view and a longitudinal cross section of the inner vial adapter body.

FIG. 7A to FIG. 7C show the inner vial adapter body 109 has an inverted cup shape including an uppermost transverse annular inner vial adapter body wall 153 and a downward depending vial crown sleeve 154 with a lowermost vial crown sleeve rim 154A. The inner vial adapter body 109 bounds a vial crown cavity 156 for snugly receiving the vial crown 33 therein on telescopically snap fitting the inner vial adapter body 109 thereon. The uppermost transverse annular inner vial adapter body wall 153 has a center uppermost transverse annular inner vial adapter body wall throughgoing aperture 153A along the longitudinal vial adapter centerline 108A overlying the uppermost injection vial surface 41 on telescopically snap fitting on the discrete injection vial 30.

The vial crown sleeve 154 includes a major vial crown sleeve surround 157 with a first adjacent pair of longitudinal directed slits 158A and a second adjacent pair of longitudinal directed slits 158B for correspondingly forming a diametric pair of vial crown holding members 159A and 159B. The diametric pair of vial crown holding members 159 are pivotal with respect to the major vial crown sleeve surround 157 such that each vial crown holding member 159 has a proximal vial crown holding member section 161 and a distal vial crown holding member section 162. The uppermost transverse annular inner vial adapter body wall 153 preferably has a diametric pair of cutouts 163 inward of the diametric pair of vial crown holding members 159 such that the diametric pair of vial crown holding members 159 pivot on the uppermost transverse annular inner vial adapter wall 153.

The distal vial crown holding member sections 162 are each provided with a radial inward vial crown holding projection 164 towards the lowermost vial crown sleeve rim 154A for snap fitting under the vial crown 33 on telescopically snap fitting the inner vial adapter body 109 on the initially non-punctured intact discrete injection vial 30. Application of a pincers-like compression on the proximal vial crown holding member sections 161 towards the longitudinal vial adapter centerline 108A pivots the vial crown holding members 159 with respect to the major vial crown sleeve surround 157 thereby distancing the radial inward vial crown holding protrusions 164 from the longitudinal vial adapter centerline 108A.

The uppermost transverse annular inner vial adapter body wall 153 has a diametric pair of upright retaining members 166 correspondingly orthogonal to the diametric pair of vial crown holding members 159. The diametric pair of upright retaining members 166 prevent the inner vial adapter body 109 being inadvertently removed from the outer vial adapter body 111. The vial crown sleeve 154 includes a diametric pair of clamp members 167 towards the lowermost vial crown sleeve rim 154A and correspondingly orthogonal to the diametric pair of vial crown holding members 159. The diametric pair of upright retaining members 166 and the diametric pair of clamp members 167 constitute components of the clamping arrangement 122.

The uppermost transverse annular inner vial adapter wall 153 has an upright latch release member 168 constituting a component of the latch mechanism 123. The latch release member 168 has a free latch release member end face 168A. The latch release member 168 extends through the outer vial adapter body 111 for deployment in the latch bore 136. The free latch release member end face 168A is deployed in the latch bore 136 in the telescopic vial adapter 108's non-compacted state and is flush with the central flow control member port 103 in the telescopic vial adapter 108's compacted state. In the telescopic vial adapter 108's compacted state, the latch release member 168 urges the latch stop 152 from (i.e. out of) the latch bore 136 thereby releasing the latch mechanism 123.

Figure 8A:
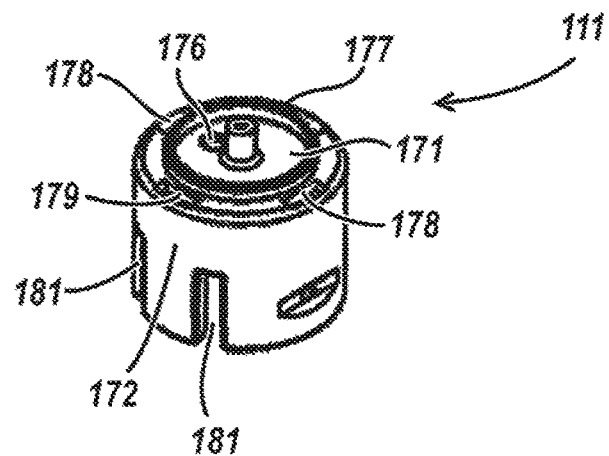
FIG. 8A is a top perspective view of an outer vial adapter body of the FIG. 3 liquid transfer device.
Figure 8B:
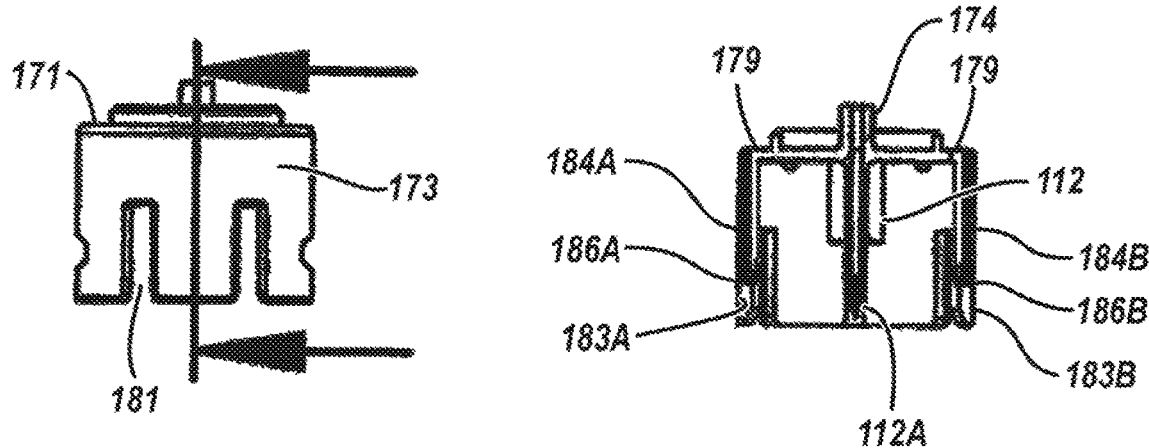
FIG. 8B are a front elevation view and a longitudinal cross section of the outer vial adapter body.
Figure 8C:
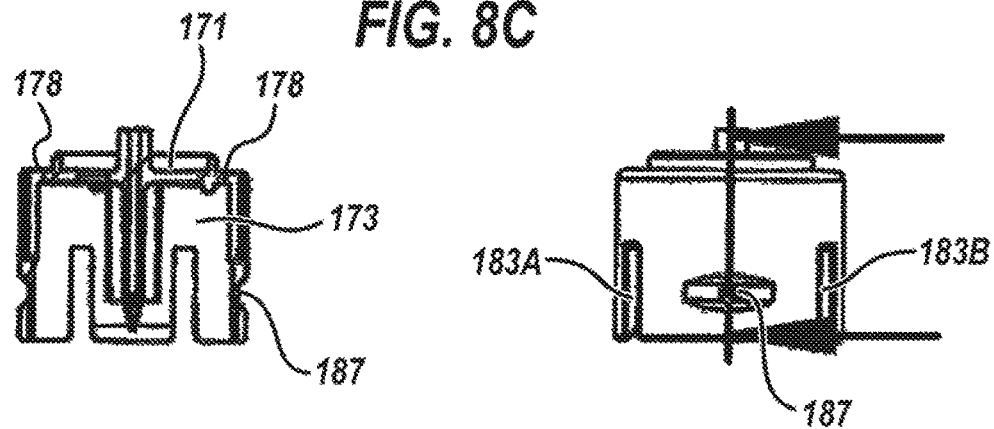
FIG. 8C are a side elevation view and a longitudinal cross section of the outer vial adapter body.
Figure 9A:
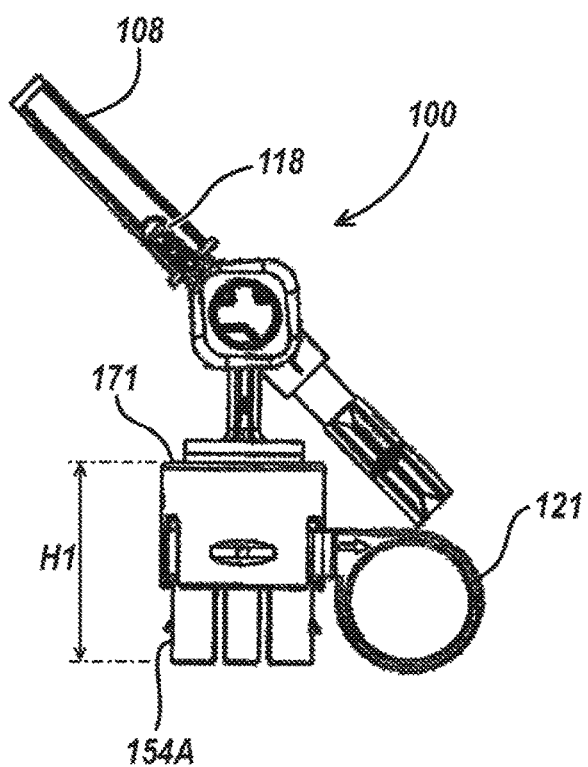
FIG. 9A is a front elevation view of the FIG. 3 liquid transfer device in an initial pre-compacted state.
Figure 9B:
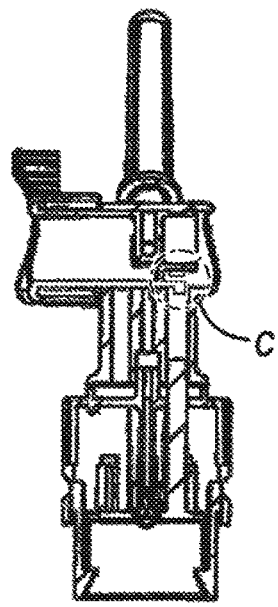
FIG. 9B is a longitudinal cross section of the liquid transfer device in FIG. 9A.
Figure 9C:
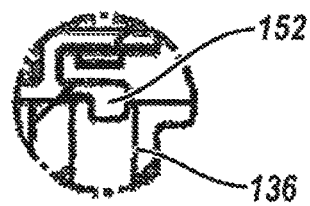
FIG. 9C is a close-up view of a feature of the liquid transfer device encircled C in FIG. 9B.
Figure 9D:
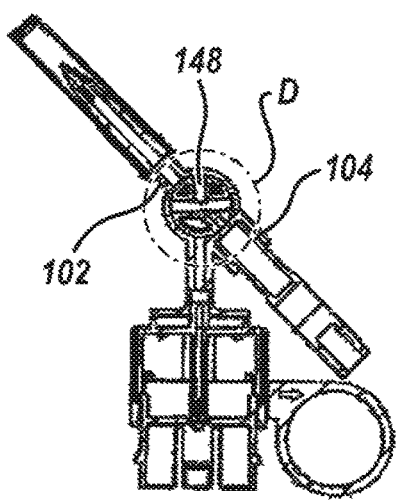
FIG. 9D is a longitudinal cross section of the liquid transfer device in FIG. 9B.
Figure 9E:
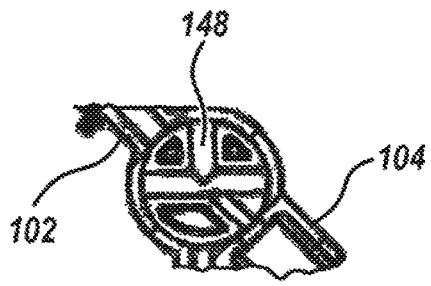
FIG. 9E is a close-up view of a feature of the liquid transfer device encircled D in FIG. 9D.

FIG. 8A to FIG. 8C show the outer vial adapter body 111 has an inverted cup shape including an uppermost transverse outer vial adapter body wall 171 and a downward depending outer vial adapter body skirt 172 with a lowermost outer vial adapter body skirt rim 172A The outer vial adapter body 111 bounds an inner vial adapter body cavity 173 for snugly telescopically receiving the inner vial adapter body 109 therein on compacting the telescopic vial adapter 108 from a pre-compacted state to a compacted state.

The uppermost transverse outer vial adapter body wall 171 includes the following features: First, a central upright connector 174 for insertion in the minor vial adapter support lumen section 129B and the opposite downward directed puncturing cannula 112. The puncturing cannula 112 has a distal puncturing cannula tip 112A for puncturing the injection vial stopper 37 in the telescopic vial adapter 108's compacted state. Second, a throughgoing aperture 176 in registration with the latch release member 168 for its passage therethrough. Third, a peripheral rim 177 for attachment to the vial adapter flange 134. Fourth, a diametric pair of peripheral slits 178 for receiving the diametric pair of the proximal vial crown holding member sections 161 in the telescopic vial adapter 108's compacted state. And fifth, a diametric pair of peripheral slits 179 for receiving the diametric pair of upright retaining members 166 in the telescopic vial adapter 108's compacted state.

The outer vial adapter body skirt 172 includes a first diametric pair of adjacent longitudinal slits 181 and a second diametric pair of adjacent longitudinal slits 182 opposite the first diametric pair of adjacent longitudinal slits 181 for correspondingly forming a diametric pair of inner vial adapter body holding members 183A and 183B. The tuning fork-like safety catch 121 transverses the first diametric pair of adjacent longitudinal slits 181 and the second diametric pair of adjacent longitudinal slits 182 for preventing compaction of the telescopic vial adapter 108.

The diametric pair of inner vial adapter holding members 183A and 183B have a diametric pair of internal longitudinal recesses 184A and 184B. The diametric pair of internal longitudinal recesses 184A and 184B correspondingly include a diametric pair of lowermost recess rims 186A and 186B. The diametric pair of inner vial adapter body holding members 183A and 183B constitute components of the clamping arrangement 122.

The outer vial adapter body skirt 172 has a diametric pair of throughgoing discrete injection vial release apertures 187 orthogonal to the diametric pair of inner vial adapter body holding members 183A and 183B. The diametric pair of discrete injection vial release apertures 187 are designed for use with the pincers-like hand tool 200 to apply a pincers-like compression for releasing a non-punctured intact injection vial 30 and preclude manual application of the pincers-like compression.

The use of the liquid transfer device 100 is now described with reference to FIG. 9A to FIG. 13B.

FIG. 9A to FIG. 9E show a set-up arrangement of the liquid transfer device 100 with the tuning fork-like safety catch 121 traversing the outer vial adapter body 111 for preventing compaction of the telescopic vial adapter 108. The flow control lever 118 indicates the IV spike 102 is sealed. The latch mechanism 123 latches the three rotation position stopcock arrangement 114 in its initial set-up position by way of the latch stop 152 deployed in the latch bore 136 (see FIG. 9C). The telescopic vial adapter 108 has a pre-compacted height H1 between the uppermost transverse outer vial adapter body wall 171 and the lowermost vial crown sleeve rim 154A. The diametric pair of discrete injection vial release apertures 188 are aligned with the diametric pair of proximal vial crown holding member sections 161.

Figure 10A:
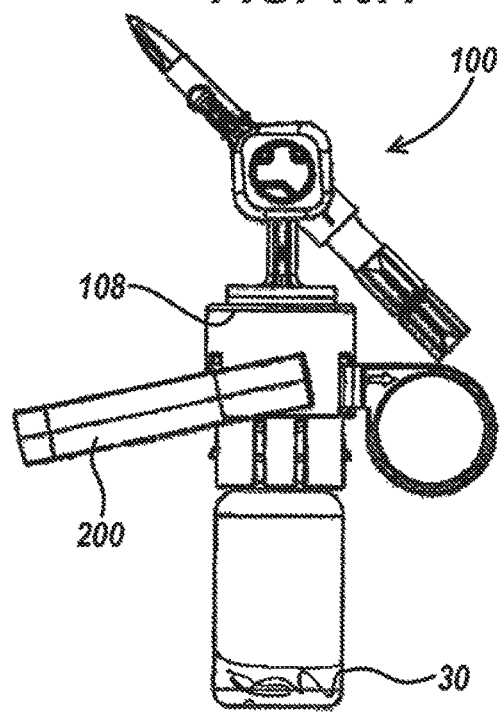
FIG. 10A is a front elevation view of the FIG. 3 liquid transfer device showing the use of the pincers-like hand tool for releasing the non-punctured intact discrete injection vial from the telescopic vial adapter.
Figure 10B:
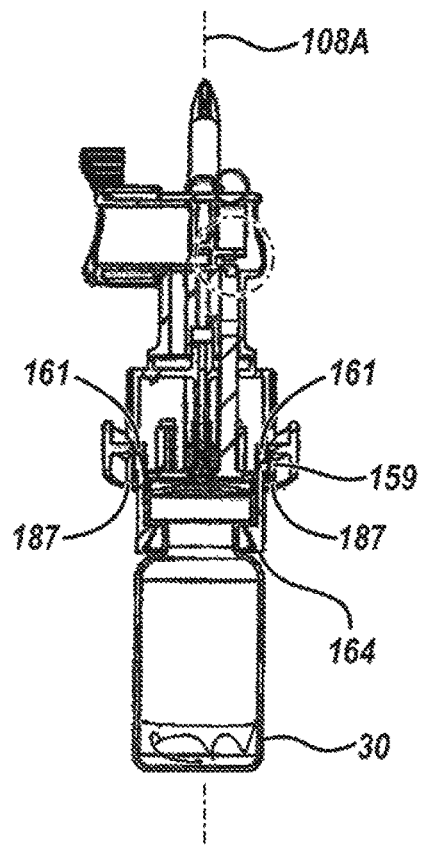
FIG. 10B is a longitudinal cross section of the liquid transfer device in FIG. 10A.

The healthcare provider removes the tamper evidence cap 42 from the non-punctured intact discrete injection vial 30 and wipes the exposed uppermost injection vial surface 41. The healthcare provider telescopically mounts the telescopic vial adapter 108 onto the injection vial 30 ready for preparation of medicated infusion liquid in the infusion liquid container 20 for subsequent administration to a patient. In the event it is decided not to administer the medicament and re-use the non-punctured intact discrete injection vial 30, a healthcare provider takes the following steps as shown in FIG. 10A and FIG. 10B:

The healthcare provider aligns the pincers-like hand tool 200 with the telescopic vial adapter 108 for inserting the opposite pair of inward directed protrusions 203 through the diametric pair of throughgoing discrete injection vial release apertures 187. The healthcare provider applies a pincers-like compression on the diametric pair of proximal vial crown holding member sections 161 for urging them towards the longitudinal vial adapter centerline 108A. The diametric pair of vial crown holding members 159 pivot with respect to the major vial crown sleeve surround 157 thereby distancing the diametric pair of radial inward vial crown holding projections 164 away from the longitudinal vial adapter centerline 108A to release the non-punctured intact discrete injection vial 30. The healthcare provider withdraws the non-punctured intact discrete injection vial 30 from the inner vial adapter body 109 for subsequent use notwithstanding that its tamper evidence cap 42 has been removed and discards the liquid transfer device 100.

Figure 11A:
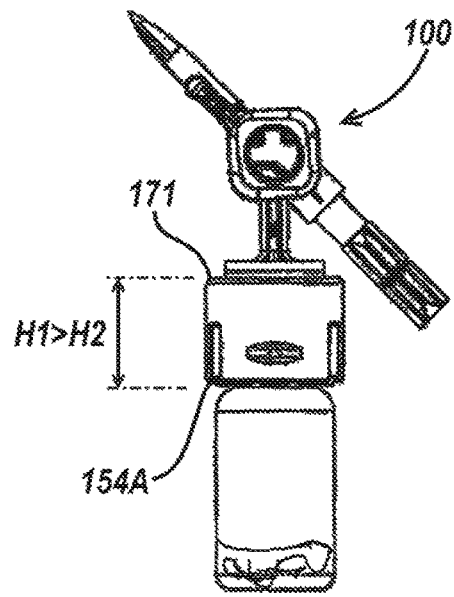
FIG. 11A is a front elevation view showing the FIG. 3 liquid transfer device after compaction of the telescopic vial adapter.
Figure 11B:
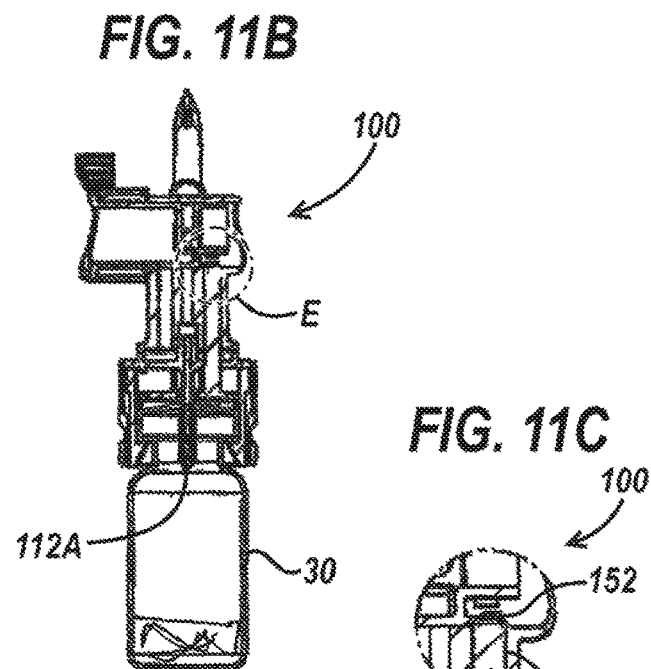
FIG. 11B is a longitudinal cross section of the liquid transfer device in FIG. 11A.
Figure 11C:
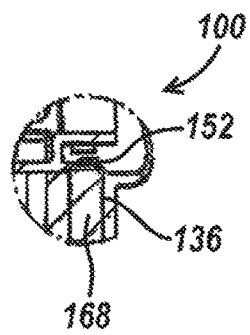
FIG. 11C is a close-up view of a feature of the liquid transfer device encircled E in FIG. 11B.

FIG. 11A to FIG. 11C show the liquid transfer device 100 after a healthcare provider has withdrawn the safety catch 121 from the outer vial adapter body 111 and compacted the telescopic vial adapter 108 such that the outer vial adapter body 111 snugly receives the inner vial adapter body 109 therein. The distal puncturing cannula tip 112A punctures the sheath 113 and thereafter the injection vial stopper 37 for establishing flow communication between the puncturing cannula 112 and the vial tube 32 for preparing a medicated infusion liquid. The telescopic vial adapter 108 has a compacted height H2 between the uppermost transverse outer vial adapter body wall 171 and the lowermost vial crown sleeve rim 154A where H1>H2. The compaction of the telescopic vial adapter 108 unlatches the latch mechanism 123 by way of the latch release member 168 flexing the latch stop 152 from the latch bore 136. The three position rotation stopcock arrangement 114 remains in its initial set-up position. The compaction precludes use of the pincers-like hand tool 200 to release the now punctured discrete injection vial 30.

Figure 12A:
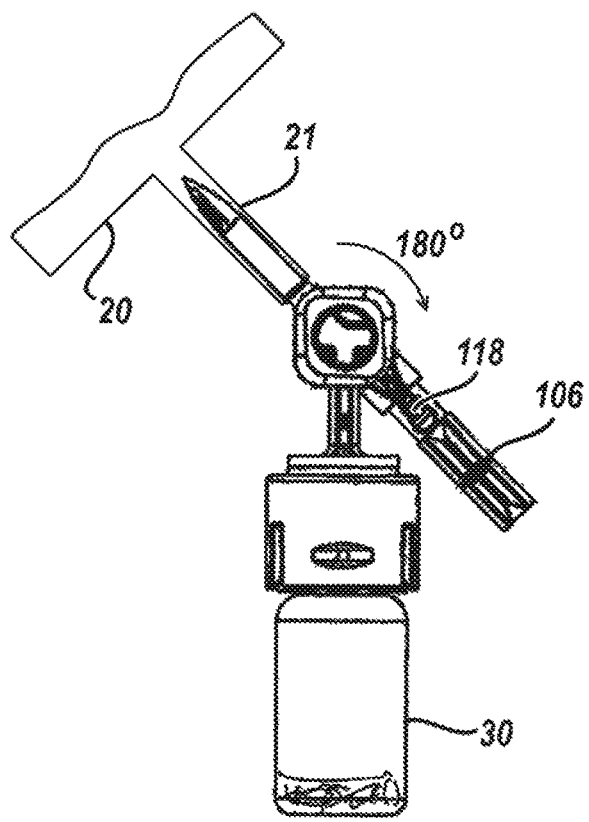
FIG. 12A is a front elevation view showing the FIG. 3 liquid transfer device ready for preparation of medicated infusion liquid.
Figure 12B:
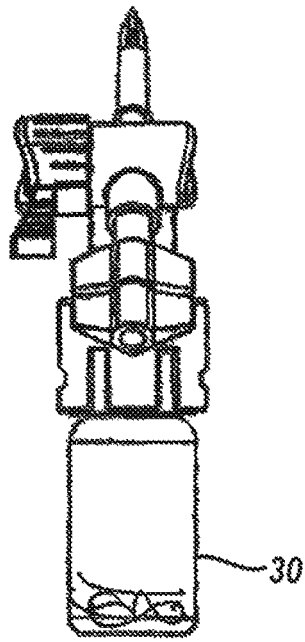
FIG. 12B is a side elevation view of the liquid transfer device ready for preparation of medicated infusion liquid.
Figure 12C:
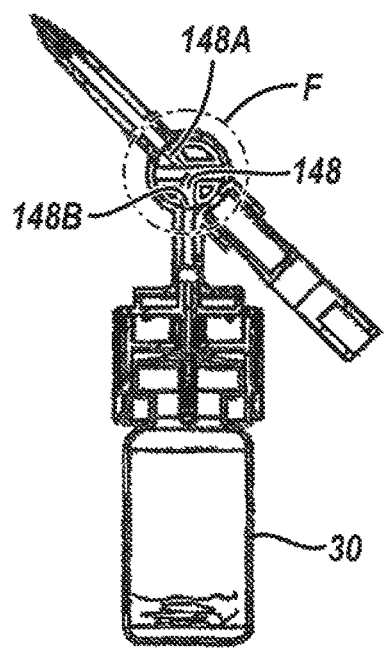
FIG. 12C is a longitudinal cross section of the liquid transfer device in FIG. 12B.
Figure 12D:
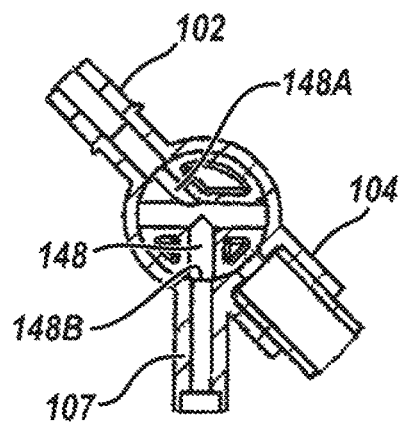
FIG. 12D is a close-up view of a feature of the liquid transfer device encircled F in FIG. 12C.

FIG. 12A and FIG. 12B show the liquid transfer device 100 after a healthcare provider has rotated the flow control member 116 with respect to the IV spike body 101 through approximately 180° to its intermediate preparation position. The flow control lever 118 indicates the substitute IV port 106 is sealed. The healthcare provider hears a click as the detent 144A snap clicks into the detent groove 137. The IV spike 102 is in flow communication with the puncturing cannula 112 through the preparation lumen 148. The healthcare provider inserts the IV spike 102 into the IV bag 20's IV port 21 and prepares the medicated infusion liquid in the IV bag by transferring liquid contents between the IV bag 20 and the injection vial 30. The healthcare provider preferably ensures that the last transfer of liquid contents empties the injection vial 30.

Figure 13A:
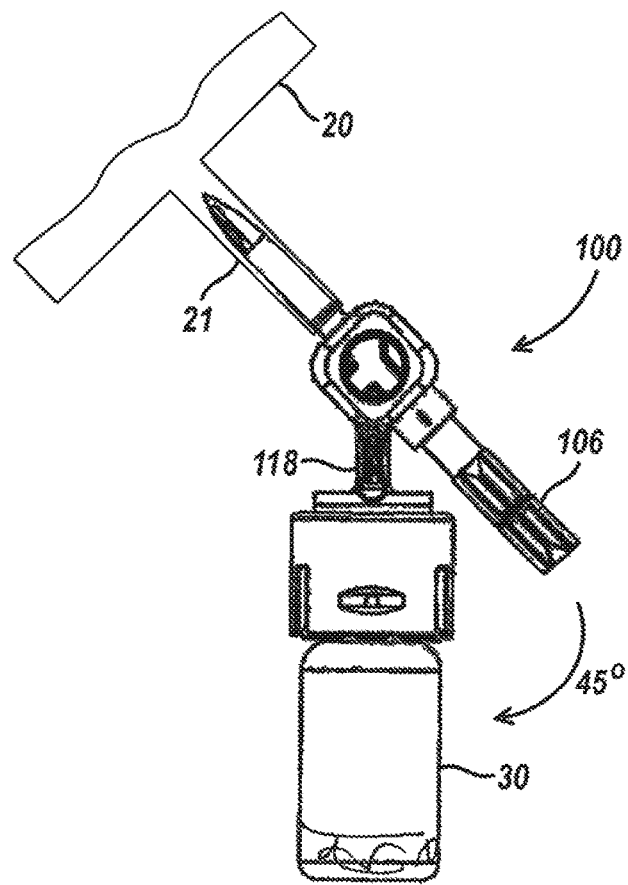
FIG. 13A is a front elevation view showing the FIG. 3 liquid transfer device ready for administration of medicated infusion liquid.
Figure 13B:
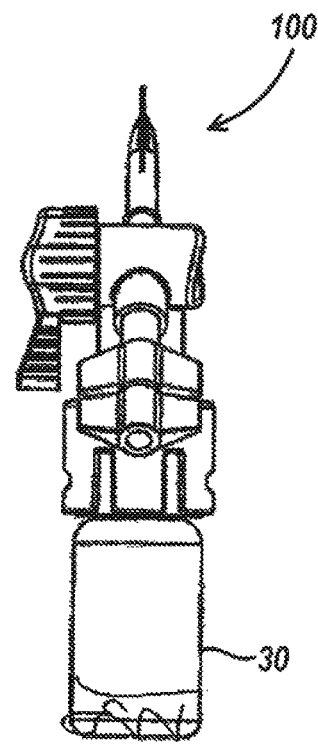
FIG. 13B is a side elevation view of the liquid transfer device ready for administration of medicated infusion liquid.
Figure 13C:
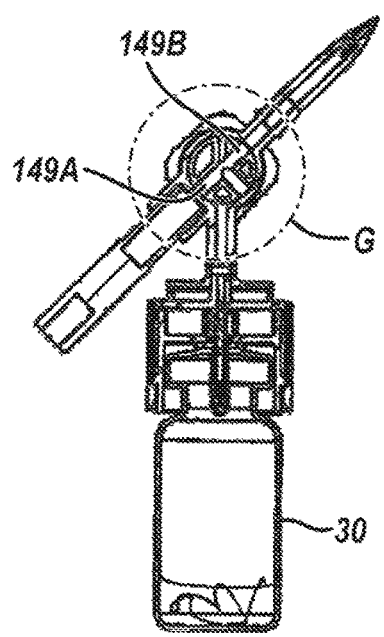
FIG. 13C is a longitudinal cross section of the liquid transfer device in FIG. 13B.
Figure 13D:
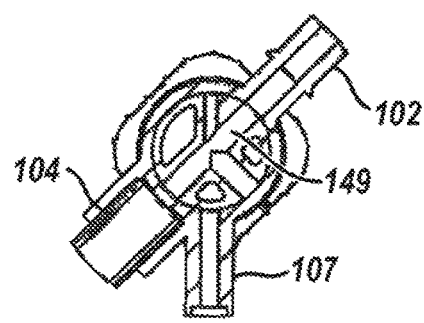
FIG. 13D is a close-up view of a feature of the liquid transfer device encircled G in FIG. 13C.

FIG. 13A and FIG. 13B show the liquid transfer device 100 after a healthcare provider has rotated the flow control member 116 with respect to the IV spike body 101 through approximately 45° to its final administration position. The flow control lever 118 indicates the telescopic vial adapter 108 is sealed. The healthcare provider hears a click as the detent 144B snap clicks into the detent groove 137. The stopcock rotation limit arrangement 124 stops further rotation of the flow control member 116. The IV spike 102 is in flow communication with the substitute IV port 106 through the administration lumen 149. The healthcare provider opens the substitute IV port 106 and inserts the infusion set's IV spike 51 thereinto and administers the medicated infusion liquid.

Figure 14:
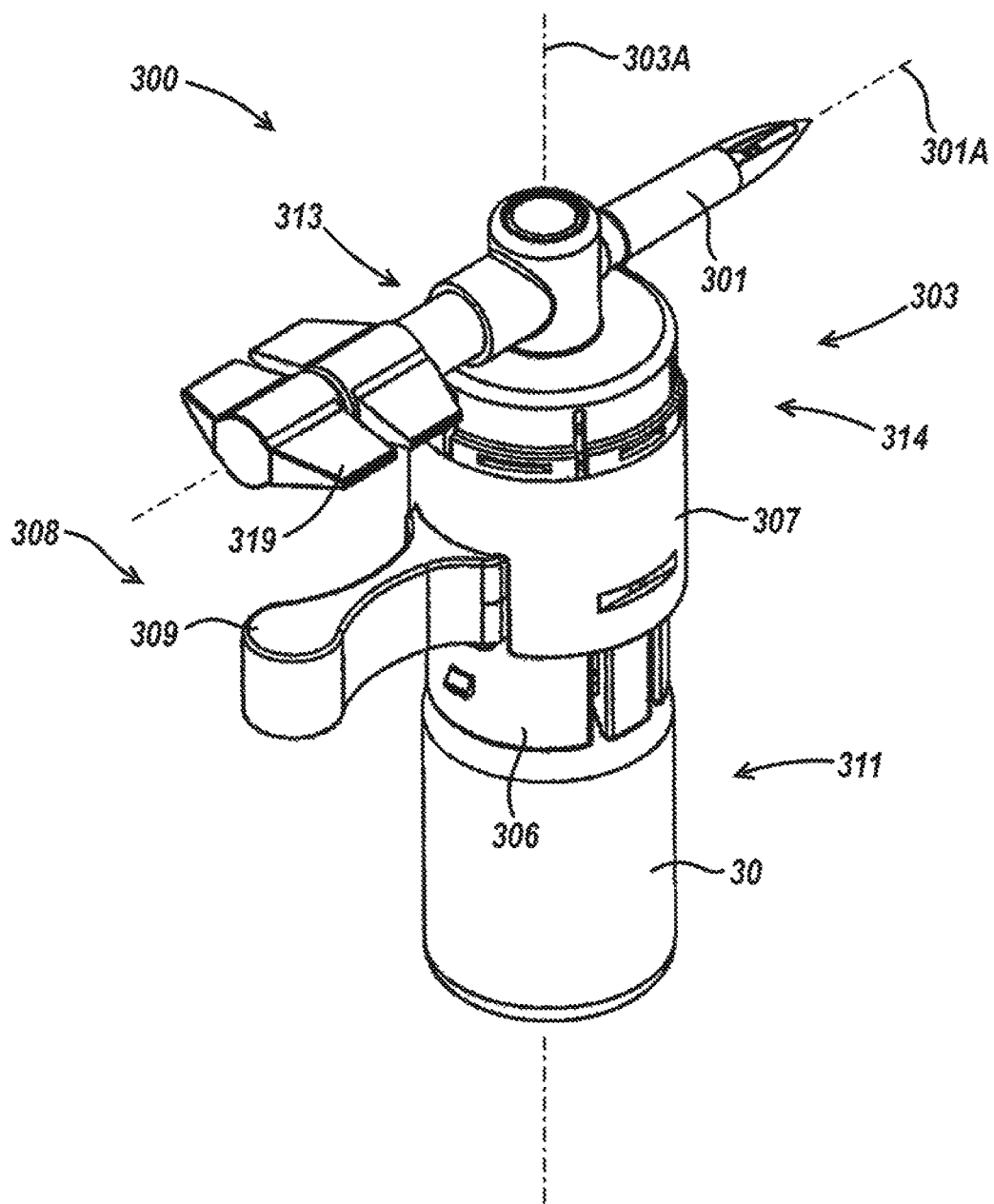
FIG. 14 is a front perspective view of a liquid transfer device according to a second embodiment of the invention including a telescopic vial adapter in a pre-compacted state mounted on a non-punctured intact discrete injection vial and a pincers-like hand tool for releasing the non-punctured intact discrete injection vial from the telescopic vial adapter.
Figure 15:
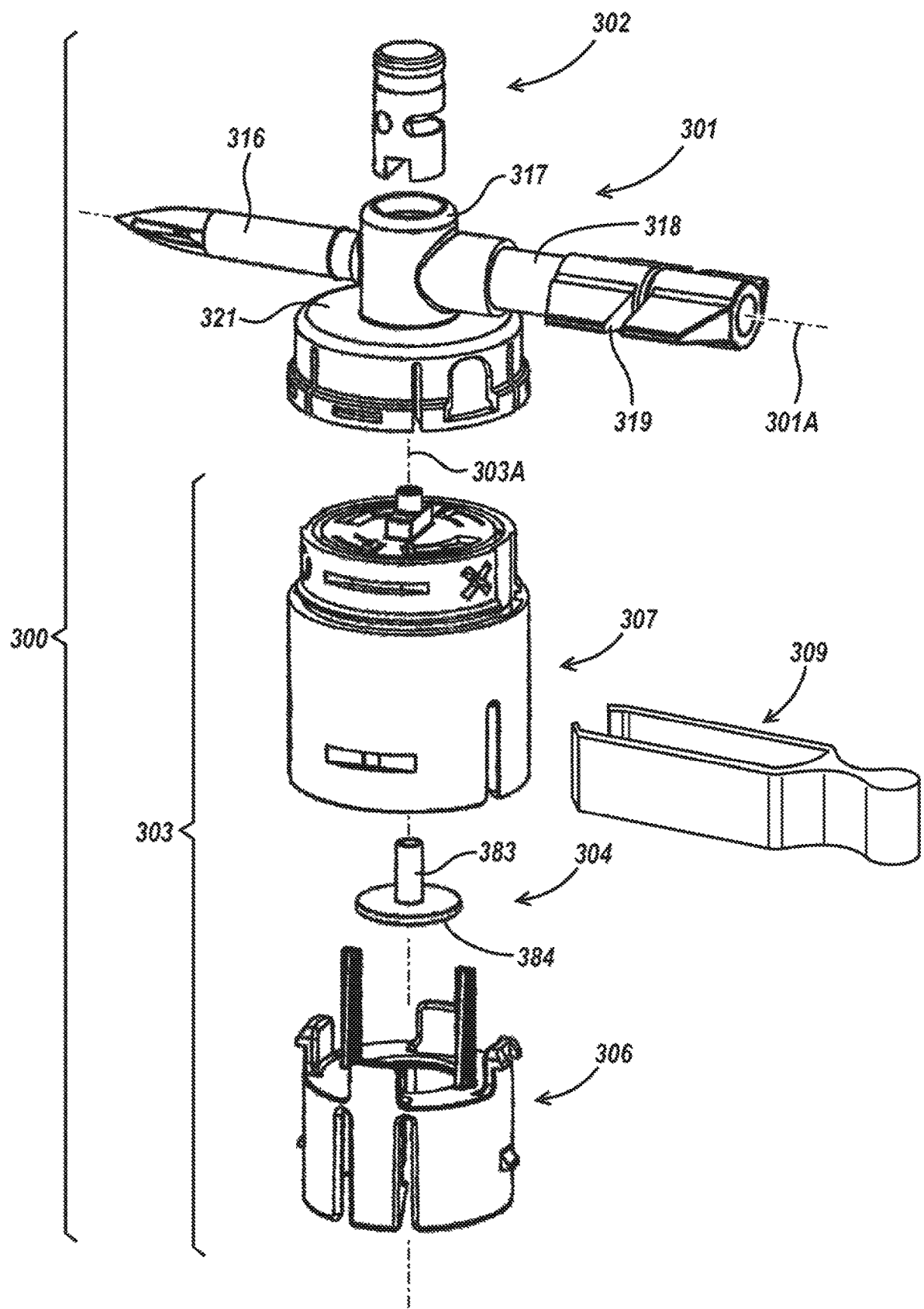
FIG. 15 is an exploded view of the FIG. 14 liquid transfer device.

FIG. 14 to FIG. 19C show a liquid transfer device 300 in accordance with a second embodiment of the invention. FIG. 14 also shows a pincers-like hand tool 200 for releasing a non-punctured intact discrete injection vial 30. The pincers-like hand tool 200 includes a pincers-like body 201 with an opposite pair of jaws 202 each terminating at an inward directed protrusion 303. The opposite pair of jaws 202 can be readily manually urged towards one another for applying a pincers-like compression for releasing a non-punctured intact discrete injection vial 30 as described hereinbelow with reference to FIG. 21A and FIG. 21B.

The liquid transfer device 300 includes an IV spike body 301 with a longitudinal IV spike body centerline 301A, a flow control member 302, a telescopic vial adapter 303 with a longitudinal vial adapter centerline 303A and an inverted T-shaped sealing member 304. The telescopic vial adapter 303 includes an inner vial adapter body 306 and an outer vial adapter body 307. The liquid transfer device 300 includes the following features: A safety catch mechanism 308 for preventing inadvertent user compaction of the telescopic vial adapter 303 from an initial pre-compacted state to a final compacted state. The safety catch mechanism 308 is implemented as a tuning fork-like safety catch 309 transversely extending through the outer vial adapter body 307 in the telescopic vial adapter 303's initial pre-compacted state. A clamping arrangement 311 for irreversibly clamping the telescopic vial adapter 303 in its compacted state. A three position rotation stopcock 312 for controlling flow direction of the liquid transfer device 300 in the telescopic vial adapter 303's compacted state. A latch mechanism 313 for preventing operation of the three position rotation stopcock 312 in the telescopic vial adapter 303's pre-compacted state. A stopcock position icon display arrangement 314 for displaying a stopcock position icon for indicating the flow direction of the liquid transfer device 300.

Figure 16A:
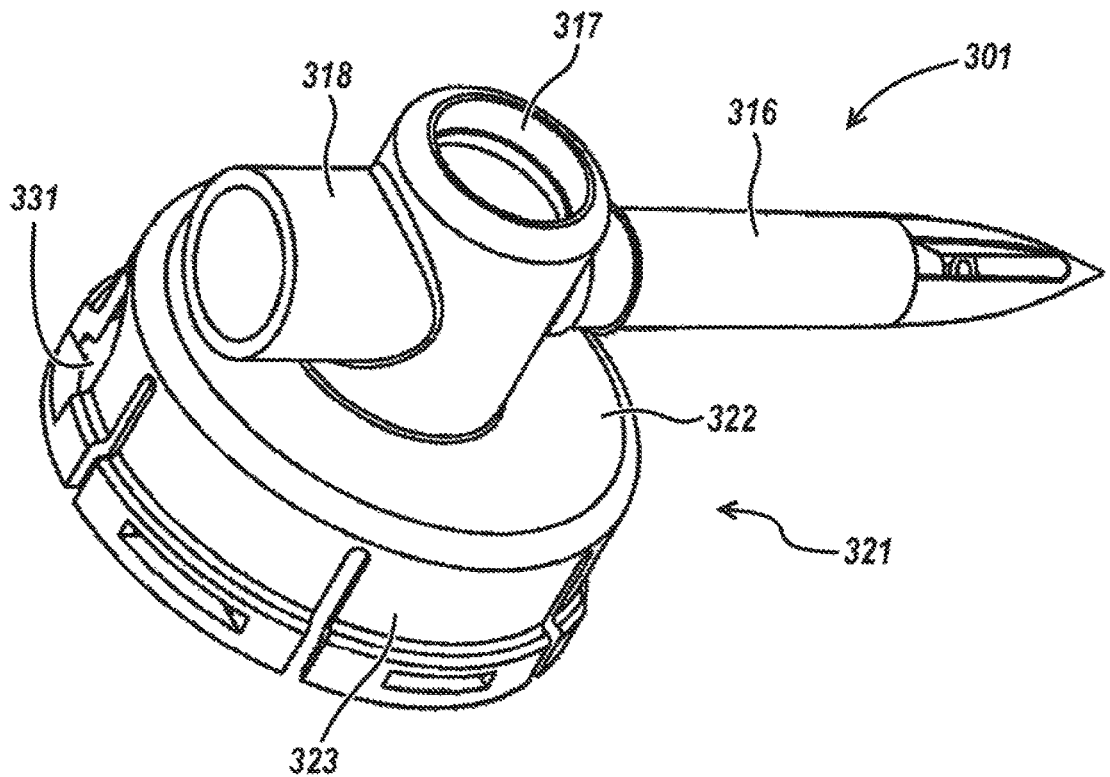
FIG. 16A is a top perspective view of an IV spike body of the FIG. 14 liquid transfer device.
Figure 16B:
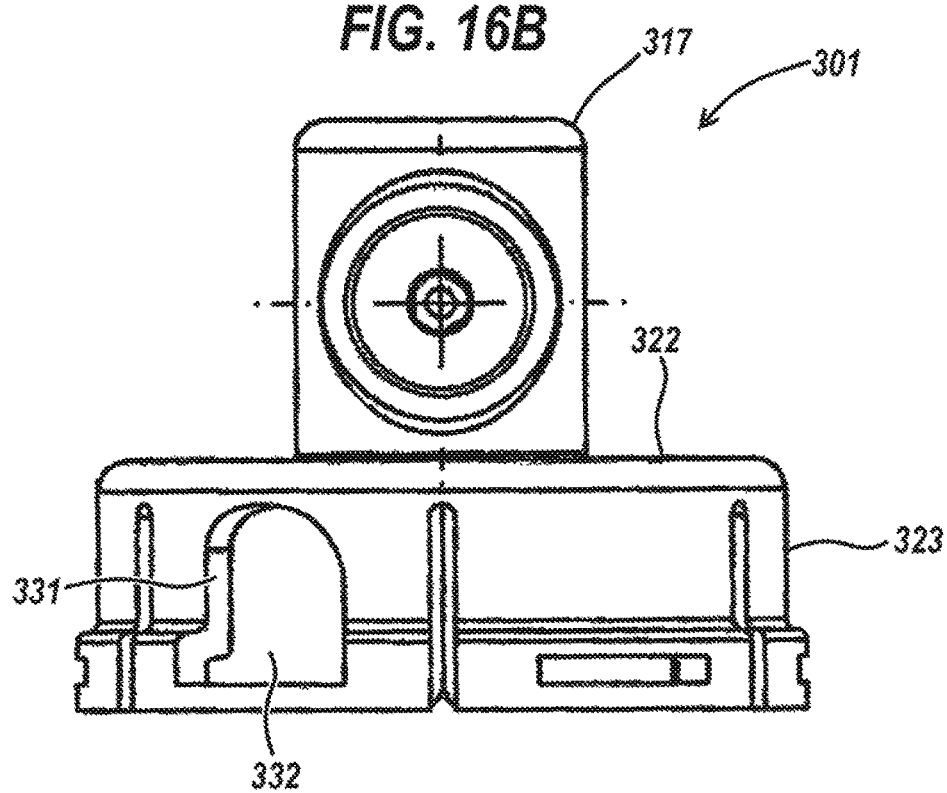
FIG. 16B is a front elevation view of the FIG. 16A IV spike body.

FIG. 16A to FIG. 16C show the IV spike body 301 has a trifurcated shape including a leading IV spike 316 for sealing insertion in the IV port 21, a central tubular flow control member port 317 for sealing receiving the flow control member 302 and a trailing tubular substitute IV port holder 318 for sealingly receiving a substitute IV port 319. The substitute IV port 319 can be implemented as a twist off component, a break off component, and the like. The central flow control member port 318 is formed with a downward depending telescopic vial adapter cap 321 for snap fitting on the telescopic vial adapter 303. The leading IV spike 316, the central flow control member port 317 and the trailing substitute IV port holder 318 are in continuous 3 way flow communication.

The telescopic vial adapter cap 321 has an uppermost transverse telescopic vial adapter cap wall 322 and a downward depending telescopic vial adapter cap rim 323. The uppermost transverse telescopic vial adapter cap wall 322 has an inside uppermost transverse telescopic vial adapter cap wall surface 322A including a diametric pair of latch recesses 324A and 324B constituting a component of the latch mechanism 313 for preventing relative rotation between the IV spike body 301 and the telescopic vial adapter 303 in the telescopic vial adapter 303's pre-compacted state.

The inside uppermost transverse telescopic vial adapter cap wall surface 322A includes a diametric pair of stopcock position recess arrays 326A and 326B constituting a component of the three position rotation stopcock 312 for determining the flow operation of the liquid transfer device 300. Each stopcock position recess array 326 includes an initial shutoff recess 327, an intermediate preparation recess 328 and a final administration recess 329. The shutoff recess 327 has a chamfered leading shutoff recess surface 327A for enabling a smooth transition of the three position rotation stopcock 312 from its initial shutoff position to its intermediate preparation position. The preparation recess 328 has a chamfered leading preparation recess surface 328A for enabling a smooth transition of the three position rotation stopcock 312 from its intermediate preparation position to its final administration position. The preparation recess 328 has a non-chamfered trailing preparation recess surface 328B for precluding reverting the three position rotation stopcock 312 from its intermediate preparation position to its initial shutoff position. The administration recess 329 has a chamfered trailing administration recess surface 329A for enabling a smooth transition of the three position rotation stopcock 312 from its final administration position to its intermediate preparation position in case a healthcare provider inadvertently directly rotated the three position rotation stopcock 312 from its initial shutoff position to its final administration position without preparing the medicated infusion liquid. Accordingly, the healthcare provider can dispose the three position rotation stopcock 312 at the intermediate preparation position for preparing medicated infusion liquid.

The downward depending telescopic vial adapter cap rim 323 has a diametric pair of stopcock position icon windows 331 constituting a component of the stopcock position icon display arrangement 314. The inside uppermost transverse telescopic vial adapter cap wall surface 322A has a diametric pair of downward depending screens radial 332 inward of the diametric pair of stopcock position icon windows 331. The diametric pair of downward depending screens radial 332 also constitute a component of the stopcock position icon display arrangement 314.

Figure 17:
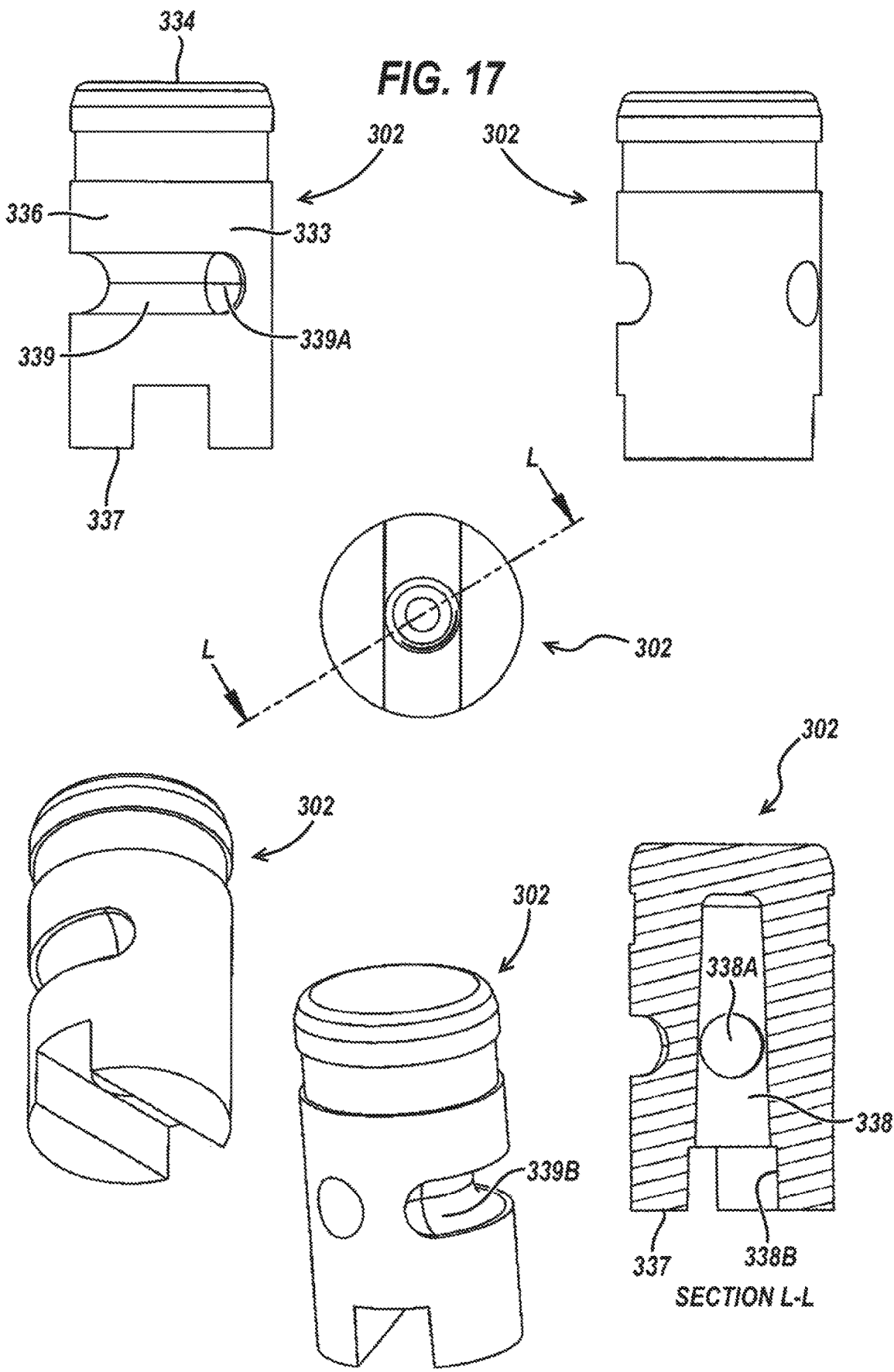
FIG. 17 illustrates different views of a flow control member of the FIG. 14 liquid transfer device.

FIG. 17 shows the flow control member 302 has a generally cylindrical flow control member body 333 including an uppermost flow control member surface 334, a peripheral flow control member surface 336, and a lowermost flow control member surface 337. The flow control member 302 has an internal L-shaped lumen 338 for preparing medicated infusion liquid. The L-shaped lumen 338 includes an IV spike opening 338A at the peripheral flow control member surface 336 and a puncturing cannula opening 338B at the lowermost flow control member surface 337. The peripheral flow control member surface 336 has a peripheral groove 339 for administering medicated infusion liquid. The external groove 339 has an IV spike opening 339A and a substitute IV port opening 339B. The lowermost flow control member surface 337 includes a flow control member keyway 341 for mechanically engaging the telescopic vial adapter 303 such that the flow control member 302 and the telescopic vial adapter 303 are rotatable with respect to the IV spike body 301 as a single integral body.

Figure 18A:
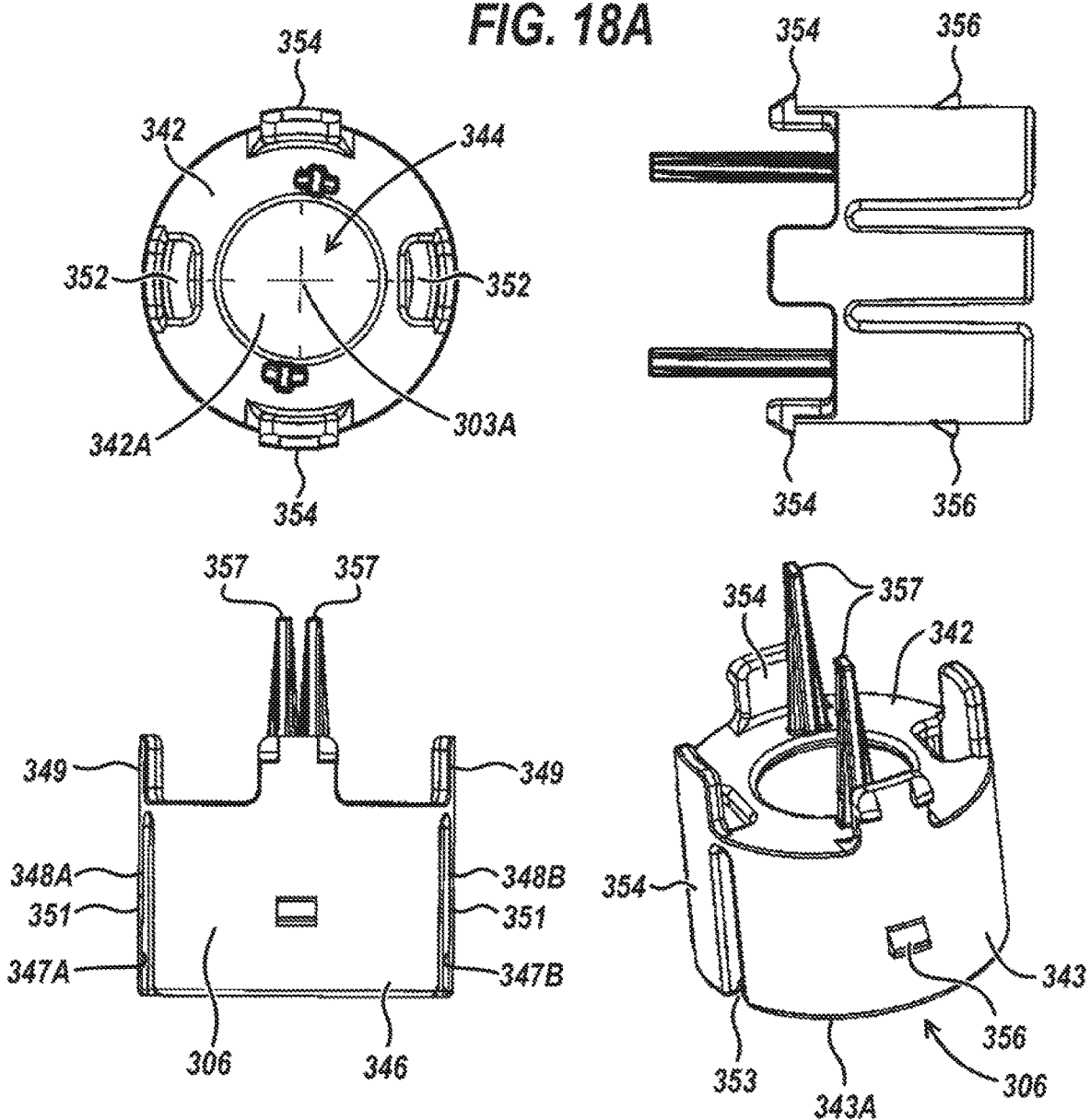
FIG. 18A illustrates different views of an inner vial adapter body of the FIG. 14 liquid transfer device.
Figure 18B:
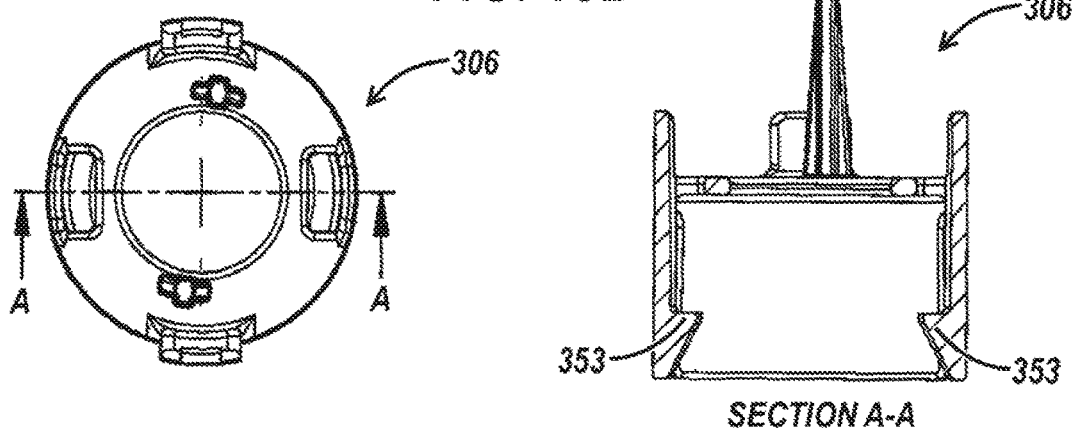
FIG. 18B illustrates a top plan view and a longitudinal cross section of the FIG. 18A inner vial adapter body.

FIG. 18A and FIG. 18B show the inner vial adapter body 306 has an inverted cup shape including an uppermost transverse annular inner vial adapter body wall 342 and a downward depending vial crown sleeve 343 with a lowermost vial crown sleeve rim 343A. The inner vial adapter body 306 bounds a vial crown cavity 344 for snugly receiving the vial crown 33 therein on telescopically snap fitting the inner vial adapter body 302 thereon. The uppermost transverse annular inner vial adapter body wall 342 has a center uppermost transverse annular inner vial adapter body wall throughgoing aperture 342A along the longitudinal vial adapter centerline 303A overlying the uppermost injection vial surface 41 on telescopically snap fitting on the discrete injection vial 30.

The vial crown sleeve 343 includes a major vial crown sleeve surround 346 with a first adjacent pair of longitudinal directed slits 347A and a second adjacent pair of longitudinal directed slits 347B for correspondingly forming a diametric pair of vial crown holding members 348A and 348B. The diametric pair of vial crown holding members 348 are pivotal with respect to the major vial crown sleeve surround 346 such that each vial crown holding member 348 has a proximal vial crown holding member section 349 and a distal vial crown holding member section 351. The uppermost transverse annular inner vial adapter body wall 342 preferably has a diametric pair of cutouts 352 inward of the diametric pair of vial crown holding members 348 such that the diametric pair of vial crown holding members 348 pivot on the uppermost transverse annular inner vial adapter wall 342.

The distal vial crown holding member sections 351 are each provided with a radial inward vial crown holding projection 353 towards the lowermost vial crown sleeve rim 343A for snap fitting under the vial crown 33 on telescopically snap fitting the inner vial adapter body 302 on the initially non-punctured intact discrete injection vial 30. Application of a pincers-like compression on the proximal vial crown holding member sections 349 towards the longitudinal vial adapter centerline 303A pivots the vial crown holding members 348 with respect to the major vial crown sleeve surround 346 thereby distancing the radial inward vial crown holding protrusions 353 from the longitudinal vial adapter centerline 303A.

The uppermost transverse annular inner vial adapter body wall 342 has a diametric pair of upright stops 354 correspondingly orthogonal to the diametric pair of vial crown holding members 348. The diametric pair of upright stops 354 prevent the inner vial adapter body 306 being inadvertently removed from the outer vial adapter body 307. The vial crown sleeve 343 includes a diametric pair of clamp members 356 towards the lowermost vial crown sleeve rim 434A and correspondingly orthogonal to the diametric pair of vial crown holding members 348. The diametric pair of clamp members 356 constitute a component of the clamping arrangement 311.

The uppermost transverse annular inner vial adapter body wall 342 has a diametric pair of upright latch members 357 for unlatching the latch mechanism 313 in the telescopic vial adapter 303's compacted state. The diametric pair of upright latch members 357 are orthogonal to the diametric pair of vial crown holding members 348.

Figure 19B:
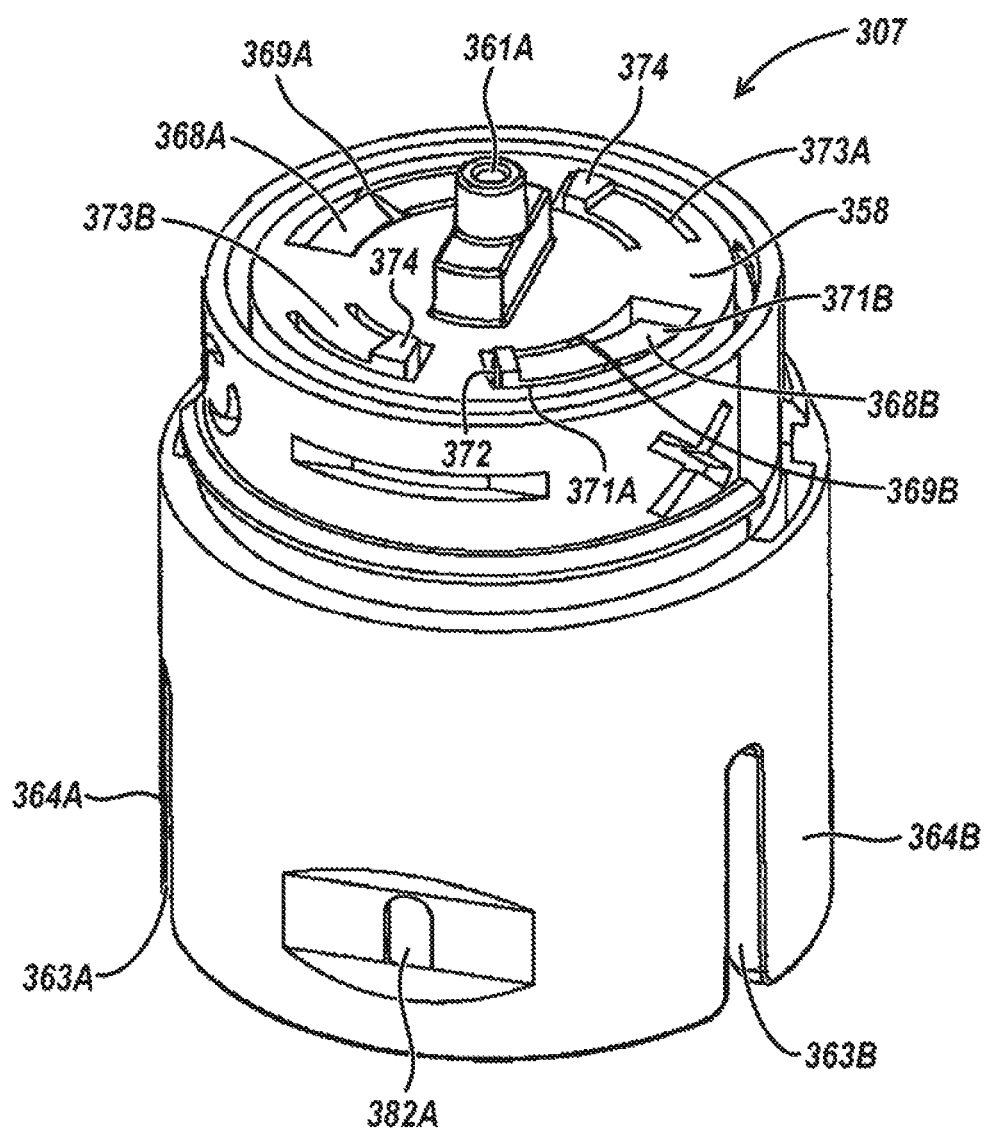
FIG. 19B is a front top perspective close-up view of the FIG. 19A outer vial adapter body.

FIG. 19A to FIG. 19C show the outer vial adapter body 307 has an inverted cup shape including an uppermost transverse outer vial adapter body wall 358 and a downward depending skirt 359 with a lowermost skirt rim 359A. The outer vial adapter body 307 bounds an inner vial adapter body cavity 361 for snugly telescopically receiving the inner vial adapter body 306 therein on compacting the telescopic vial adapter 303 from a pre-compacted state to a compacted state.

The uppermost transverse outer vial adapter body wall 358 includes a downward depending puncturing cannula 361 with a proximal puncturing cannula opening 361A and a distal puncturing cannula tip 361B. The uppermost transverse outer vial adapter body wall 358 has a box-shaped key 362 for insertion in the flow control member keyway 341. The box-shaped key 362 is formed with the proximal puncturing cannula opening 361A. The distal puncturing cannula tip 361B punctures the injection vial stopper 37 in the compacted state of the liquid transfer device 300.

The downward depending skirt 359 includes a first pair of adjacent longitudinal slits 363A and a second pair of adjacent longitudinal slits 363B for correspondingly forming a diametric pair of inner vial adapter body holding members 364A and 364B. The diametric pair of inner vial adapter holding members 364A and 364B correspondingly include internal longitudinal recesses 366A and 366B. The diametric pair of inner vial adapter body holding members 364A and 364B with their internal longitudinal recesses 366A and 366B constitute a component of the clamping arrangement 311. The diametric pair of internal longitudinal recesses 366A and 366B correspondingly include a diametric pair of lowermost recess rims 367A and 367B. The tuning fork-like safety catch 309 transverses through the first pair of adjacent longitudinal slits 363A and the second pair of adjacent longitudinal slits 363B for preventing compaction of the telescopic vial adapter 303 in its pre-compacted state.

The uppermost transverse outer vial adapter body wall 358 includes a diametric pair of horizontal latch members 368A and 368B. The horizontal latch members 368A and 368B have corresponding central pivot axes 369A and 369B for enabling a seesaw-like movement with respect to the uppermost transverse outer vial adapter body wall 358 between an initial latching position in the telescopic vial adapter 303's pre-compacted state for latching the latch mechanism 313 and a final unlatching position in the telescopic vial adapter 303's compacted state for unlatching the latch mechanism 313. The horizontal latch members 368A and 368B each have a first latch member end 371A and an opposite second latch member end 371B. The first latch member ends 371A each have an upright latch stop 372. The diametric pair of horizontal latch members 368A and 368B have a non-flexed position in which their diametric pair of upright latch stops 372 protrude above the uppermost transverse outer vial adapter body wall 358 in their initial latching position for insertion into the diametric pair of latch recesses 324. In the telescopic vial adapter 303's compacted state, the diametric pair of upright latch members 357 act against the second latch member ends 371B for pivoting the horizontal latch members 368A and 368B for urging the diametric pair of upright latch stops 372 from the diametric pair of latch recesses 324 into their final unlatching position.

The uppermost transverse outer vial adapter body wall 358 includes a diametric pair of horizontal cantilever stopcock members 373A and 373B orthogonal to the diametric pair of horizontal latch members 368A and 368B. The diametric pair of horizontal cantilever stopcock members 373A and 373B each has an upright stopcock position stop 374 for mechanical engagement with a stopcock position recess array 326.

The outer vial adapter body 307 includes a peripheral upright outer vial adapter body wall 376 surrounding the uppermost transverse outer vial adapter body wall 358. The peripheral upright outer vial adapter body wall 376 is disposed between the downward depending telescopic vial adapter cap rim 323 and the diametric pair of downward depending screens 332 and constitutes a component of the stopcock position icon display arrangement 314. The peripheral upright outer vial adapter body wall 176 includes a diametric pair of stopcock position icon arrays 377A and 377B for indicating the flow operation of the liquid transfer device 300. The stopcock position icon arrays 377A and 377B are implemented as throughgoing apertures in the peripheral upright outer vial adapter body wall 376. The stopcock position icon arrays 377A and 377B each include three icons as follows: a shutoff icon 378 implemented as a letter X, a preparation icon 379 implemented as an opposite pair of arcs, and an administration icon 381 implemented as a straight line.

The downward depending skirt 359 has a diametric pair of throughgoing discrete injection vial release apertures 382A and 382B orthogonal to the diametric pair of inner vial adapter body holding members 364A and 364B. The diametric pair of discrete injection vial release apertures 382A and 382B are designed for use with the pincers-like hand tool 200 to apply a pincers-like compression for releasing a non-punctured intact injection vial 30 and preclude manual application of the pincers-like compression.

The sealing member 304 has a sealing member tube 383 for mounting on the puncturing cannula 361 and a flat sealing member base 384 disposed in the central uppermost transverse annular inner vial adapter body wall throughgoing aperture 342A in the telescopic vial adapter 303's pre-compacted state. The central part of the flat sealing member base 384 acts as a sealing member septum 186 for maintaining sterility of the distal puncturing cannula tip 361B. The flat sealing member base 384 is sealing disposed on the uppermost injection vial surface 41 on telescopic mounting the liquid transfer device 300 on the injection vial 30. The sealing member septum 386 is intended to be punctured by the distal puncturing cannula tip 361B in the telescopic vial adapter 303's compacted state.

The use of the liquid transfer device 300 is now described with reference to FIG. 20A to FIG. 24B.

Figure 20A:
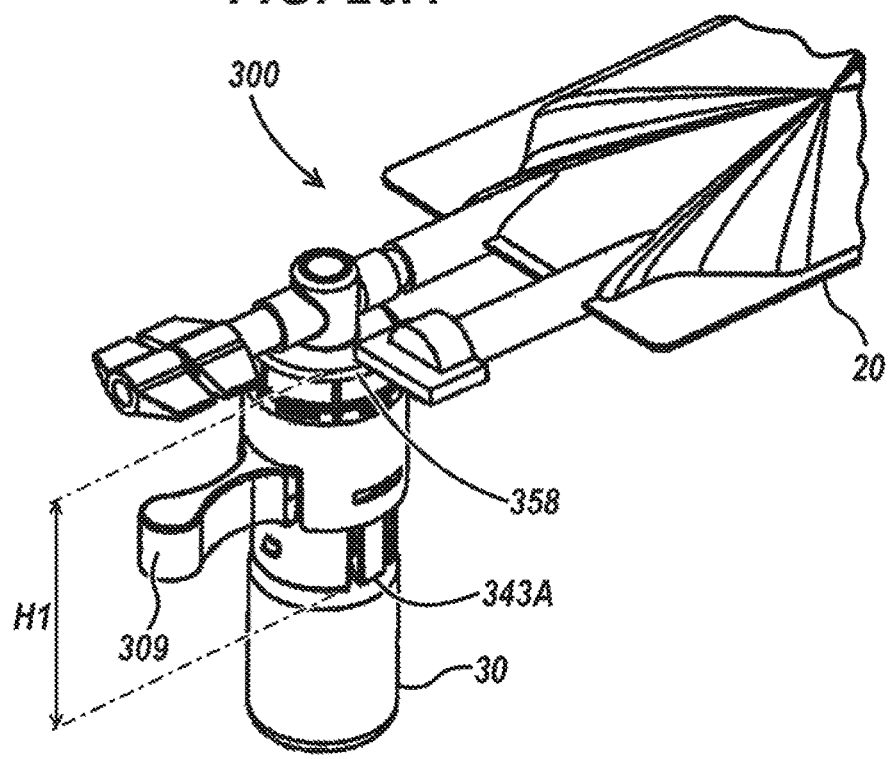
FIG. 20A is a front perspective view of a set-up arrangement including the liquid transfer device, the IV bag and the telescopic vial adapter in an initial pre-compacted state mounted on the discrete injection vial.
Figure 20B:
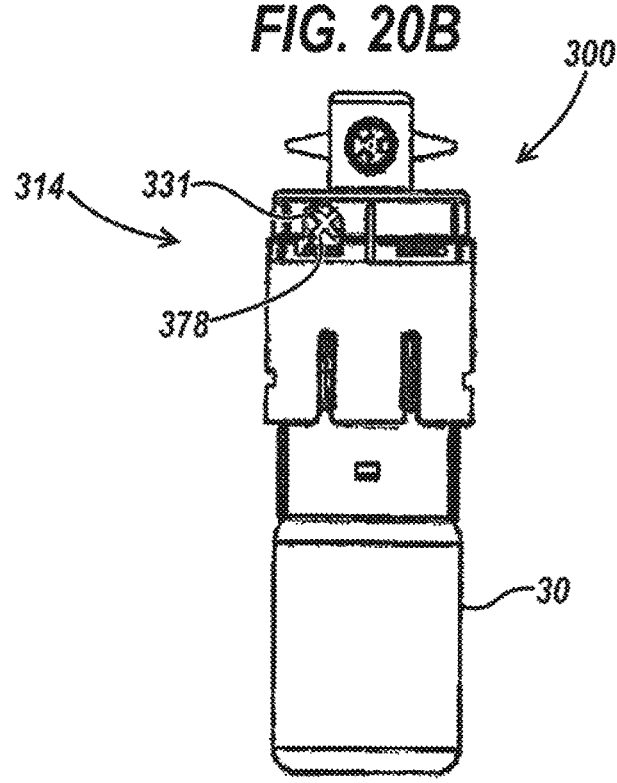
FIG. 20B is a front elevation view of the liquid transfer device with the stopcock position icon display arrangement showing the shutoff icon.

FIG. 20A shows a set-up arrangement after attachment of the liquid transfer device 300 to the IV bag 20 and snap fit mounting the telescopic vial adapter 303 in an initial pre-compacted state on the discrete injection vial 30. The tuning fork-like safety catch 309 transverses through the outer vial adapter body 307 preventing compaction of the telescopic vial adapter 303. The discrete injection vial release apertures 382A are aligned with the proximal vial crown holding member sections 349. The latch mechanism 313 latches the three position rotation stopcock 313 its initial shutoff rotation position. FIG. 20B shows the stopcock position icon display arrangement 314 displays the shutoff icons 378 "X" in the diametric pair of stopcock position icon windows 331. The telescopic vial adapter 303 has a pre-compacted height H1 between the uppermost transverse outer vial adapter body wall 358 and the lowermost vial crown sleeve rim 343A.

Figure 21A:
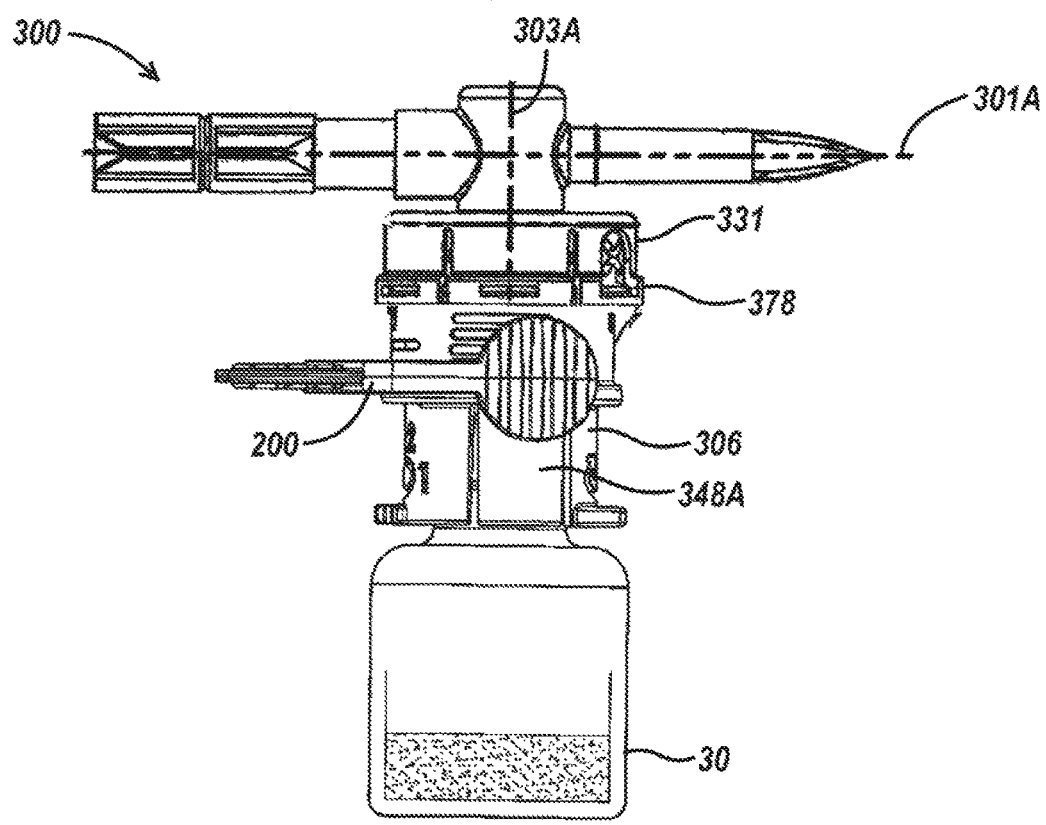
FIG. 21A is a right side elevation view of the liquid transfer device showing the use of the pincers-like hand tool for releasing the non-punctured intact discrete injection vial from the telescopic vial adapter.
Figure 21B:
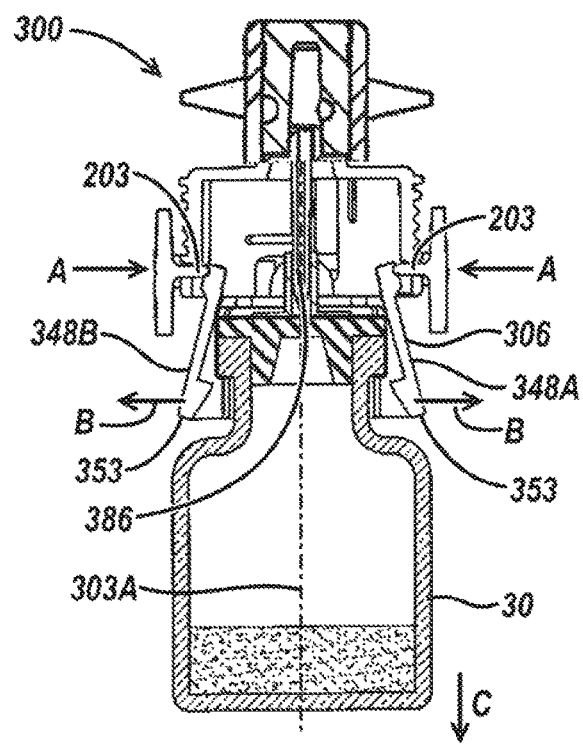
FIG. 21B is a longitudinal cross section of the FIG. 21A liquid transfer device.

In the event it is decided not to administer the medicament and re-use the non-punctured intact discrete injection vial, a healthcare provider takes the following steps as shown in FIG. 21A and FIG. 21B: The healthcare provider aligns the pincers-like hand tool 200 with the telescopic vial adapter 303 for inserting the opposite pair of inward directed protrusions 203 through the diametric pair of discrete injection vial release apertures 382. The healthcare provider applies a pincers-like compression on the proximal vial crown holding member sections 349 for urging them towards the longitudinal vial adapter centerline 303A as denoted by arrows A. The diametric pair of vial crown holding members 348 pivot with respect to the major vial crown sleeve surround 346 thereby distancing the diametric pair of radial inward vial crown holding projections 353 away from the longitudinal vial adapter centerline 303A as denoted by arrows B to release the non-punctured intact discrete injection vial 30. The healthcare provider withdraws the non-punctured intact discrete injection vial 30 from the inner vial adapter body 306 as denoted by arrow C for subsequent use notwithstanding that its tamper evidence cap 42 has been removed and discards the liquid transfer device 300.

Figure 22A:
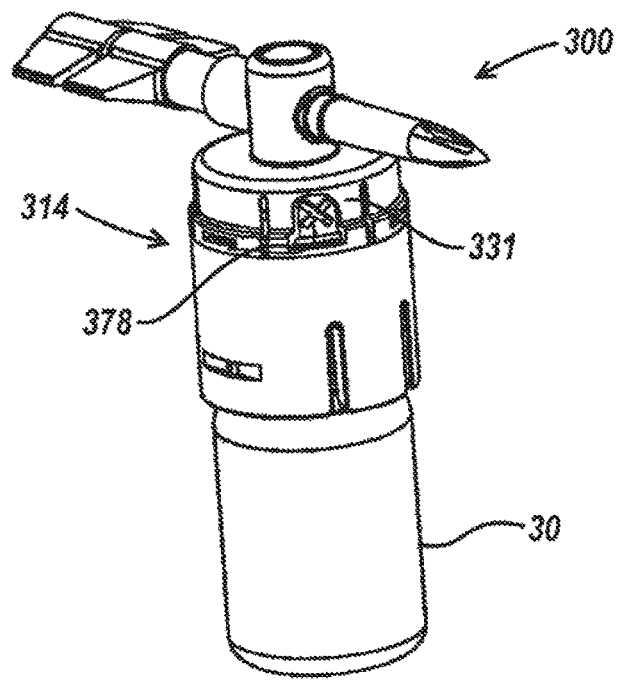
FIG. 22A is a front perspective view showing the liquid transfer device after compaction of the telescopic vial adapter.
Figure 22B:
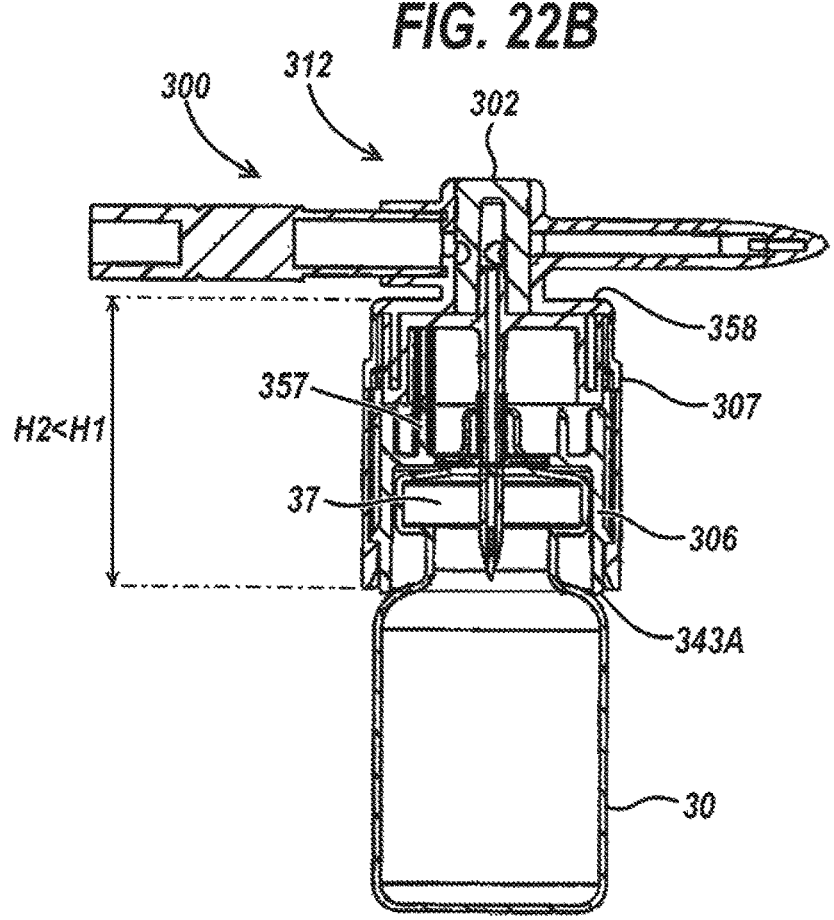
FIG. 22B is a longitudinal cross section of the FIG. 22A liquid transfer device.

FIG. 22A and FIG. 22B show the liquid transfer device 300 after a healthcare provider has withdrawn the safety catch 309 from the outer vial adapter body 307 and compacted the telescopic vial adapter 303 such that the outer vial adapter body 307 snugly receives the inner vial adapter body 306 therein. The distal puncturing cannula tip 361B punctures the sealing member septum 386 and thereafter the injection vial stopper 37 for establishing flow communication between the puncturing cannula 361 and the vial tube 32 for preparing a medicated infusion liquid. The telescopic vial adapter 303 has a compacted height H2 between the uppermost transverse outer vial adapter body wall 358 and the lowermost vial crown sleeve rim 343A where H1>H2. The compaction of the telescopic vial adapter 303 unlatches the latch mechanism 313 by urging the upright latch members 357 against the latch member ends 371B to urge the pivoted horizontal latch members 368 into their unlatching position. The three position rotation stopcock 312 remains in its initial shutoff rotation position and accordingly the stopcock position icon display arrangement 314 continues to display the preparation icons 379 "X" in the diametric pair of stopcock position icon windows 331 (see FIG. 22B). The compaction precludes use of the pincers-like hand tool 200 to release the discrete injection vial 30.

Figure 23A:
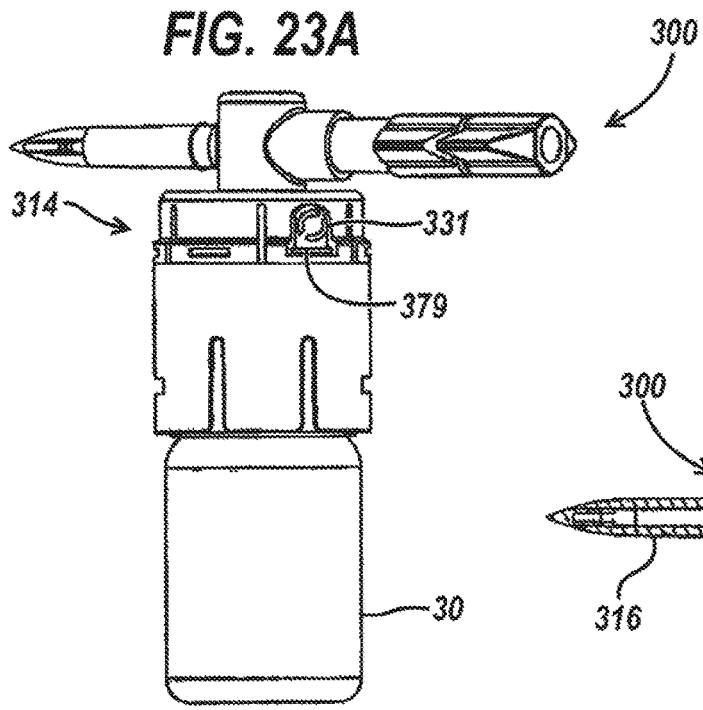
FIG. 23A is a front perspective view showing the liquid transfer device ready for preparation of medicated infusion liquid.
Figure 23B:
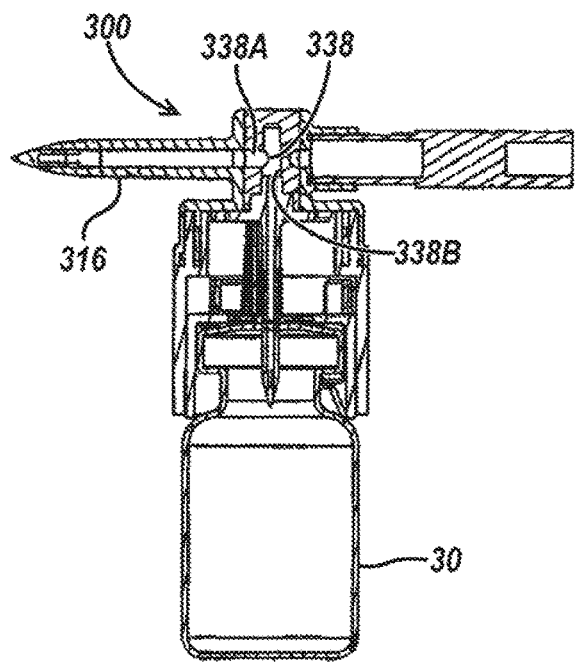
FIG. 23B is a longitudinal cross section of the FIG. 23A liquid transfer device.

FIG. 23A and FIG. 23B show the liquid transfer device 300 after a healthcare provider has rotated the IV spike body 301 with respect to the telescopic vial adapter 303 for urging the three position rotation stopcock 312 to its intermediate preparation rotation position. In this position, the cantilever stopcock members 373 have been rotated from the shutoff recesses 327 to the preparation recesses 328. The flow control member's internal L-shaped lumen 338 is in flow communication with the IV spike 316 and the puncturing cannula 361. FIG. 23B shows the stopcock position icon display arrangement 314 displays the preparation icons 379 "two opposite arcs" in the diametric pair of stopcock position icon windows 313. The healthcare provider prepares the medicated infusion liquid in the IV bag by transferring liquid contents between the IV bag 20 and the injection vial 30.

Figure 24A:
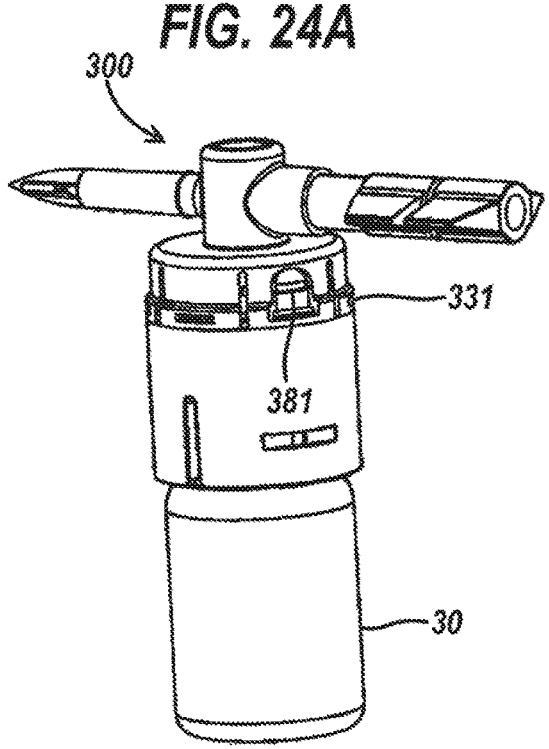
FIG. 24A is a front perspective view showing the liquid transfer device ready for administration of medicated infusion liquid.
Figure 24B:
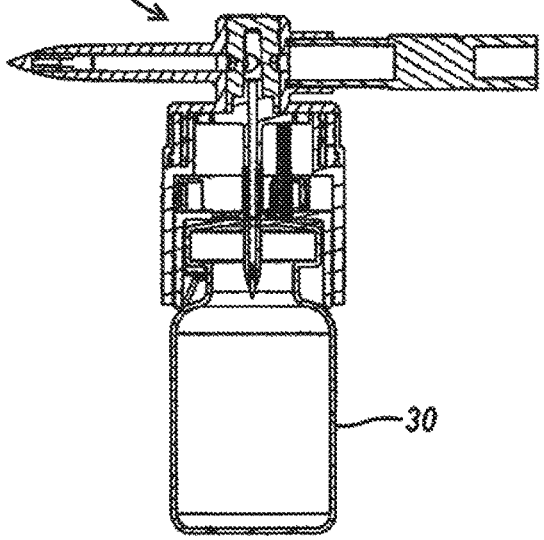
FIG. 24B is a longitudinal cross section of the FIG. 24A liquid transfer device.

FIG. 24A and FIG. 24B show the liquid transfer device 300 after a healthcare provider has rotated the IV spike body 301 with respect to the outer vial adapter body 303 for urging the three position rotation stopcock 312 to its final administration rotation position. In this position, the cantilever stopcock members 373 have been rotated from the preparation recesses 328 to the administration recesses 328. The flow control member's peripheral groove 339 is in flow communication with the IV spike 316 and the substitute IV port 318. FIG. 24B shows the stopcock position icon display arrangement 314 displays the administration icons 381 "straight line" in the diametric pair of stopcock position icon windows 331. The healthcare provider opens the substitute IV port 318 and inserts the infusion set's IV spike 51 into the substitute IV port 318 and administers the medicated infusion liquid.

FIG. 25 to FIG. 29C show a liquid transfer device 400 in accordance with a third embodiment of the invention. The liquid transfer device 400 includes a trifurcated Y-shaped IV spike body 401 with a longitudinal IV spike body centerline 401A, a leading IV spike 402, a central flow control member port 403 and a trailing substitute IV port holder 404 for sealingly receiving a substitute IV port 406. The flow control member port 403 has a flow control member port axis 416A transverse to the longitudinal IV spike body centerline 401A. The substitute IV port 406 can be implemented as a twist off component, a break off component, and the like. The IV spike 402 and the substitute IV port holder 404 are co-directional along the longitudinal IV spike body centerline 401A. The IV spike body 401 includes a vial adapter support 407 extending from the central flow control member port 403 and subtending an included approximately 135° angle with the IV spike 402 and a complementary included approximately 45° angle with the substitute IV port 404 in the FIG. 25 top perspective view. The liquid transfer device 400 includes a vial adapter 408 mounted on the vial adapter support 407. The vial adapter 408 may be rigidly and permanently mounted on the vial adapter support 407 or removably mounted on the vial adapter support 407. The telescopic vial adapter 408 has a longitudinal vial adapter centerline 408A intercepting the longitudinal IV spike body centerline 401A. The vial adapter 408 includes a puncturing cannula 412 (see FIG. 29A to FIG. 29C) for puncturing the injection vial stopper 37. The puncturing cannula 412 is protected by a thin sheath (not shown) for maintaining sterility until use of the liquid transfer device 400 for administering a medicated infusion liquid.

Figure 25:
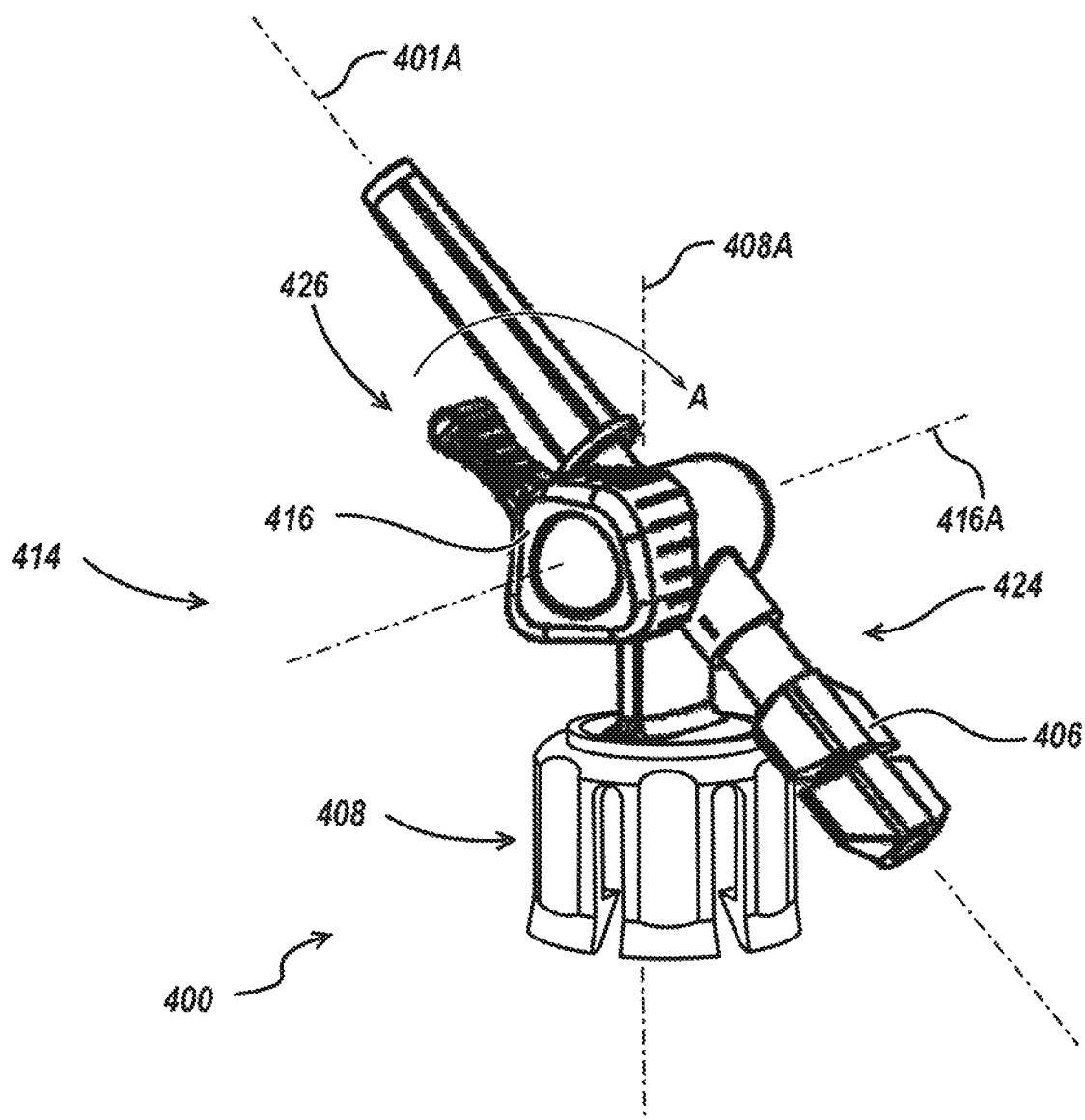
FIG. 25 is a front perspective view of a liquid transfer device according to a third embodiment of the invention.
Figure 26:
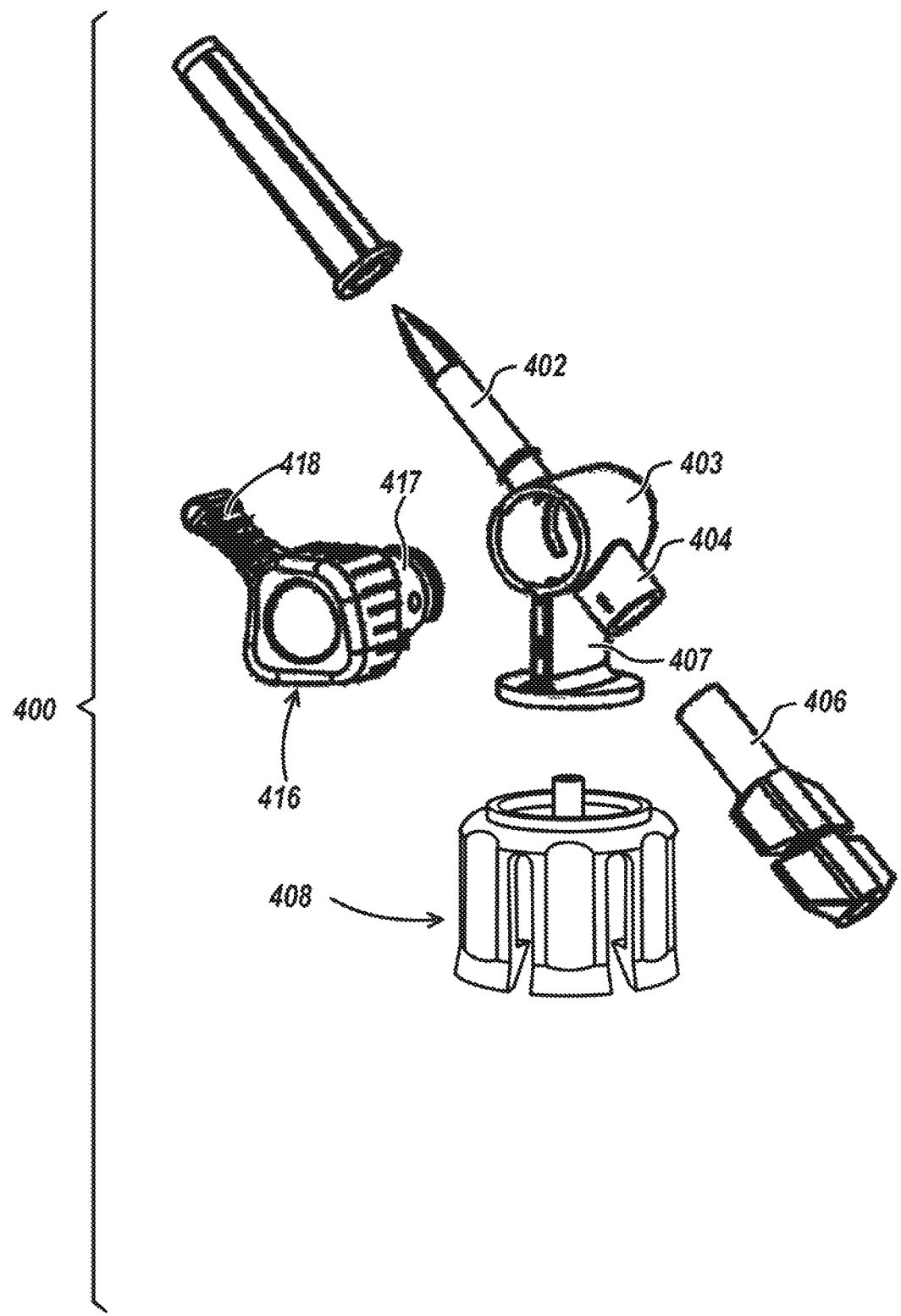
FIG. 26 is an exploded view of the FIG. 25 liquid transfer device.
Figure 27A:
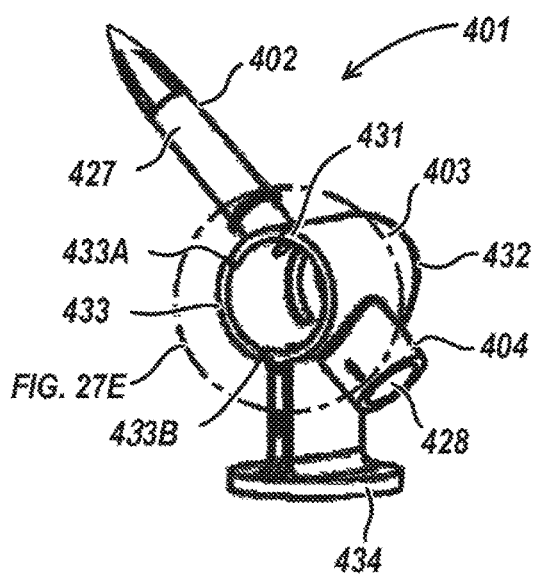
FIG. 27A is a top perspective view of an IV spike body of the FIG. 25 liquid transfer device.
Figure 27B:
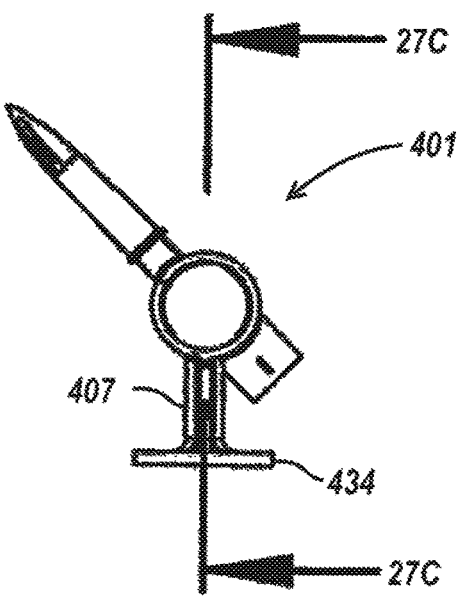
FIG. 27B is a top plan view of the IV spike body.
Figure 27C:
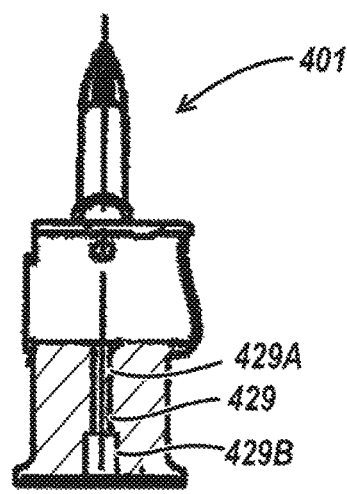
FIG. 27C is a longitudinal cross section of the IV spike body along line 27C-27C in FIG. 27B.
Figure 27D:
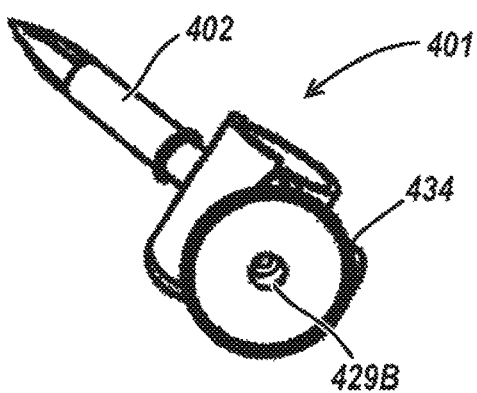
FIG. 27D is a bottom perspective view of the IV spike body.
Figure 27E:
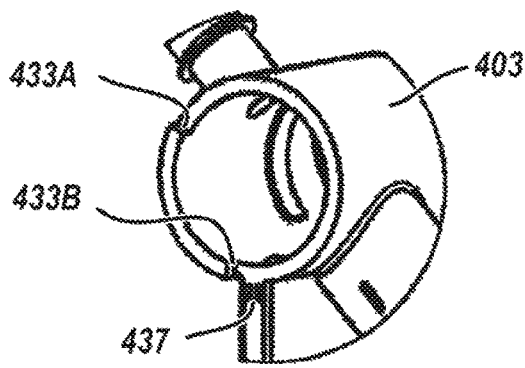
FIG. 27E is a close-up view of a feature of the IV spike body encircled A in FIG. 27A.
Figure 28A:
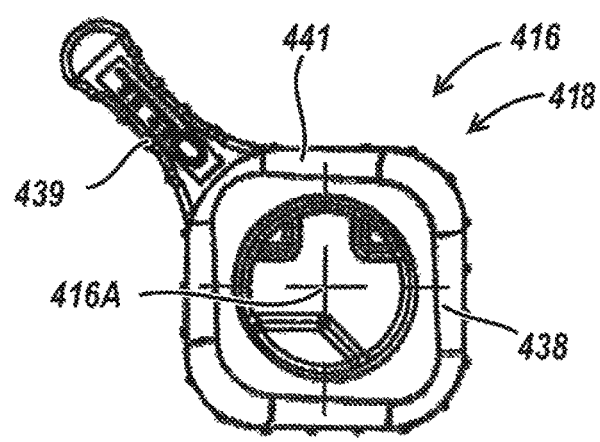
FIG. 28A is a top plan view of a flow control member of the FIG. 25 liquid transfer device.
Figure 28B:
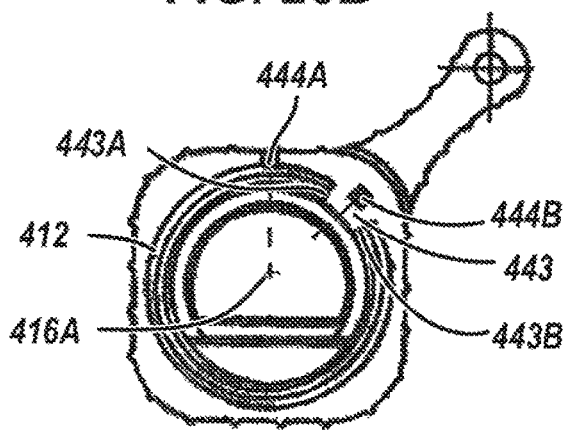
FIG. 28B is a bottom plan view of the flow control member.
Figure 28C:
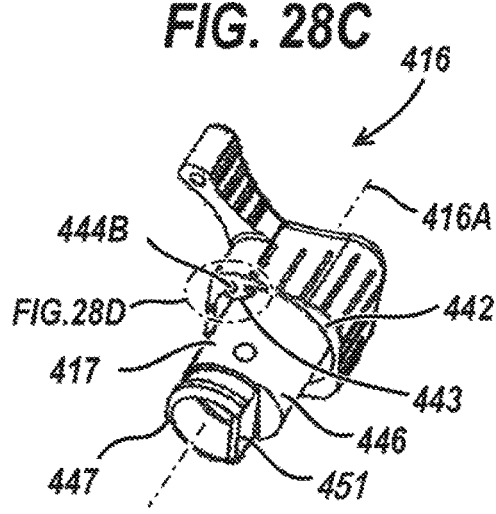
FIG. 28C is a bottom perspective view of the flow control member.
Figure 28D:
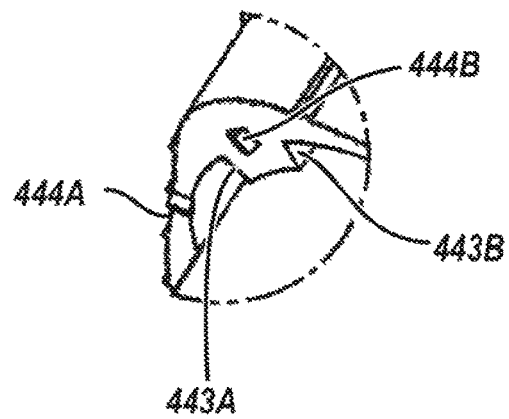
FIG. 28D is a close-up view of a feature of the flow control member encircled B in FIG. 28C.
Figure 28E:
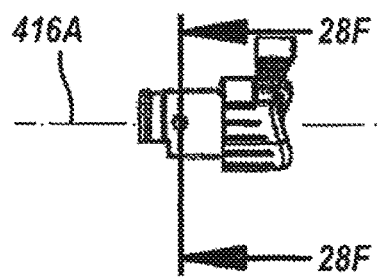
FIG. 28E is a side elevation view of the flow control member.
Figure 28F:
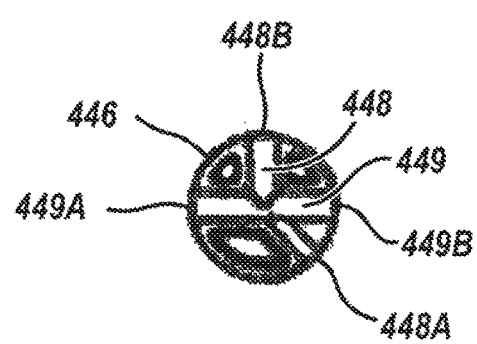
FIG. 28F is a transverse cross section of the flow control member along line 28F-28F in FIG. 28E.

The liquid transfer device 400 includes a hand operated three rotation position stopcock arrangement 414 having a L-shaped flow control member 416 for clockwise rotation relative to the IV spike body 401 as denoted by arrow A in the FIG. 25 top perspective view. The flow control member 416 has an axis of rotation 416A perpendicular to the longitudinal IV spike body centerline 401A and passing therethrough. The flow control member 416 includes a flow control shaft 417 securely and sealingly inserted in the flow control member port 403 and a flow control lever 418 intended to be gripped between a healthcare provider's thumb and forefinger for rotating same. The hand operated three rotation position stopcock arrangement 414 controls flow communication of the liquid transfer device 400. The hand operated three rotation position stopcock arrangement 414 involves clockwise rotation of the flow control member 416 in the FIG. 25 top perspective view from an initial set-up position to a final administration position for administering medicated infusion liquid to a patient via an intermediate preparation position for preparing medicated infusion liquid. The three rotation position stopcock arrangement 414 seals or blocks the IV spike 402 in the initial set-up position, the substitute IV port 406 in the intermediate administration position, and the vial adapter 408 in the final administration position.

The liquid transfer device 400 includes the following features: A stopcock rotation limit arrangement 424 for stopping a healthcare provider from further rotation of the flow control member 416 beyond the final administration position. A detent arrangement 426 for issuing audible alerts on rotating the flow control member 416 to its intermediate preparation position from its initial set-up position and to its final administration position from its intermediate preparation position. The audible alerts are preferably in the form of clicks by the snap click engagement of a detent into a detent groove such that a healthcare provider hears two clicks during the operation of the liquid transfer device 400. Accordingly the detent arrangement 426 can include a single detent groove and a pair of detents or alternatively a single detent and a pair of detent grooves.

FIG. 27A to FIG. 27E show the IV spike 402 has an IV spike lumen 427 in flow communication with the flow control member port 403 and its substitute IV port holder 404 has a substitute IV port holder lumen 428 co-linear with the IV spike lumen 427 and in flow communication with the flow control member port 403. The vial adapter support 407 includes a vial adapter support lumen 429 in flow communication with the flow control member port 403. The vial adapter support lumen 429 has a stepped configuration including a narrow diameter major vial adapter support lumen section 429A proximate the flow control member port 403 and a wide diameter minor vial adapter support lumen section 429B remote from the flow control member port 403.

The central flow control member port 403 includes a leading flow control member port rim 431 and an opposite trailing flow control member port rim 432. The leading flow control member port rim 431 has a stepped configuration constituting a component of the stopcock rotation limit arrangement 424. The leading flow control member port rim 431 includes a raised arc section 433 having an approximately 135° arc length thereby limiting rotation of the flow control member 416 about its axis of rotation 416A to approximately 225° from its initial set-up position to its final administration position. The raised arc section 433 has a raised arc section wall 433A and an opposite raised arc section wall 433B.

The vial adapter support 407 terminates in a vial adapter flange 434 for mounting on the vial adapter 408.

FIG. 28A to FIG. 28F show the flow control lever 418 has a generally square shaped major flow control lever section 438 and an elongated minor flow control lever section 439 for being gripped between a healthcare provider's thumb and forefinger. The flow control lever 418 has a top flow control lever surface 441 facing away from the flow control member port 403 having insignia for indicating an operative flow path of the liquid transfer device 400, namely, a preparation flow path between the IV spike 402 and the telescopic vial adapter 408 or an administration flow path between the IV spike 402 and the substitute IV port 406. The top flow control lever surface 441 bears the word OFF for indicating a sealed port to a healthcare provider in accordance with standard practice of three position rotation stopcocks.

The generally square shaped major flow control lever section 438 has a flow control lever rim 442 facing the flow control member port 403 and surrounding the flow control shaft 417. The flow control lever rim 442 has an inward directed projection 443 constituting a component of the stopcock rotation limit arrangement 424. The inward directed projection 443 has an inward directed projection wall 443A for abutting against the raised arc section wall 433A for preventing anti-clockwise rotation of the flow control member 416 relative to the IV spike body 401 in the FIG. 25 top perspective view. The inward directed projection 443 has an opposite inward directed projection wall 443B for abutting against the raised arc section wall 433B for stopping the flow control member 416's clockwise rotation in the FIG. 25 top perspective view at the flow control member 416's final administration position.

The flow control lever rim 442 is provided with a detent pair of the detent arrangement 426 as follows: a first detent 444A for snap fitting into the detent groove 437 at the flow control member 416's intermediate preparation position and a second detent 444B for snap fitting into the detent groove 437 at the flow control member 416's final administration position. The second detent engagement is before abutment of the opposite inward directed projection wall 443B against the raised arc section wall 433B. The detent pair 444 subtend an included approximately 45° angle corresponding to the angle of rotation from the flow control member 416's intermediate preparation position to its final administration position.

The flow control shaft 417 has a flow control shaft peripheral surface 446 and a flow control shaft end surface 447 opposite the flow control lever 418. The flow control shaft 117 includes an angled preparation lumen 448 for flow communication between the IV spike lumen 427 and the vial adapter support lumen 429 and a straight administration lumen 449 for flow communication between the IV spike lumen 427 and the substitute IV port holder lumen 428 midway therealong. The preparation lumen 448 and the administration lumen 449 are deployed on the same transverse plane and intercept at the axis of rotation 416A. The preparation lumen 448 includes a preparation lumen inlet aperture 448A and a preparation lumen outlet aperture 448B in the flow control shaft peripheral surface 446. The administration lumen 449 includes an administration lumen inlet aperture 449A and an administration lumen outlet aperture 449B in the flow control shaft peripheral surface 446. The angled preparation lumen 448 has an included approximately 135° angle equal to the included approximately 135° angle between the IV spike 402 and the vial adapter support 407.

The flow control shaft 417 includes a cutaway section 451 co-directional with the axis of rotation 416A towards the flow control shaft end surface 447.

FIG. 29A to FIG. 29C show the vial adapter body 408 has an inverted cup shape including an uppermost transverse outer vial adapter body wall 471 and longitudinal directed slits 458 for correspondingly forming vial flexible, crown holding members 459. The vial adapter body 408 bounds a vial crown cavity 456 for snugly receiving the vial crown 33 therein. Each vial crown holding member 459 includes at its distal end a radial inward vial crown holding projection 464 for snap fitting under the vial crown 33 on snap fitting the vial adapter body 408 on the intact discrete injection vial 30.

The uppermost transverse outer vial adapter body wall 471 includes a central upright connector 474 for insertion in the minor vial adapter support lumen section 429B and an opposite downward directed puncturing cannula 412. The puncturing cannula 412 has a distal puncturing cannula tip 412A for puncturing the injection vial stopper 37 when the vial adapter body is snap fitted on the intact discrete injection vial 30. The uppermost transverse outer vial adapter body wall 471 also includes a peripheral rim 477 for attachment to the vial adapter flange 434.

The use of the liquid transfer device 100 is now described with reference to FIG. 30A to FIG. 32B.

Figure 30A:
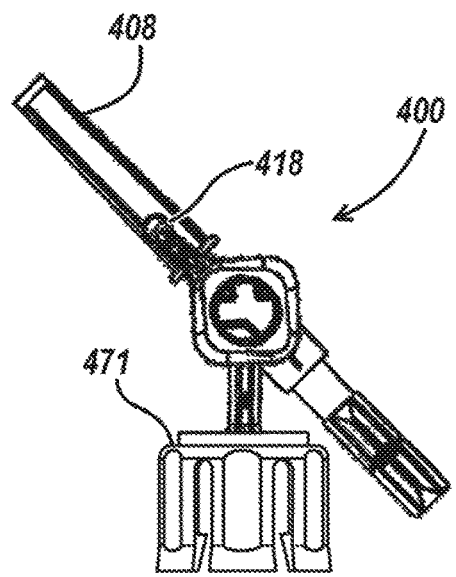
FIG. 30A is a front elevation view of the FIG. 25 liquid transfer device.
Figure 30B:
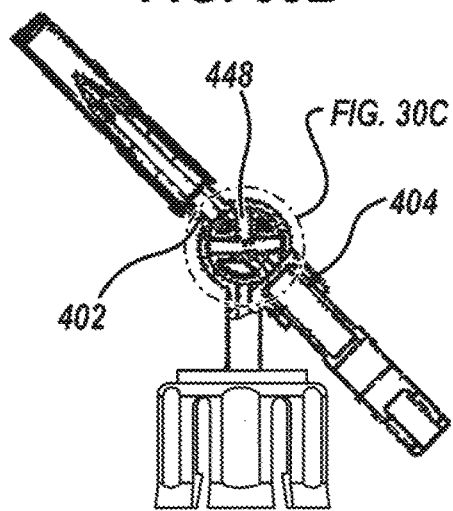
FIG. 30B is a longitudinal cross section of the liquid transfer device in FIG. 30A.
Figure 30C:
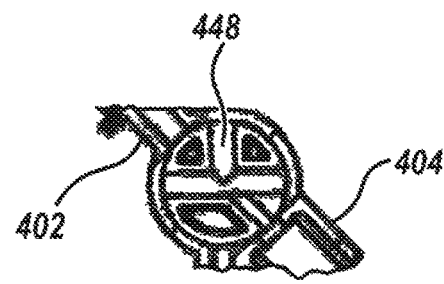
FIG. 30C is a close-up view of a feature of the liquid transfer device encircled in FIG. 30B.

FIG. 30A to FIG. 30C show a set-up arrangement of the liquid transfer device 400. The flow control lever 418 indicates the IV spike 402 is sealed (or blocked). The healthcare provider removes the tamper evidence cap 42 from the non-punctured intact discrete injection vial 30 and wipes the exposed uppermost injection vial surface 41. The healthcare provider mounts the vial adapter 408 onto the injection vial 30 ready for preparation of medicated infusion liquid in the infusion liquid container 20 for subsequent administration to a patient. When the healthcare professional mounts the vial adapter 408 onto the injection vial 30 the distal puncturing cannula tip 412A punctures the sheath and thereafter the injection vial stopper 37 for establishing flow communication between the puncturing cannula 412 and the vial tube 32 for preparing a medicated infusion liquid.

Figure 31A:
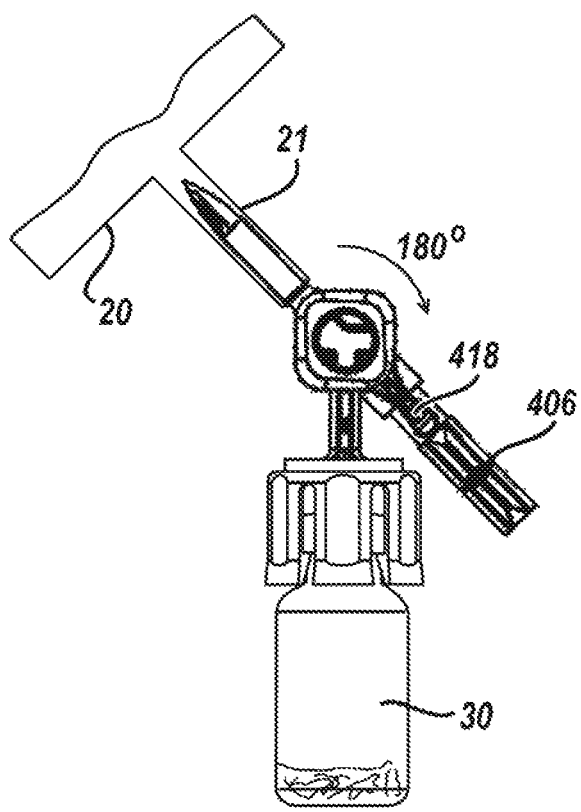
FIG. 31A is a front elevation view showing the FIG. 25 liquid transfer device ready for preparation of medicated infusion liquid.
Figure 31B:
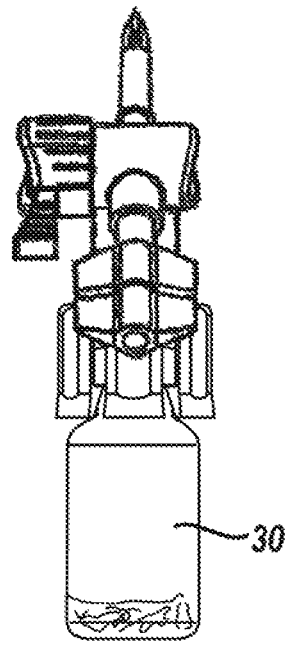
FIG. 31B is a side elevation view of the liquid transfer device ready for preparation of medicated infusion liquid.
Figure 31C:
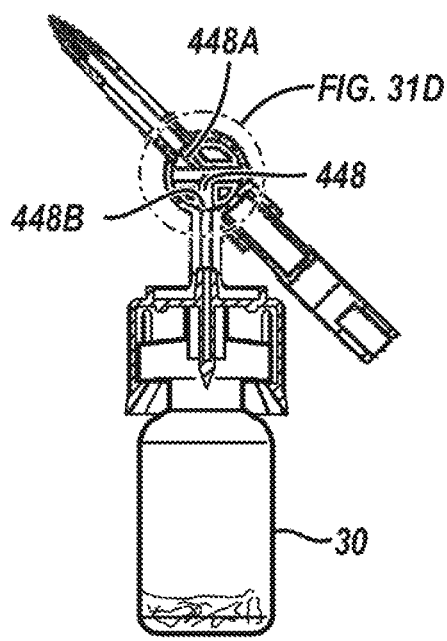
FIG. 31C is a longitudinal cross section of the liquid transfer device in FIG. 31B.
Figure 31D:
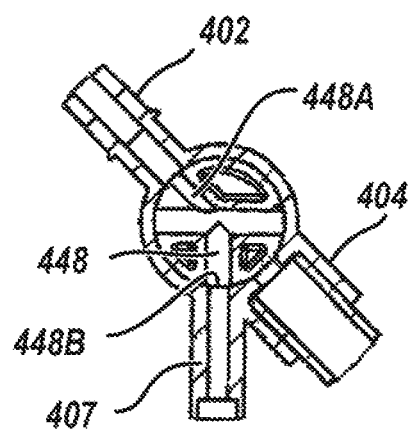
FIG. 31D is a close-up view of a feature of the liquid transfer device encircled in FIG. 31C.

FIG. 31A and FIG. 31B show the liquid transfer device 400 after a healthcare provider has rotated the flow control member 416 with respect to the IV spike body 401 through approximately 180° to its intermediate preparation position. The flow control lever 418 indicates the substitute IV port 406 is sealed. The healthcare provider hears a click as the detent 444A snap clicks into the detent groove 437. The IV spike 402 is in flow communication with the puncturing cannula 412 through the preparation lumen 148. The healthcare provider inserts the IV spike 402 into the IV bag 20's IV port 21 and prepares the medicated infusion liquid in the IV bag by transferring liquid contents between the IV bag 20 and the injection vial 30. The healthcare provider preferably ensures that the last transfer of liquid contents empties the injection vial 30.

Figure 32A:
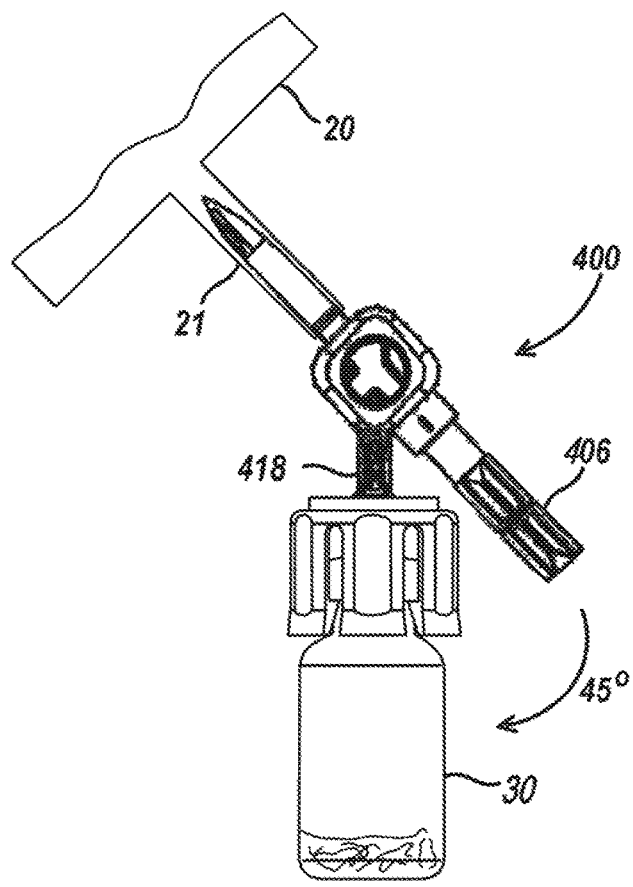
FIG. 32A is a front elevation view showing the FIG. 25 liquid transfer device ready for administration of medicated infusion liquid.
Figure 32B:
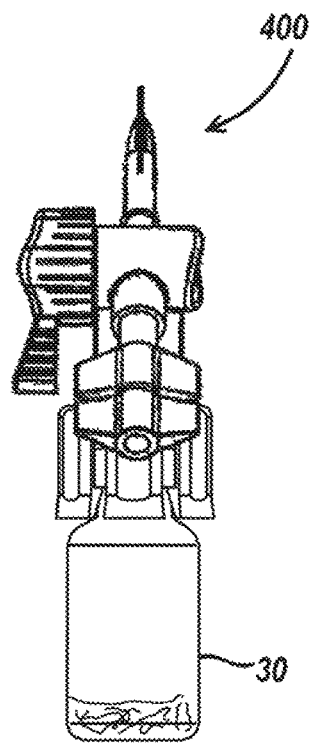
FIG. 32B is a side elevation view of the liquid transfer device ready for administration of medicated infusion liquid.
Figure 32C:
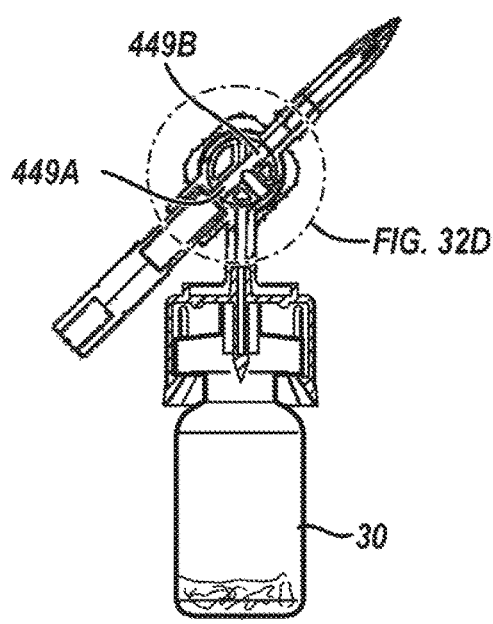
FIG. 32C is a longitudinal cross section of the liquid transfer device in FIG. 32B.
Figure 32D:
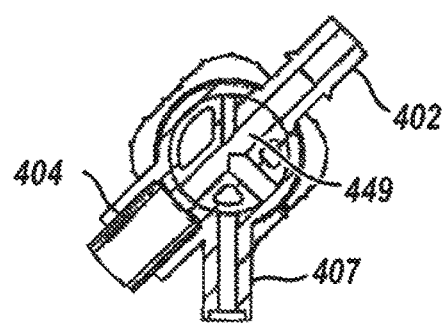
FIG. 32D is a close-up view of a feature of the liquid transfer device encircled D in FIG. 32C.

FIG. 32A and FIG. 32B show the liquid transfer device 400 after a healthcare provider has rotated the flow control member 416 with respect to the IV spike body 401 through approximately 45° to its final administration position. The flow control lever 118 indicates the telescopic vial adapter 408 is sealed. The healthcare provider hears a click as the detent 444B snap clicks into the detent groove 437. The stopcock rotation limit arrangement 424 stops further rotation of the flow control member 416. The IV spike 402 is in flow communication with the substitute IV port 406 through the administration lumen 449. The healthcare provider opens the substitute IV port 406 and inserts the infusion set's IV spike 51 thereinto and administers the medicated infusion liquid.

The embodiments described in association with FIG. 3 to FIG. 32B all include a three position arrangement: an initial set-up position for sealing the IV spike, an intermediate preparation position for enabling flow communication between the IV spike and the puncturing cannula for preparing (or mixing) a medicated infusion liquid, and a final administrating position for enabling flow communication between the IV spike and the substitute IV port for administering the medicated infusion liquid. In further embodiments, a two position arrangement is provided which includes a mixing or reconstituting position (i.e. an initial position) for enabling flow communication between the IV spike and the puncturing cannula; and an administering position (i.e. a final position) for enabling flow communication between the IV spike and the substitute IV port holder. In these further embodiments, the liquid transfer device would be provided in an initial position or state in which flow communication is enabled between the IV spike and the puncturing cannula. Furthermore, the movement of the flow control member may be limited to being moved between the two positions by providing a greater raised arc section (e.g. see the raised arc sections 133, 433), for example, by provided a raised arc section having an arc length of approximately 45°. For example the flow control member may be restricted to being moved between the positions illustrated FIG. 12A and FIG. 13A. Alternatively each stopcock position recess array 326 could include only two recesses, namely, a mixing recess 328 and an administration recess 329.

While particular embodiments of the present invention are illustrated and described, it would be obvious to those skilled in the art that various other changes and modifications can be made without departing from the spirit and scope of the invention.

A liquid transfer device is described hereinabove and shown in the attached drawings for use with an infusion liquid container containing an infusion liquid and having an intravenous (IV) port for administering the infusion liquid, an initially non-punctured intact discrete injection vial having a closed end vial tube containing a medicament, a tubular vial crown with a crown opening stopped by a non-punctured injection vial stopper, and an uppermost injection vial surface, and an infusion set including an IV spike for sealing insertion into an IV port and a connector for administration purposes to a patient.

The following is a non-exhaustive list of numbered aspects which may be claimed:

1. A liquid transfer device comprising:
   a vial adapter comprising a puncturing cannula for puncturing an injection vial stopper;
   an IV spike and a substitute IV port holder for receiving a substitute IV port;
   a flow control member port, wherein the IV spike, the substitute IV port holder and the puncturing cannula are in flow communication with the flow control member port; and
   a flow control member sealingly inserted in the flow control member port, wherein rotation of the flow control member between a plurality of positions controls flow communication of the liquid transfer device, the positions comprising:
   a mixing or reconstituting (or reconstitution) position for enabling flow communication between the IV spike and the puncturing cannula; and an administering (or administration) position for enabling flow communication between the IV spike and the substitute IV port holder.

2. The liquid transfer device of aspect 1, wherein the positions comprise a sealing position for sealing the IV spike or a further position for blocking flow communication between the IV spike, the puncturing cannula and the substitute IV port.

3. The liquid transfer device of aspect 1 or aspect 2, comprising a detent arrangement configured to issue audible alerts when the flow control member is rotated to the intermediate position from the initial position and to the final position from the intermediate position.

4. The liquid transfer device of aspect 3, wherein the detent arrangement comprises a pair of detents for engagement into a single detent groove or a single detent for engagement into a pair of detent grooves.

5. The liquid transfer device of any preceding aspect, comprising a rotation limit arrangement configured to limit rotation of the flow control member from the initial position to the final position.

6. The liquid transfer device of any preceding aspect, wherein the vial adapter comprising an inner vial adapter body having a vial crown cavity for receiving a vial crown, and an outer vial adapter body, wherein the outer vial adapter body slidingly receives the inner vial adapter body therein when the vial adapter undergoes compaction from a pre-compacted state to a compacted state.

7. The liquid transfer device of aspect 6, comprising a safety catch mechanism arranged to prevent inadvertent compaction of the vial adapter.

8. The liquid transfer device of any preceding aspect, comprising an IV spike body comprising an uppermost transverse cap wall having the flow control body formed thereon, the IV spike body configured to receive the vial adapter.

9. The liquid transfer device of aspect 8, when dependent on aspect 6 or aspect 7, wherein the uppermost transverse cap wall includes a latch recess;

wherein an uppermost transverse cap wall of the outer vial adapter body comprises a pivotal, horizontal latch member, the latch member having a first latch member end and an opposite second latch member end, the first latch member end having an upright latch stop, wherein the latch member has a non-flexed position in which the upright latch stop protrudes above the uppermost transverse cap wall and into the latch recess to prevent rotation of the flow control member when the vial adapter is in the pre-compacted state;

wherein the inner vial adapter body comprises an upright latch release member arranged to act against the second latch member end to pivot the horizontal latch member and urge the upright latch stop from the latch recess when the vial adapter is compacted to enable rotation of the flow control member.

10. The liquid transfer device of aspect 8 or aspect 9, wherein the uppermost transverse cap wall includes a position recess array, each position recess array includes an initial recess, an intermediate recess and a final recess, and wherein the vial adapter comprises a cantilever member having an upright position stop for mechanical engagement with the position recess array.

11. The liquid transfer device of aspect 10, wherein the initial recess has a chamfered leading surface for enabling a smooth transition of the flow control member from the initial position to the intermediate position, wherein the intermediate recess has a chamfered leading surface for enabling a smooth transition of the flow control member from the intermediate position to the final position, wherein the intermediate recess has a non-chamfered trailing surface for precluding reverting the flow control member from the intermediate position to the initial position, and wherein the final recess has a chamfered trailing surface for enabling a smooth transition of the flow control member from the final position to the intermediate position.

12. The liquid transfer device of any one of aspects 8 to 11, comprising a position icon display arrangement arranged to display the initial, intermediate and final positions of the flow control member.

13. The liquid transfer device of aspect 12, wherein the IV spike body comprising a downward vial adapter cap rim configured to receive the vial adapter, wherein the downward vial adapter cap rim comprising a position icon window and wherein the vial adapter comprising an uppermost outer body wall comprising a position icon array arranged to be displayed in the position icon window.

14. The liquid transfer device of aspect 13, wherein the position icon array includes three icons comprising a letter X, an opposite pair of arcs, and a straight line.

15. The liquid transfer device of aspect 14, wherein:
when the flow control member is in the initial position the letter X is displayed in the position icon window; when the flow control member is in the intermediate position the opposite pair of arcs is displayed in the position icon window; and when the flow control member is in the final position the straight line is displayed in the position icon window.

The invention claimed is:

1. A liquid transfer device comprising:
a vial adapter comprising a puncturing cannula for puncturing an injection vial stopper;
an IV spike and a substitute IV port holder for receiving a substitute IV port;
a flow control member port, wherein the IV spike, the substitute IV port holder and
the puncturing cannula are in flow communication with the flow control member port; and
a flow control member sealingly inserted in the flow control member port, wherein rotation of the flow control member between a plurality of positions controls flow communication of the liquid transfer device, the positions comprising:
a mixing position for enabling flow communication between the IV spike and the puncturing cannula; and
an administering position for enabling flow communication between the IV spike and the substitute IV port holder,
wherein the vial adapter further comprises an inner vial adapter body having a vial crown cavity for receiving a vial crown, and an outer vial adapter body, wherein the outer vial adapter body slidingly receives the inner vial adapter body therein when the vial adapter undergoes compaction from a pre-compacted state to a compacted state.

2. The liquid transfer device of claim 1, wherein the positions comprise a sealing position for sealing the IV spike.

3. The liquid transfer device of claim 1, wherein the vial adapter comprises a vial crown cavity for receiving a vial crown and longitudinal directed slits for correspondingly forming flexible, vial crown holding members, wherein each vial crown holding member comprises at its distal end a radial inward vial crown holding projection.

4. A liquid transfer device comprising:
a vial adapter comprising a puncturing cannula for puncturing an injection vial stopper;
an IV spike and a substitute IV port holder for receiving a substitute IV port;
a flow control member configured to move for enabling flow communication between the IV spike and the puncturing cannula and for enabling flow communication between the IV spike and the substitute IV port holder,
wherein the vial adapter comprises an inner vial adapter body having a vial crown cavity for receiving a vial crown, and an outer vial adapter body, wherein the outer vial adapter body slidingly receives the inner vial adapter body therein when the vial adapter undergoes compaction from a pre-compacted state to a compacted state.

5. The liquid transfer device of claim 4, wherein the liquid transfer device further comprises a safety catch mechanism arranged to prevent inadvertent compaction of the vial adapter, and wherein the safety catch mechanism is arranged to transversely extend through the outer vial adapter body when the vial adapter is in the pre-compacted state to prevent inadvertent compaction of the vial adapter.

6. The liquid transfer device of claim 4, wherein the inner vial adapter body comprises a diametric pair of pivotal vial crown holding members, wherein each vial crown holding member has a proximal vial crown holding member section, and a distal vial crown holding member section provided with a radial inward vial crown holding projection for snap fitting under the vial crown, and wherein pincers-like compression on the proximal vial crown holding member sections towards a longitudinal centerline of the vial adapter pivots the vial crown holding members, thereby distancing the radial inward vial crown holding projections from the longitudinal centerline of the vial adapter.

7. The liquid transfer device of claim 4, further comprising a latch mechanism for preventing rotation of the flow control member when the vial adapter is in a pre-compacted state.

8. The liquid transfer device of claim 1, further comprising a vial adapter support extending from the flow control member port, wherein the vial adapter support comprises a latch bore;

wherein the flow control member comprises a latch stop configured to engage with the latch bore to prevent rotation of the flow control member when the vial adapter is in a pre-compacted state; and wherein the inner vial adapter body comprises an upright latch release member which extends through the outer vial adapter body into the latch bore to urge the latch stop out of the latch bore when the vial adapter is compacted to enable rotation of the flow control member.

9. The liquid transfer device of claim 1, wherein the flow control member comprises a flow control body inserted in the flow control member port.

10. The liquid transfer device of claim 9, wherein the flow control body comprises a flow control lever configured to permit rotation of the flow control body.

11. The liquid transfer device of claim 9, wherein the flow control body comprises an angled lumen for flow communication between the IV spike and the puncturing cannula, and a straight lumen for flow communication between the IV spike and the substitute IV port holder.

12. The liquid transfer device of claim 1, further comprising an IV spike body comprising an uppermost transverse cap wall having the flow control body formed thereon, the IV spike body configured to receive the vial adapter, wherein the uppermost transverse cap wall includes a latch recess;

wherein an uppermost transverse cap wall of the outer vial adapter body comprises a pivotal, horizontal latch member, the latch member having a first latch member end and an opposite second latch member end, the first latch member end having an upright latch stop, wherein the latch member has a non-flexed position in which the upright latch stop protrudes above the uppermost transverse cap wall and into the latch recess to prevent rotation of the flow control member when the vial adapter is in the pre-compacted state;

wherein the inner vial adapter body comprises an upright latch release member arranged to act against the second latch member end to pivot the horizontal latch member and urge the upright latch stop from the latch recess when the vial adapter is compacted to enable rotation of the flow control member.

13. The liquid transfer device of claim 12, further comprising a position icon display arrangement arranged to display the initial, intermediate and final positions of the flow control member.

14. The liquid transfer device of claim 12, wherein the flow control member comprises a flow control body inserted in the flow control member port and wherein the flow control body comprises an angled lumen for flow communication between the IV spike and the puncturing cannula, and a peripheral groove for flow communication between the IV spike and the substitute IV port holder.

15. The liquid transfer device of claim 14, wherein the flow control body comprises a keyway and the vial adapter comprises a key for insertion into the keyway, and wherein rotation of the flow control body with respect to the vial adapter rotates the flow control member with respect to the flow control body.

* * * * *